United States Patent
Feld et al.

(10) Patent No.: US 7,993,258 B2
(45) Date of Patent: *Aug. 9, 2011

(54) IN-VIVO METHOD AND DEVICE FOR IMPROVING DIASTOLIC FUNCTION OF THE LEFT VENTRICLE

(75) Inventors: Yair Feld, Haifa (IL); Shay Dubi, Tel Aviv (IL)

(73) Assignee: Corassist Cardiovascular Ltd., Herzliya (IL)

( * ) Notice: Subject to any disclaimer, the term of this patent is extended or adjusted under 35 U.S.C. 154(b) by 136 days.

This patent is subject to a terminal disclaimer.

(21) Appl. No.: 11/430,878

(22) Filed: May 10, 2006

(65) Prior Publication Data
US 2006/0276683 A1 Dec. 7, 2006

Related U.S. Application Data

(63) Continuation of application No. 10/353,085, filed on Jan. 29, 2003, now Pat. No. 7,186,210, which is a continuation-in-part of application No. PCT/IL02/00547, filed on Jul. 4, 2002.

(60) Provisional application No. 60/305,205, filed on Jul. 16, 2001, provisional application No. 60/331,338, filed on Nov. 15, 2001.

(51) Int. Cl.
*A61N 1/362* (2006.01)
(52) U.S. Cl. ....................................... 600/16
(58) Field of Classification Search .......... 600/16, 600/37; 623/3.1, 3.16; 607/143–145, 149, 607/152
See application file for complete search history.

(56) References Cited

U.S. PATENT DOCUMENTS

| | | | |
|---|---|---|---|
| 5,263,481 A | | 11/1993 | Axelgaard |
| 5,558,617 A | * | 9/1996 | Heilman et al. ............... 600/16 |
| 5,820,542 A | | 10/1998 | Dobak et al. |
| 5,961,440 A | | 10/1999 | Schweich, Jr. et al. |
| 6,024,096 A | | 2/2000 | Buckberg |

(Continued)

FOREIGN PATENT DOCUMENTS

DE 4314269 A1 11/1994

(Continued)

OTHER PUBLICATIONS

"Chapter 13: Pathophysiology of Heart Failure", Braunwald's Heart Disease: Review and Assessment, third Edition, 1997, Saunders Company Publishers, 12 pages.

(Continued)

*Primary Examiner* — Eric D Bertram
(74) *Attorney, Agent, or Firm* — Nixon & Vanderhye P.C.

(57) ABSTRACT

A method and device featuring at least one component providing a potential to kinetic converted elastic, magnetic repulsion, or, an elastic and magnetic repulsion, pushing, pulling, or, pulling and pushing, type of radially outward expansive force or pressure to an inner, outer, intermediate, and, combination thereof, wall region of the left ventricle, for reducing intraluminal hydrostatic pressure of the left ventricle (LV filling pressure) during the ventricular diastolic stage of the cardiac cycle, thereby, improving diastolic function of the left ventricle of the heart in subjects having a condition of diastolic heart failure (DHF), while minimally disturbing systolic function of the heart. The expansive force or pressure is in a range of about 5-40 mm Hg, whereby, left ventricular end diastolic pressure (LVEDP) is reduced down to the normal range of about 6-12 mm Hg, during ventricular diastole of the heart.

7 Claims, 25 Drawing Sheets

U.S. PATENT DOCUMENTS

| | | | |
|---|---|---|---|
| 6,110,100 | A | 8/2000 | Talpade |
| 6,183,411 | B1 * | 2/2001 | Mortier et al. ............... 600/16 |
| 6,221,104 | B1 | 4/2001 | Buckberg et al. |
| 6,264,602 | B1 | 7/2001 | Mortier et al. |
| 6,695,768 | B1 * | 2/2004 | Levine et al. ............... 600/37 |
| 6,887,192 | B1 | 5/2005 | Whayne et al. |
| 7,124,493 | B2 | 10/2006 | Lau et al. |

FOREIGN PATENT DOCUMENTS

| | | |
|---|---|---|
| IT | PC20000013 A1 | 7/2000 |
| JP | 2001-112796 | 4/2001 |
| WO | WO98/55165 A1 | 12/1998 |
| WO | WO99/53977 A1 | 10/1999 |
| WO | WO01/67985 A1 | 9/2001 |
| WO | WO 01/78625 | 10/2001 |
| WO | WO01/91667 A2 | 12/2001 |
| WO | W002/19917 A1 | 3/2002 |
| WO | WO 03/007778 | 1/2003 |

OTHER PUBLICATIONS

Vasan et al., "Diastolic Heart Failure—No Time to Relax", New England Journal of Medicine, vol. 344, pp. 56-59, Nov. 4, 2001, 5 pages.

Opie, "The Heart Physiology, From Cell to Circulation," $3^{rd}$ Edition, Lippincott-Raven publishers, 1998, Chapter 12, Ventricular Function, pp. 343-389.

Mandinov et al., "Diastolic Heart Failure," Cardiovascular Research, vol. 45, Issue 4, Mar. 2000, pp. 813-825, 20 pages.

Paulus et al., "How to Diagnose Diastolic Heart Failure," European Study Group on Diastolic Heart Failure, European Heart Journal, 1998, vol. 19, pp. 990-1003.

Gandhi et al., "The Pathogenesis of Acute Pulmonary Edema Associated with Hypertension", New England Journal of Medicine, vol. 344:17-22, Jan. 4, 2001, 8 pages.

Sweitzer et al., "Diastolic Heart Failure: Miles to Go Before We Sleep," American Journal of Medicine, vol. 109, Issue 8, Dec. 1, 2000, p. 683-685., 5 pages.

Braunwald, "Heart Failure," Harrison's Principles of Internal Medicine, $14^{th}$ Edition, McGraw Hill Publishers, Chapter 233, pp. 1287-1298.

Grauer, "Heart Failure, Diastolic Dysfunction and the Role of the Family Physician," American Family Physician, Apr. 14, 2001, vol. 63, Issue 8, p. 1483, 4 pages.

Philbin et al., "Systolic Versus Diastolic Heart Failure in Community Practice: Clinical Features, Outcomes, and the use of Angiotensin-Converting Enzyme Inhibitors," American Journal of Medicine, Dec. 1, 2000, vol. 109, pp. 605-613.

Morris-Thurgood et al., "Pacing in Heart Failure: Improved Ventricular Interaction in Diastole Rather than Systolic Re-Synchronization," European Society of Cardiology, Euorpace, 2000, vol. 2, pp. 271-275.

English Translation of JP 2001-112796.

Vasan et al., "Diastolic Heart Failure—No Time to Relax", New England Journal of Medicine, vol. 344, pp. 56-59, Jan. 4, 2001, 5 pages.

Opie, "The Heart Physiology, From Cell to Circulation," 3rd Edition, Lippincott-Raven publishers, 1998, Chapter 12, Ventricular Function, pp. 343-389.

Mandinov et al., "Diastolic Heart Failure," Cardiovascular Research, vol. 45, Issue 4, Mar. 2000, pp. 813-825.

"How to Diagnose Diastolic Heart Failure," European Study Group on Diastolic Heart Failure, European Heart Journal, 1998, vol. 19, pp. 990-1003.

Sweitzer et al., "Diastolic Heart Failure: Miles to Go Before We Sleep," American Journal of Medicine, vol. 109, Issue 8, Dec. 1, 2000, p. 683-685.

Braunwald, "Heart Failure," Harrison's Principles of Internal Medicine, 14th Edition, McGraw Hill Publishers, Chapter 233, pp. 1287-1298.

Grauer, "Heart Failure, Diastolic Dysfunction and the Role of the Family Physician," American Family Physician, Apr. 15, 2001, vol. 63, Issue 8, p. 1483-1486.

Morris-Thurgood et al., "Pacing in Heart Failure: Improved Ventricular Interaction in Diastole Rather than Systolic Re-Synchronization," European Society of Cardiology, Europace, 2000, vol. 2, pp. 271-275.

\* cited by examiner

IN-VIVO METHOD AND DEVICE FOR IMPROVING DIASTOLIC FUNCTION OF THE LEFT VENTRICLE

This application is a continuation of U.S. application Ser. No. 10/353,085, filed Jan. 29, 2003 now U.S. Pat. No. 7,186, 210, which is a continuation-in-part of Application No. PCT/IL02/00547, filed Jul. 4, 2002, which claims priority over U.S. provisional application Ser. No. 60/305,205, filed Jul. 16, 2001 and U.S. provisional application Ser. No. 60/331, 388, filed Nov. 15, 2001.

FIELD AND BACKGROUND OF THE INVENTION

The present invention relates to methods and devices for improving ventricular function of the heart and, more particularly, to an in-vivo method and device for improving diastolic function of the left ventricle of the heart.

Heart failure is commonly defined as the inability of the left ventricle, herein, also referred to as LV, to generate an adequate cardiac output at rest or during exertion, while operating at a normal or enhanced LV filling pressure. Congestive heart failure (CHF) is a clinical syndrome in which heart failure is accompanied by the symptoms and signs of pulmonary and/or peripheral congestion. Heart failure is most commonly associated with impaired LV systolic function. A widely used index for quantifying systolic function is 'ejection fraction' (EF), defined as the ratio of stroke volume to end-diastolic volume, which can be estimated using techniques such as radiocontrast, radionuclide angiography, and/or, echocardiography. The normal value of EF is $0.67\pm0.08$, which is frequently depressed in systolic heart failure even when the stroke volume is normal. A value of $EF\geqq0.50$ is commonly used as an indicator of normal systolic function. It is notable, however, that as much as 30-50% of all patients with typical symptoms of congestive heart failure have a normal or slightly reduced ejection fraction, that is, a value of $EF\geqq0.45$.

In these patients, diastolic dysfunction is implicated as a major contributor of congestive heart failure. In some patients, systolic and diastolic heart failure coexist. The most common form of heart failure, the one caused by coronary arteriosclerosis, is an example of combined systolic and diastolic failure, as described in "Braunwald's Heart Disease: Review and Assessment", third edition, 1997, Saunders Company Publishers. There are about 4.6 million people in the United States with heart failure, and about 550,000 are being reported annually, as indicated by Vasan, R. S., and Benjamin, E. J., in "Diastolic Heart Failure—No Time To Relax", New England Journal of Medicine 2001, 344: 56-59. Also indicated therein, is that the mortality rate from diastolic heart failure (DHF), 5-12% annually, is about four times that among persons without heart failure and half that among patients with systolic heart failure, and that, nonetheless, rates of hospitalization and health care associated with diastolic heart failure rival those associated with systolic heart failure.

Primary diastolic dysfunction is typically observed in patients with hypertension and hypertrophic or restrictive cardiomyopathy, but can also occur in a variety of other clinical disorders and has a particularly high prevalence in the elderly population. Aging is associated with 'physiologic' diastolic dysfunction due to the increase in LV muscle mass and changes in passive elastic properties of the myocardium, hence, the concern of an increase in the incidence of diastolic dysfunction as the aging of the western world population progresses.

For the purpose of clearly understanding, and implementing, the following described preferred embodiments of the present invention, relevant details, description, and, definitions of selected terms, well known to one of ordinary skill in the art, of physiological and pathological aspects, mechanisms, and functions, of the heart, in general, and of the ventricles and atria, in particular, are provided herein. Additional details, description, and, definitions of terms, thereof, are readily available in the scientific literature.

The left ventricle is the chamber on the left side of the heart that receives oxygenated arterial blood from the left atrium and contracts to drive it into the aorta for distribution to the body. The right ventricle is the chamber on the right side of the heart that receives deoxygenated venous blood from the right atrium and drives it into the pulmonary artery in order to receive oxygen from the lungs. Diastole is the normal rhythmically occurring relaxation and dilatation (stretching, expansion, dilation) of the heart cavities (ventricles), during which the cavities are filled with blood. Atrial contraction occurs during the last stage of diastole of the ventricle and aids ventricular filling. Systole is the rhythmic contraction of the heart, especially of the ventricles, by which blood is driven through the aorta and pulmonary artery after each dilation or diastole.

Ventricular filling starts just after mitral valve opening. As the LV pressure decreases below that in the left atrium, the phase of rapid or early filling of the LV accounts for most of ventricular filling. LV filling temporarily stops as pressure in the atrium and left ventricle equalize, commonly known as the phase of diastasis, occurring prior to atrial contraction and during which little blood enters the filled left ventricle. Atrial contraction increases the pressure gradient from the atrium to the left ventricle to renew filling. When the LV fails to relax normally, as in 'LV hypertrophy', increased atrial contraction can enhance late filling. Relaxation (inactivation of contraction) is a dynamic process that begins at the termination of contraction and occurs during isovolumetric relaxation and early ventricular filling. 'Myocardial elasticity' is the change in muscle length for a given change in force. 'Ventricular compliance' is the change in ventricular volume for a given change in pressure, and, 'ventricular stiffness' is the inverse of compliance.

The 'preload' is the load present before contraction has started and is provided by the venous return that fills the ventricle during diastole. The 'Frank Starling law of the heart' states that the larger the volume of the heart, the greater the energy of its contraction and hence the stroke volume is larger. In other words, when the preload increases, the left ventricle distends (widens, expands) and the stroke volume increases, as described by Opie, H. L., in "The Heart Physiology, From Cell To Circulation", third edition, Lippincott-Raven publishers, 1998. The pressure-volume relation curves are an accepted description of the ventricular function.

FIG. 1, adapted from the previously cited "Braunwald's Heart Disease: Review and Assessment" reference, is a schematic diagram illustrating a typical pressure-volume loop of a normal subject (dotted line) and a patient with diastolic dysfunction (solid line); wherein dashed lines, between the letters 'a' and 'b', and, 'c' and 'd', represent the diastolic pressure-volume relation of the normal subject, and, the patient with diastolic dysfunction, respectively. FIG. 1 shows that isolated diastolic dysfunction is characterized by a shift in the pressure-volume loop to the left. Contractile performance is normal, associated with an ejection fraction (EF) value$\geqq$0.45, with a normal or slightly decreased stroke volume. However, LV (left ventricular) pressures throughout diastole are increased, at a common diastolic volume equal to about 70 ml/m². In the patient with diastolic failure, LV end diastolic pressure is about 25 mm Hg, compared with an LV end diastolic pressure of about 5 mm Hg in the normal subject. Thus, diastolic dysfunction increases the modulus of chamber stiffness. A main objective of treating the patient with diastolic dysfunction is to cause the diastolic pressure-volume relation curve (dashed line between 'c' and 'd') to go back to the diastolic pressure-volume relation curve (dashed line between 'a' and 'b', also indicated by the arrow), of the normal subject, by decreasing the end diastolic LV pressure for the same LV volume.

The fundamental problem in diastolic heart failure (DHF) is the inability of the left ventricle to accommodate blood volume during diastole at low filling pressures, as described by Mandinov, L., Eberli, F. R., Seiler, C., and Hess, M. O., in "Diastolic Heart Failure", Cardiovacular Res. 2000, 45: 813-825. Initially, hemodynamic changes may be manifested only in an upward displacement of the diastolic pressure-volume curve in the presence of a normal end-diastolic volume with inappropriate elevation of LV diastolic, left atrial and pulmonocapillary pressure (as previously described above, with reference to FIG. 1). More severe resistance to LV filling may cause inadequate filling even in enhanced diastolic pressure with an additional leftward shift of the diastolic pressure-volume relation, resulting in a decreased end diastolic volume and depressed stroke volume, as described by Mandinov, L., et al.

Currently, four different pathophysiological mechanisms are known and used for understanding and/or explaining diastolic heart failure (DHF), combinations of which may readily take place in a particular patient: (1) slow isovolumic left ventricular relaxation, (2) slow early left ventricular filling, (3) reduced left ventricular diastolic distensibility, and, (4) increased left ventricular chamber stiffness or increased myocardial muscle stiffness, as described in the report, "How To Diagnose Diastolic Heart Failure: European Study Group On Diastolic Heart Failure", European Heart Journal, 1998, 19: 990-1003.

Slow isovolumic left ventricular relaxation, (1), refers to a longer time interval between aortic valve closure and mitral valve opening and a lower negative peak ventricular dP/dt. Regional variation in the onset, rate, and extent of myocardial lengthening is referred to as 'diastolic asynergy', temporal dispersion of relaxation, with some fibers commencing to lengthen later than others, is referred to as 'asynchrony'. Slow early left ventricular filling, (2), is a result of slow myocardial relaxation, segmental incoordination related to coronary artery disease and the atrioventricular pressure gradient. Reduced left ventricular diastolic distensibility, (3), refers to an upward shift of the LV pressure-volume relation on the pressure-volume plot, irrespective of a simultaneous change in slope. Reduction in LV end diastolic distensibility is usually caused by extrinsic compression of the ventricles as in cardiac tamponade. Increased LV chamber stiffness or increased myocardial muscle stiffness, (4), as manifested by a shift to a steeper ventricular pressure-volume curve, is due to processes such as ventricular hypertrophy, endomyocardial fibrosis, disorders with myocardial infiltration (for example, amyloidosis) and replacement of normal, distensible myocardium with non-distensible fibrous scar tissue in healed infarct zones.

The previously cited European Study Group proposed criteria for the diagnosis of DHF. Accordingly, simultaneous presence of the following three criteria is considered obligatory for establishing a diagnosis of DHF: (1) evidence of CHF, (2) normal or mildly abnormal LV systolic function, (3) evidence of abnormal LV relaxation, filling, diastolic distensibility, or, diastolic stiffness.

Pulmonary edema is the result of the increase in pulmocapillary pressure and is due to a shift of liquid from the intravascular compartment to the lung interstitial compartment.

Pulmonary edema is frequently associated with hypertension. Gandhi, S. K. et al. in "The Pathogenesis Of Acute Pulmonary Edema Associated With Hypertension", New England Journal of Medicine, 2001, 344: 17-22, have contradicted the hypothesis that pulmonary edema, apparently associated with hypertension, in patients with preserved ejection fraction, is due to transient systolic dysfunction. They found that the LV ejection fraction and the extent of regional wall motion measured during the acute episode of hypertensive pulmonary edema were similar to those measured after the resolution of the congestion, when the blood pressure was controlled, thus concluding that the pulmonary edema was due to diastolic rather than systolic heart failure.

The management of diastolic heart failure is difficult. There have been no large-scale, randomized controlled trials of therapy in diastolic heart failure, and there remains substantial disagreement about the appropriate therapy for this disease, according to Sweitzer. N. K., and Stevenson, L. W., in "Diastolic heart Failure: Miles To Go Before We Sleep", American Journal of Medicine, 2000, 109: 683-685. Medical therapy of diastolic dysfunction is often empirical and lacks clear-cut pathophysiologic concepts, as indicated in previously cited Mandinov, L. et al. No single drug presently exists which selectively enhances myocardial relaxation without negative effects on LV contractility or pump function, and thus, there is a significant need for a new therapeutic approach for this particular type of heart disease.

Treatment of diastolic heart failure may be logically divided into three areas or categories: (1) removal of the precipitating cause, (2) correction of the underlying cause, and, (3) control of the congestive heart failure state. Treatment goals that have been advocated, by previously cited Mandinov, L. et al., and, by Braunwald, E., in "Heart Failure", Harrison's Principles of Internal Medicine, fourteenth edition, McGraw Hill publishers, are as follows:

1. Reduction of central blood volume. Reduction of salt intake and use of diuretics (usually, loop diuretics). Diuretics are effective in reducing pulmonary congestion, shifting the pressure-volume relation downwards. However, they must be used with care because the volume sensitivity of patients with diastolic dysfunction bears the risk that excessive diuresis may result in a sudden drop in stroke volume. Because of the steep pressure-volume relationship, a small decrease in diastolic volume will cause a large decrease of the filling pressure, and will result in a drop in stroke volume, and thus, in cardiac output.

2. Reduction of workload. Reduction of physical activity, maintenance of emotional rest and use of vasodilators. Vasodilators, such as sodium nitroprusside or ACE inhibitors reduce the filling pressure and the afterload in all patients, and elevate cardiac output. Reduction of an elevated left ventricular end diastolic pressure may improve subendocardial perfusion, thus improving myocardial contraction. Nonetheless, vasodilators have not been useful in the management of isolated diastolic heart failure and are more effective in combined heart failure, as indicated in the previously cited Braunwald, E. text. Vigorous control of hypertension is imperative in patients with heart failure caused by diastolic dysfunction, because control of hypertension may prevent progression or partially reverse the disorder by addressing the primary cause of most cases, as described by Grauner, K., in "Heart Failure, Diastolic Dysfunction And The Role Of The Family Physician", American Family Physician, 2001, 63: 1483-1486.

3. Improvement of LV relaxation. In particular, by using calcium channel blockers or ACE inhibitors. $Ca^{2+}$ channel blockers have been shown to improve myocardial relaxation and enhance diastolic filling. These drugs may be best matched to the pathophysiology of relaxation disturbances due to their ability to decrease cytoplasmic calcium concentration and reduce afterload. However, currently, use of $Ca^{2+}$ channel blockers is limited due to their negative inotropic effects (negative influence on the systolic function of the heart), and clinical trials have not clearly proven them to be beneficial.

4. Regression of LV hypertrophy. In particular, decrease in wall thickness and removal of excess collagen by ACE inhibitors and AT-2 antagonists or Spironolactone. Philbin, E. F., Rocco, T. A., Lindenmuth, N. W., Ulrich, K., and Jenkins, O. L., in "Systolic Versus Diastolic Heart Failure In Community Practice: Clinical Features, Outcomes, And The Use Of ACE Inhibitors", American Journal of Medicine, 2000, 109: 605-613, have shown that the use of ACE inhibitors in patients with ejection fraction equal to or greater than 0.50 was associated with a better NYHA class (New York Heart Association functional and therapeutic classification for stages of heart failure) after discharge from hospitalization, but had no significant effect on mortality or hospital readmission. ACE inhibitors and AT-2 antagonists effect blood pressure, reduce afterload, and effect the myocardium via the local renin-angiotensin system. These effects are important for regression of LV hypertrophy, and improvement of elastic properties of the myocardium.

5. Maintenance of atrial contraction and control of heart rate. In particular, by using beta-blockers and/or antiarrhythmics. Beta-blockers reduce blood pressure and myocardial hypertrophy. The positive effect on diastolic dysfunction is mainly due to slowing of the heart rate and not to a primary improvement in isovolumic relaxation or the diastolic properties of the left ventricle.

6. NO donors. NO (Nitric Oxide) donors have been shown to exert a relaxant effect on the myocardium, which is associated with a decrease in LV end diastolic pressure. In patients with severe LV hypertrophy, an increased susceptibility to NO donors has been documented, which may be beneficial for the prevention of diastolic dysfunction.

7. Heart transplantation. Heart transplantation is a definitive treatment for end stage heart failure.

8. Biventricular pacing. Biventricular pacing improves uncoordinated contraction due to left bundle branch block or other conduction abnormalities with wide 'QRS complex' (P-Q-R-S-T waveform) of an electrocardiogram, which are common in patients with CHF. Morris-Thurgood, J. A., Turner, M. S., Nightingale, A. K., Masani, N., Mumford, C., and, Frenneaux, M. P., in "Pacing In Heart Failure: Improved Ventricular Interaction In Diastole Rather Than Systolic Re-synchronization", Europace 2000, 2: 271-275, have shown that left ventricular pacing acutely benefits congestive heart failure patients with pulmonary capillary wedge pressure greater than 15 mm Hg, irrespective of left bundle branch block. They suggested the beneficial mechanism might be related to an improvement of ventricular interaction in diastole (VID) rather than ventricular systolic re-synchronization. According to their suggestion, LV pacing in patients with high LV end diastolic pressure, will delay right ventricular filling and allow greater LV filling before the onset of VID. Biventricular pacing, however, has not been clinically proven effective in the treatment of patients with diastolic heart failure.

To one of ordinary skill in the art, there is thus a need for, and it would be highly advantageous to have an in-vivo method and device for improving diastolic function of the left ventricle of the heart, while minimally disturbing systolic function of the heart. Moreover, there is a need for such a method and device which is biocompatible and is specially configured for compact and long-term reliable use in humans.

SUMMARY OF THE INVENTION

The present invention relates to an in-vivo method and device for improving diastolic function of the left ventricle of the heart.

Thus, according to the present invention, there is provided an in-vivo method for improving diastolic function of the left ventricle of the heart, comprising the steps of: (a) operatively connecting a device in a rest condition to the left ventricle of the heart, wherein the device includes at least one component featuring physicochemical property and behavior for potentially exerting a radially outward expansive force or pressure to at least one part of wall region of the left ventricle during ventricular diastole; (b) allowing the heart to undergo ventricular systole, during which the potential radially outward expansive force or pressure of the at least one component dynamically increases to a pre-determined magnitude; and (c) allowing the heart to undergo ventricular diastole, during which the pre-determined magnitude of the potential radially outward expansive force or pressure of the at least one component is dynamically converted into a corresponding kinetic radially outward expansive force or pressure applied to the wall region of the left ventricle, for reducing intracardiac hydrostatic pressure during the ventricular diastole, thereby, improving the diastolic function of the left ventricle of the heart.

According to another aspect of the present invention, there is provided an in-vivo device for improving diastolic function of the left ventricle of the heart, comprising: at least one component featuring physicochemical property and behavior for potentially exerting a radially outward expansive force or pressure to at least one part of wall region of the left ventricle during ventricular diastole, whereby: (a) the device is operatively connected in a rest condition to the left ventricle of the heart, (b) the potential radially outward expansive force or pressure of the at least one component dynamically increases to a pre-determined magnitude during ventricular systole of the heart, and (c) the pre-determined magnitude of the potential radially outward expansive force or pressure of the at least one component is dynamically converted into a corresponding kinetic radially outward expansive force or pressure applied to the wall region of the left ventricle during ventricular diastole of the heart, for reducing intracardiac hydrostatic pressure during the ventricular diastole, thereby, improving the diastolic function of the left ventricle of the heart.

The present invention successfully addresses and at the least, minimizes, and, ideally, eliminates, symptoms of diastolic heart failure. The present invention overcomes shortcomings, inadequacies, and, limitations, of currently known and employed techniques for treating diastolic heart failure, by providing an effective, efficient, and, reliable, in-vivo method and device for improving diastolic function of the left ventricle of the heart, while minimally disturbing systolic function of the heart. Moreover, in addition to the present invention primarily applied for treating subjects having symptoms of diastolic heart failure, by reducing intraluminal hydrostatic pressure (LV filling pressure) of the left ventricle during the ventricular diastolic stage of the cardiac cycle, thereby, improving diastolic function of the left ventricle of the heart, while minimally disturbing systolic function of the heart, the present invention can be used in a variety of other cardiac related and/or non-related monitoring applications, such as pressure measurement applications, and, therapeutic applications, such as in drug delivery applications. For example, the method and device of the present invention can be implemented with inclusion and appropriate integration of a procedure and apparatus for time controlled drug delivery or release to the body, in general, and, to the cardiac region, in particular.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 29A shows a device comprising a wire spring that has been bent into a series of v-shaped bends over its entire length. FIG. 29B depicts the embodiment shown in FIG. 29A in its in situ position on the external cardiac wall. FIG. 29C illustrates another wire spring device, in which said spring comprises two v-shaped sections separated by a linear portion. FIG. 29D illustrates the device of FIG. 29C in its in situ position on the external left ventricular wall;

FIG. 32C illustrates the use of two cardiac girdles attached to the surface of the left ventricular wall;

FIG. 33B shows an alternative form of transmural anchor comprising an internal wall-connecting element and an external wall-connecting element. FIG. 33C illustrates an intramural embodiment of the cardiac anchor;

FIG. 34A shows the basic structure of this anchor, while FIG. 34B illustrates the in situ positioning thereof;

DESCRIPTION OF THE PREFERRED EMBODIMENTS

Figure 1:
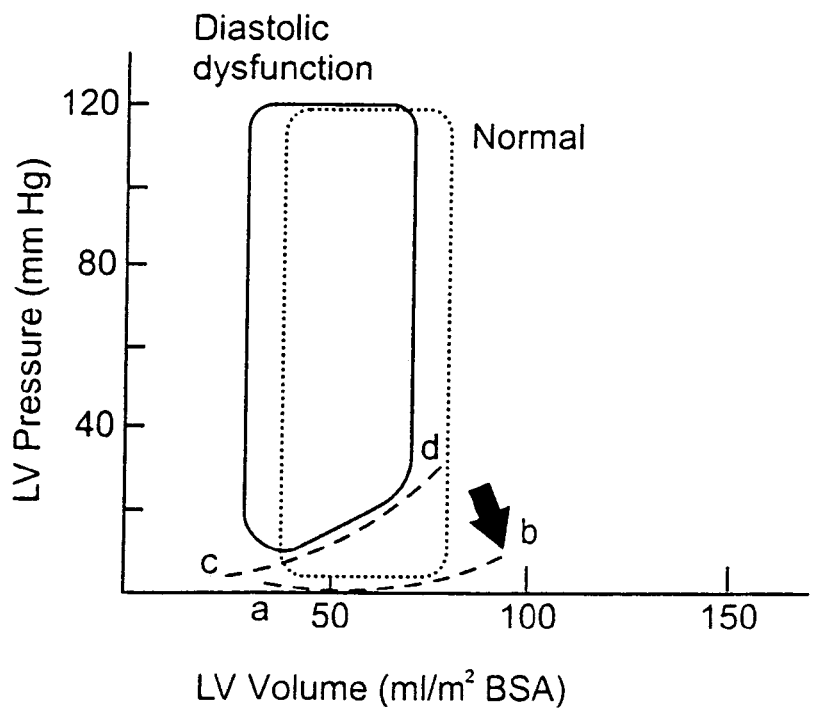
FIG. 1 is a schematic diagram illustrating a typical pressure-volume loop of a normal subject and a patient with diastolic dysfunction.

The present invention relates to an in-vivo method and device for improving diastolic function of the left ventricle of the heart.

Referring again to FIG. 1, a main objective of treating a patient with diastolic dysfunction is to cause the diastolic pressure-volume relation curve (dashed line between 'c' and 'd') to go back to the diastolic pressure-volume relation curve (dashed line between 'a' and 'b', of a normal subject, by decreasing the diastolic LV pressure for the same LV volume, during the entire diastolic stage of the cardiac cycle, in general, and, by decreasing the end diastolic LV pressure for the same LV volume (indicated by the arrow), in particular. The present invention accomplishes this.

The method and device of the present invention are based on uniquely applying a radially outward expansive force or pressure (force per unit area) to the wall region of the left ventricle for reducing intraluminal hydrostatic pressure of the left ventricle, also known as LV filling pressure, during the ventricular diastolic stage of the cardiac cycle, thereby, improving diastolic function of the left ventricle of the heart, while minimally disturbing systolic function of the heart.

Reduction of hydrostatic pressure within the left ventricle has the beneficial effect of reducing hydrostatic pressure in other cardiac compartments and organs preceding, that is, upstream relative to, the left ventricle in the overall cardiac system, in particular, in the left atrium, and in the pulmonary vasculature of the venous system supplying blood to the atrium. These beneficial effects prevent both dilatation of the atria with propagation to atrial fibrillation, and pulmonary congestion causing symptoms of dyspnea and pulmonary edema.

Vectors of the expansive force or pressure, involving pushing, pulling, or, pulling and pushing, applied to the wall of the left ventricle, are directed radially outward, meaning the expansive force or pressure assists in distending the left ventricle during diastole in the cardiac cycle. Normal left ventricular end diastolic pressure (LVEDP) is in the range of about 6-12 mm Hg, and the upper end of this range can increase to above 35 mm Hg during conditions of heart failure involving diastolic dysfunction, as a direct result of the left ventricle needing relatively high hydrostatic filling pressures in order to achieve the necessary left ventricular end diastolic volume (LVEDV) for an appropriate cardiac output. Accordingly, an important objective of the present invention is to significantly reduce the hydrostatic pressure in the left ventricle during the diastolic stage of the cardiac cycle, thereby, improving diastolic function of the left ventricle of the heart, while minimally disturbing systolic function of the heart. In particular, fulfilling this objective includes sufficiently reducing left ventricular end diastolic pressure (LVEDP), preferably, down to the normal range of about 6-12 mm Hg, during ventricular diastole of the heart.

There are several reasons why reducing intraluminal hydrostatic pressure of the left ventricle during the ventricular diastolic stage of the cardiac cycle, thereby, improving diastolic function of the left ventricle of the heart, minimally disturbs systolic function of the heart, in accordance with the present invention.

First, the ventricular device applies a pressure in a range of about 5-20 mm Hg, preferably, about 10 mm Hg. This is a relatively high percentage of diastolic pressure, which is normally 6-12 mm Hg, and, pathologically up to 30-40 mm Hg, and, thus is effective in reducing diastolic hydrostatic pressure, but, it is only a small percentage of systolic pressure, which is normally 120-140 mm Hg, and, pathologically up to 190-200 mm Hg. This means that the systolic work of the heart is only slightly affected in a relatively insignificant manner. For example, in patients with the condition of 'aortic valve stenosis', if the gradient across the valve is about 10 mm Hg (similar to the gradient generated by the ventricular device of the present invention), there is no significant clinical outcome, and, actually no surgical treatment is indicated until the gradient is about 50 mm Hg.

Second, implementation of the present invention causes an increase in left ventricular end diastolic volume (LVEDV) during the heart cycle. Thus, in accordance with the Frank Starling Law of the heart, if the LVEDV is elevated, systolic force of contraction is correspondingly elevated.

Third, if the LVEDV slightly increases, then even if the ejection fraction (EF—ratio of stroke volume to end-diastolic volume) is reduced slightly, the stroke volume is expected to remain the same.

Fourth, in terms of a basic energetic description of the systolic-diastolic heart cycle, a relatively small and limited amount of energy is taken from the total energy (which is usually normal in patients having diastolic heart failure (DHF)) of the systolic movement of the heart. This differential amount of energy is stored as potential energy by the ventricular device (by way of elastic, magnetic, or, elastic and magnetic, mechanisms) and released as kinetic energy during the ventricular diastole. Kinetic release of this differential energy is relatively significant for reducing intraluminal hydrostatic pressure of the left ventricle during the ventricular diastolic stage of the cardiac cycle, thereby, improving diastolic function of the left ventricle of the heart. Essentially, there is transfer of energy from the systolic stage to the diastolic stage of the overall cardiac cycle.

In addition to the present invention primarily applied for treating subjects having symptoms of diastolic heart failure, by reducing intraluminal hydrostatic pressure (LV filling pressure) of the left ventricle during the ventricular diastolic stage of the cardiac cycle, thereby, improving diastolic function of the left ventricle of the heart, while minimally disturbing systolic function of the heart, the present invention can be used in a variety of other cardiac related and/or non-related monitoring applications, such as pressure measurement applications, and, therapeutic applications, such as in drug delivery applications. For example, the method and device of the present invention can be implemented with inclusion and appropriate integration of a procedure and apparatus for time controlled drug delivery or release to the body, in general, and, to the cardiac region, in particular.

It is to be understood that the invention is not limited in its application to the details of the order or sequence of steps of operation or implementation of the method, or, to the details of construction, arrangement, and composition of the components of the device, set forth in the following description and accompanying drawings. For example, the following description refers specifically to an in-vivo method and device for improving diastolic function of the left ventricle of the heart. However, it should be clear to one of ordinary skill in the art and field of cardiac principles and applications, that the present invention is readily applicable to improving diastolic function of other components of the heart, in general, and of the right ventricle, in particular. For example, the following description refers to specific exemplar geometries, shapes, and forms, and, specific exemplary dimensions and ranges, thereof, of construction of the elastic or resilient components, and, the magnetic components, of the device, in order to illustrate implementation of the present invention. The invention is capable of other embodiments or of being practiced or carried out in various ways.

Also, it is to be understood that the phraseology and terminology employed herein are for the purpose of description and should not be regarded as limiting. For example, in describing the present invention, the key functionality terms 'elasticity' and 'resiliency', and, the corresponding variant terms 'elastic' and 'resilient', are considered synonyms, and for the purpose of brevity, while maintaining clarity of description, the terms 'elasticity' and 'elastic', are solely used hereinafter, however, it is to be fully understood that the corresponding synonymous terms 'resiliency' and 'resilient', respectively, are equally applicable.

Steps, components, operation, and implementation of an in-vivo method and device for improving diastolic function of the left ventricle of the heart according to the present invention are better understood with reference to the following description and accompanying drawings. Throughout the following description and accompanying drawings, like reference numbers refer to like elements. Herein, there is provided a sequence of steps of operation and implementation of an overall general method and corresponding general device which are generally applicable to various specific cases and embodiments of each of the three principle preferred embodiments, described herein.

In the first principle preferred embodiment of the method and device of the present invention, there is uniquely utilizing the physicochemical property and behavior of elasticity or resiliency, in a relatively simple manner, in appropriately constructed and configured elastic or resilient components of the device operatively connected to a wall region of the left ventricle, for exerting an elastic or resilient type of the expansive force or pressure to the wall region of the left ventricle, for reducing intracardiac hydrostatic pressure during ventricular diastole of the heart, thereby, improving diastolic function of the left ventricle of the heart, while minimally disturbing systolic function of the heart.

In the second principle preferred embodiment of the method and device of the present invention, there is uniquely utilizing the physicochemical property and behavior of magnetic repulsion, in a relatively simple manner, in appropriately constructed and configured magnetic components of the device operatively connected to a wall region of the left ventricle, for exerting a magnetic repulsion type of the expansive force or pressure to a wall region of the left ventricle, for reducing intracardiac hydrostatic pressure during ventricular diastole of the heart, thereby, improving diastolic function of the left ventricle of the heart, while minimally disturbing systolic function of the heart.

In the third principle preferred embodiment of the method and device of the present invention, there is uniquely utilizing the physicochemical properties and behaviors of both elasticity or resiliency and magnetic repulsion, in a relatively simple manner, in appropriately constructed and configured elastic or resilient components and magnetic components of the device operatively connected to a wall region of the left ventricle, for exerting both elastic or resilient and magnetic repulsion types of the expansive force or pressure to a wall region of the left ventricle, for reducing intracardiac hydrostatic pressure during ventricular diastole of the heart, thereby, improving diastolic function of the left ventricle of the heart, while minimally disturbing systolic function of the heart.

In Step (a) of the method of the present invention, there is operatively connecting a device, herein, generally referred to as a ventricular device, in a rest condition to the left ventricle of the heart, where the ventricular device includes at least one component featuring physicochemical property and behavior for potentially exerting a radially outward expansive force or pressure to at least one part of wall region of the left ventricle during ventricular diastole.

Step (a) is generally applicable to each of the three principle preferred embodiments of the present invention, that is, the first principle preferred embodiment based on the physicochemical property and behavior of elasticity or resiliency, the second principle preferred embodiment based on the physicochemical property and behavior of magnetism, and, the third principle preferred embodiment based on the physicochemical properties and behaviors of both elasticity or resiliency and magnetism, and, is generally applicable to exemplary alternative embodiments thereof. Each principle preferred embodiment of the present invention is separately described and illustrated in detail herein below.

In the first principle preferred embodiment of the method and device, in general, the ventricular device includes at least one component featuring the physicochemical property and behavior of elasticity, whereby, the at least one elastic component of the ventricular device is positioned adjacent to at least one part of wall region of the left ventricle, and potentially exerts a radially outward, elastic, pushing, pulling, or, pulling and pushing, type of the expansive force or pressure to the wall region of the left ventricle, for reducing intracardiac hydrostatic pressure during ventricular diastole of the heart, thereby, improving diastolic function of the left ventricle of the heart, while minimally disturbing systolic function of the heart.

For this embodiment, the wall region of the left ventricle is selected from the group consisting of inner wall surface of the left ventricle, outer wall surface of the left ventricle, intermediate wall region of the left ventricle, and, combinations of wall regions of the left ventricle thereof. Inner wall surface of the left ventricle refers to ventricular wall surface facing inside the cavity of the left ventricle. Outer wall surface of the left ventricle refers to ventricular wall surface facing outside of the left ventricle. Intermediate wall region refers to ventricular wall region intermediate to, or in between, the inner wall surface of the left ventricle and the outer wall surface of the left ventricle. Alternatively stated, but of equal meaning, intermediate wall region refers to ventricular wall region 'inside' the wall of the left ventricle. For the wall region of the left ventricle, used for the adjacent positioning of the at least one elastic component, being a combination of wall regions, a first exemplary combination is the intermediate wall region of the left ventricle and the inner wall surface of the left ventricle, and, a second exemplary combination is the outer wall surface of the left ventricle and the intermediate wall region of the left ventricle. It is clear to one skilled in the art that there are several additional combinations of the wall region of the left ventricle, which can be used for the adjacent positioning of the at least one elastic component of the ventricular device.

In a first specific case, herein, referred to as specific case (a), of the first principle preferred embodiment of the method and device, the ventricular device includes at least one component featuring the physicochemical property and behavior of elasticity, whereby, the at least one elastic component of the ventricular device is positioned adjacent to at least one part of inner wall surface of the left ventricle, and potentially exerts a radially outward, elastic, pushing type of the expansive force or pressure to the inner wall surface of the left ventricle, for reducing intracardiac hydrostatic pressure during ventricular diastole of the heart, thereby, improving diastolic function of the left ventricle of the heart, while minimally disturbing systolic function of the heart.

In a second specific case, herein, referred to as case (b), of the first principle preferred embodiment of the method and device, the ventricular device includes at least one component featuring the physicochemical property and behavior of elasticity, whereby, the at least one elastic component of the ventricular device is positioned adjacent to at least one part of outer wall surface of the left ventricle, and potentially exerts a radially outward, elastic, pulling type of the expansive force or pressure to the outer wall surface of the left ventricle, for reducing intracardiac hydrostatic pressure during ventricular diastole of the heart, thereby, improving diastolic function of the left ventricle of the heart, while minimally disturbing systolic function of the heart.

In a third specific case, herein, referred to as case (c), of the first principle preferred embodiment of the method and device, the ventricular device includes at least one component featuring the physicochemical property and behavior of elasticity, whereby, the at least one elastic component of the ventricular device is positioned adjacent to at least one part of intermediate wall region of the left ventricle, and potentially exerts a radially outward, elastic, pulling and pushing type of the expansive force or pressure to the intermediate wall region of the left ventricle, for reducing intracardiac hydrostatic pressure during ventricular diastole of the heart, thereby, improving diastolic function of the left ventricle of the heart, while minimally disturbing systolic function of the heart.

In a fourth specific case, herein, referred to as case (d), of the first principle preferred embodiment of the method and device, the ventricular device includes at least one component featuring the physicochemical property and behavior of elasticity, whereby, the at least one elastic component of the ventricular device is positioned adjacent to at least one part of intermediate wall region of the left ventricle, and potentially exerts a radially outward, elastic, pulling and pushing type of the expansive force or pressure to the intermediate wall region of the left ventricle, and, is positioned adjacent to at least one part of inner wall surface of the left ventricle, and potentially exerts a radially outward, elastic, pushing type of the expansive force or pressure to the inner wall surface of the left ventricle, for reducing intracardiac hydrostatic pressure during ventricular diastole of the heart, thereby, improving diastolic function of the left ventricle of the heart, while minimally disturbing systolic function of the heart.

In the first principle preferred embodiment of the method and device, generally applicable to each specific case (a)-(d), the ventricular device is preferably designed, configured, and constructed, in a manner selected from the group consisting of: as an integral single elastic component, as an integral single complex of a plurality of elastic components, as a non-integral elastic component, as a non-integral complex of a plurality of elastic components, and combinations thereof. For example, as an integral single, continuous, elastic component, the ventricular device may be designed, configured, and constructed, by starting with a single, unitary, preferably, metal, tube, followed by removing, for example, by laser cutting, selected material from the tube, until only the desired geometry, shape, and dimensions, remain.

The ventricular device of each specific case (a)-(d), in general, and, the at least one elastic component, in particular, are constructed from a single type of material, or, from a plurality of different types of materials. More specifically, the ventricular device, in general, and, the at least one elastic component, in particular, are constructed from a single type of material, or, from a plurality of different types of materials, exhibiting the physicochemical property and behavior of elasticity, whereby the device, in general, and, the at least one elastic component, in particular, are self-expandable. For example, such material is selected from the group consisting of a pure metal, a metal alloy, and, combinations thereof. Exemplary pure metals are tungsten, platinum, and, titanium. Exemplary metal alloys are nitinol, and, stainless steel.

The ventricular device of each specific case (a)-(d), in general, and, the at least one elastic component, in particular, have variable geometry, shape, form, and, dimensions, which are specifically determined, in part, according to actual or measured dynamical (variable) geometry, shape, form, and, dimensions of an actual functioning heart, in general, and, of an actual functioning left ventricle, in particular.

The variable geometry, shape, and, form, of the ventricular device of each specific case (a)-(d), in general, and, the at least one elastic component, in particular, are characterized by at least one physical aspect or descriptor selected from the group consisting of linear, straight, non-linear, curved, curvilinear, angular, planar, non-planar, branched, thick, coarse, thin, fine, long, short, and, combinations thereof.

The variable geometry, shape, and, form, of the ventricular device of each specific case (a)-(d), in general, and, the at least one elastic component, in particular, are characterized by at least one physical aspect or descriptor selected from the group consisting of circular, disc, conical, spherical, spheroidal, elliptical, ellipsoidal, parabolic, parabaloidal, hyperbolic, hyperpoloidal, spiral, helical, polygonal such as triangular, square, and, rectangular, and, combinations thereof.

The variable geometry, shape, and, form, of the ventricular device of each specific case (a)-(d), in general, and, the at least one elastic component, in particular, are characterized by at least one physical aspect or descriptor selected from the group consisting of integral, non-integral, continuous, discontinuous or non-continuous, contiguous, discontiguous or non-contiguous, and, combinations thereof.

The variable geometry, shape, and, form, of the ventricular device of each specific case (a)-(d), in general, and, the at least one elastic component, in particular, are characterized by at least one physical aspect or descriptor selected from the group consisting of a variable extent or degree of symmetry, a variable extent or degree of asymmetry, and, combinations thereof.

Surfaces and volumes of the variable geometry, shape, and, form, of the ventricular device of each specific case (a)-(d), in general, and, the at least one elastic component, in particular, are characterized by at least one physical aspect or descriptor selected from the group consisting of smooth, flat, rough, ridged or bumpy, jagged, wavy, saw-toothed, bent, planar, non-planar, closed, open, completely solid featuring no cut-out or hollow pattern, incompletely solid featuring a cut-out or hollow pattern such as a cellular, net, or beehive, type of cut-out or hollow pattern, and, combinations thereof.

Furthermore, the ventricular device of each specific case (a)-(d), in general, and, the at least one elastic component, in particular, have dimensions of length, height, and, width, depth, or thickness, each on the order of microns to centimeters, in the range of between about 10 microns to about 8 cm.

Additionally, in the first principle preferred embodiment of the method and device, generally applicable to each specific case (a)-(d), the variable geometry, shape, form, and, dimensions, and, elastic strength, of the ventricular device, in general, and, the at least one elastic component, in particular, are also specifically determined, in part, according to the desired or necessary extent or degree of elasticity, for properly and optimally performing the critical function of potentially exerting a radially outward, elastic, pushing, pulling, or, pulling and pushing, type of the expansive force or pressure (in a range of about 5-20 mm Hg, preferably, about 10 mm Hg) to the inner wall surface, to the outer wall surface, to the intermediate wall region, or, to a combination of wall regions thereof, of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

In alternative embodiments of the first principle preferred embodiment of the method and device, generally applicable to each specific case (a)-(d), the ventricular device, further includes at least one non-elastic component or mechanism, which operatively functions together with other elements or components of the ventricular device for optimally effecting the elastic functionality of the ventricular device, while minimally disturbing systolic function of the heart.

For example, for implementing Step (a) of operatively connecting the ventricular device in a rest condition to the left ventricle of the heart, the ventricular device, in general, including the at least one elastic component, in particular, further includes at least one non-elastic component or mechanism for anchoring, adhering, and/or, attaching, at least one part or region of the ventricular device, in general, and, the at least one elastic component, in particular, to at least one part of wall region of the left ventricle where the ventricular device is configured for in-vivo elastic operation.

The anchoring, adhering, and/or, attaching, component or mechanism is constructed from a single type of material, or, from a plurality of different types of materials, having variable geometry, shape, form, and, dimensions. More specifically, the anchoring, adhering, and/or, attaching, component or mechanism is constructed from a single type of material, or, from a plurality of different types of materials, having variable geometry, shape, form, and, dimensions, exhibiting (i) physicochemical properties and behavior selected from the group consisting of anchoring, adhering, attaching, and, combinations thereof, and, exhibiting (ii) physicochemical properties and behavior which are (1) non-interfering, additive, or, synergistic, with the elastic functionality of the ventricular device during in-vivo operation in the heart, (2) minimally disturbing to the overall functionality of the heart during the cardiac cycle, and, (3) biocompatible.

An exemplary anchoring, adhering, and/or, attaching, component or mechanism is selected from the group consisting of biocompatible pins, biocompatible needles, biocompatible spikes, biocompatible screws, biocompatible clamps, biocompatible glue, biocompatible adhesion, surgical sutures, and, combinations thereof, having dimensions of length, height, and, width, depth, or thickness, each on the order of microns to centimeters, in the range of between about 10 microns to about 8 cm.

Figure 15:
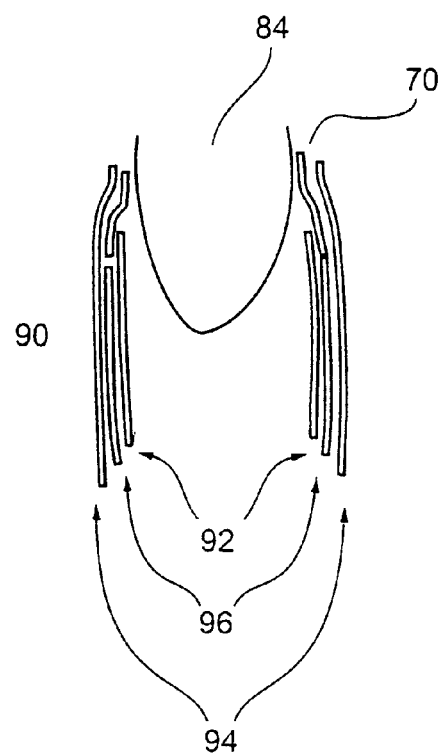
FIG. 15 is a schematic diagram illustrating an example of a thoracoscopic delivery system, for implementing specific case (b) of the first principle preferred embodiment of the method, of positioning the at least one elastic component of the ventricular device adjacent to the outer wall surface of the left ventricle, in accordance with the present invention.
Figure 16:
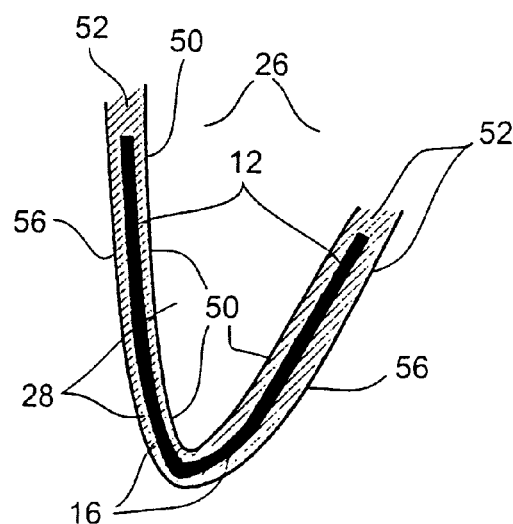
FIG. 16 is a schematic diagram illustrating a cross sectional view of the exemplary 'U' shaped ventricular device of FIG. 3A, for implementing specific case (c) of the first principle preferred embodiment of the method, of positioning the at least one elastic component of the ventricular device adjacent to the intermediate wall region of the left ventricle, in accordance with the present invention.
Figure 17:
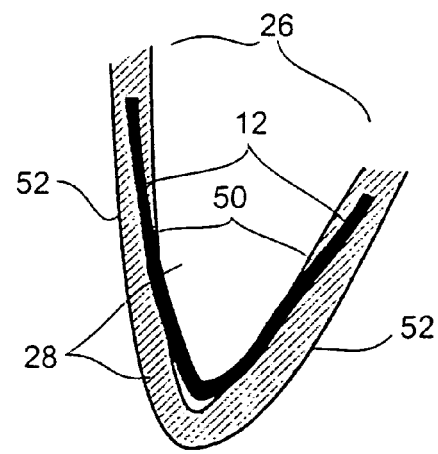
FIG. 17 is a schematic diagram illustrating a cross sectional view of the exemplary 'U' shaped ventricular device of FIG. 3A, for implementing specific case (d) of the first principle preferred embodiment of the method, of positioning the at least one elastic component of the ventricular device adjacent to the intermediate wall region of the left ventricle, and, adjacent to the inner wall surface of the left ventricle, in accordance with the present invention.

Following are description and accompanying drawings for describing and illustrating, respectively, various examples of alternative embodiments of the previously indicated four specific cases (a)-(d), of the first principle preferred embodiment of the method and device. FIGS. 2A-11 are used for illustrating specific case (a), relating to positioning the at least one elastic component of the ventricular device adjacent to the inner wall surface of the left ventricle. FIGS. 12-15 are used for illustrating specific case (b), relating to positioning the at least one elastic component of the ventricular device adjacent to the outer wall surface of the left ventricle. FIG. 16 is used for illustrating specific case (c), relating to positioning the at least one elastic component of the ventricular device adjacent to the intermediate wall region of the left ventricle. FIG. 17 is used for illustrating specific case (d), relating to positioning the at least one elastic component of the ventricular device adjacent to the intermediate wall region of the left ventricle, and, adjacent to the inner wall surface of the left ventricle. In some of these figures, the ventricular device, including the at least one elastic component, is drawn as symmetric, in a non-limiting fashion, for illustrative and exemplary purposes. However, as previously indicated above, the variable geometry, shape, and, form, of the ventricular device of each specific case (a)-(d), in general, and, the at least one elastic component, in particular, are characterized by at least one physical aspect or descriptor selected from the group consisting of a variable extent or degree of symmetry, a variable extent or degree of asymmetry, and combinations thereof.

Figure 2A:
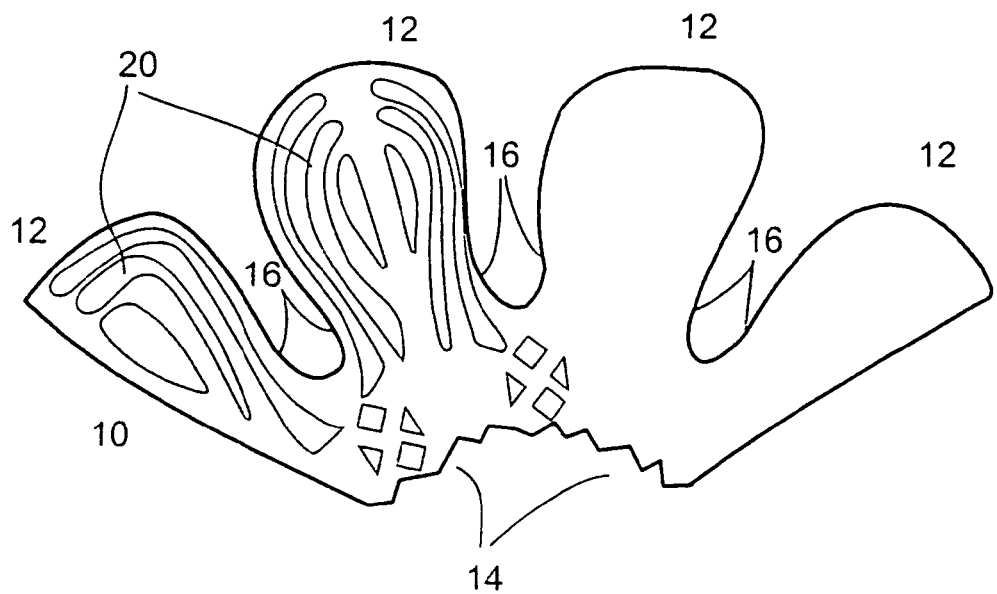
FIGS. 2A and 2B are schematic diagrams illustrating a two-dimensional planar view, and, a perspective view, respectively, of a first general type of exemplary ventricular device for implementing specific case (a) of the first principle preferred embodiment of the method, of positioning the at least one elastic component of the ventricular device adjacent to the inner wall surface of the left ventricle, in accordance with the present invention.
Figure 2B:
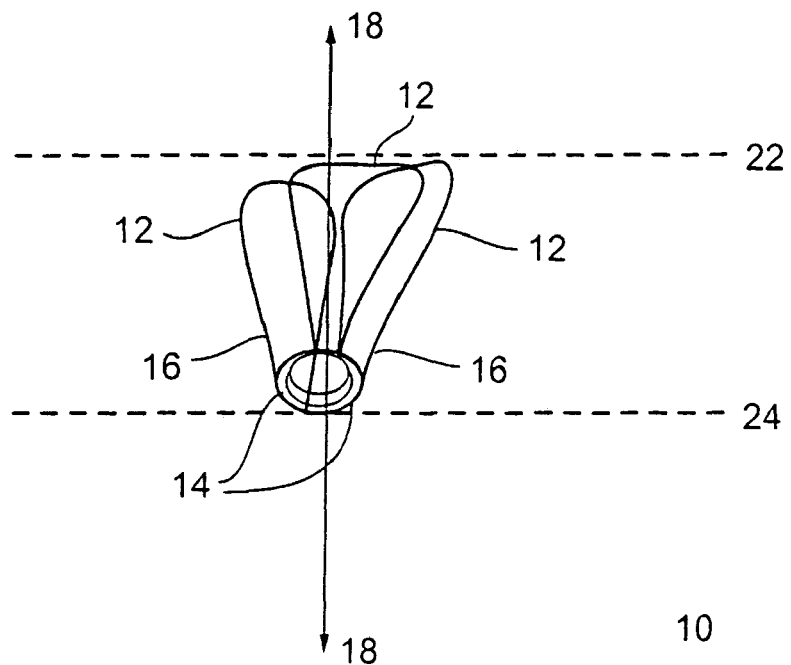

Referring again to the drawings, FIGS. 2A and 2B are schematic diagrams illustrating a two-dimensional planar view, and, a perspective view, respectively, of a first general type of exemplary ventricular device, generally referred to as ventricular device 10, for implementing specific case (a) of the first principle preferred embodiment of the method and device, of positioning the at least one elastic component of the ventricular device adjacent to the inner wall surface of the left ventricle. In FIGS. 2A and 2B, ventricular device 10 is illustrated in a 'rest' position, that is, in a position whereby ventricular device 10 potentially applies a radially outward, elastic, pushing type of the expansive force or pressure to the inner wall surface of the left ventricle.

In this first general type of exemplary embodiment, ventricular device 10 is designed, configured, and constructed, as an integral single elastic component, herein, also referred to as elastic component 10, featuring a plurality of, for example, three, elastic arms or extensions 12, optionally, longitudinally and radially extending from, for example, a single optional elastic lower basal section or ring formation 14. Lower end regions 16 of elastic arms or extensions 12 of ventricular device or elastic component 10 are integral and continuous with each other, by way of optional elastic lower basal section or ring formation 14. Ventricular device or elastic component 10 is actually of conical geometry, shape, and, form, as particularly shown in FIG. 2B, relative to central longitudinal axis 18, and, elastic arms or extensions 12 are clover or bulb shaped. FIG. 2A particularly illustrates elastic arms or extensions 12 as clover or bulb shaped having a generally symmetrical incomplete solid cut-out or hollow pattern 20. Elastic arms or extensions 12 provide ventricular device or elastic component 10 with the conical geometry, shape, and, form, and are configured to compactly fit into the left ventricle, with optional elastic lower basal section or ring formation 14 configured or connected, preferably, to the cardiac left ventricle apex. In FIGS. 2A and 2B, optional elastic lower basal section or ring formation 14 is preferably self-expanding, whereby ventricular device 10 is inserted into place by using a minimally invasive surgical procedure, such as catheterization, thoracoscopy, or, thoracotomy, with a relatively small diameter delivery system (not shown) for delivering and deploying ventricular device 10 into the body, in general, and to a left ventricular cardiac inner wall surface, in particular.

Exemplary dimensions of ventricular device or elastic component 10 are as follows. Longitudinal length, that is, the length extending along central longitudinal axis 18 from the top of elastic arms or extensions 12 to the bottom of optional elastic lower basal section or ring formation 14, is in the range of between about 0.5 cm to about 10.0 cm, preferably, about 4 cm. Diameter across the widest end, that is, the distance extending along plane 22 spanning across the top or free ends of elastic arms or extensions 12, is in the range of between about 0.1 cm to about 6.0 cm, preferably, about 3 cm. Diameter across the narrowest end, that is, the distance extending along plane 24 spanning across optional elastic lower basal section or ring formation 14, is in the range of between about 0.05 cm to about 3.0 cm, preferably, about 0.8 cm. General depth or thickness of the material of ventricular device or elastic component 10 is in the range of between about 0.01 mm (10 microns) to about 5.0 mm (5000 microns), preferably, about 0.3 mm (300 microns).

In alternative embodiments, ventricular device or elastic component 10, shown in FIGS. 2A and 2B, features another number, such as one, two, or, more than three, of elastic arms or extensions 12, integral and continuous, and/or, non-integral and non-continuous, with each other, by way of a single optional elastic lower basal section or ring formation 14, or, by way of a plurality of optional elastic lower basal sections or ring formations 14, or, without the presence of any optional elastic lower basal section or ring formation 14. Furthermore, in alternative embodiments, elastic arms or extensions 12, and, optional elastic lower basal section or ring formation 14, have variable geometry, shape, form, and, dimensions, and, elastic strength, which, as previously indicated above, are specifically determined, in part, according to actual or measured dynamical (variable) geometry, shape, form, and, dimensions of an actual heart, in general, and, of an actual left ventricle, in particular, and, are also specifically determined, in part, according to the desired or necessary extent or degree of elasticity, for properly and optimally performing the critical function of potentially exerting a radially outward, elastic, pushing type of the expansive force or pressure (in a range of about 5-20 mm Hg, preferably, about 10 mm Hg) to the inner wall surface of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

Specifically, for example, each of one, two, or all three, elastic arms or extensions 12 of ventricular device or elastic component 10, shown in FIGS. 2A and 2B, has longitudinal length of about 2 cm, instead of about 4 cm, whereby shorter elastic arms or extensions 12 can be compactly configured and positioned inside the left ventricle for maximizing contact with the inner wall surface of the left ventricle, without contacting and/or interfering with the papillary muscles and the chordae tendinea. Specifically, for example, optional elastic lower basal section or ring formation 14, is designed, configured, and constructed, as a complete solid featuring no cut-out or hollow pattern, or, as an incomplete solid featuring a cut-out or hollow pattern, such as cells having variable geometry, shape, form, and, dimensions, for optimizing the elastic functionality.

A few of the many possible alternative embodiments of the first general type of exemplary ventricular device, ventricular device 10, are illustrated in FIGS. 3A-5B.

Figure 3A:
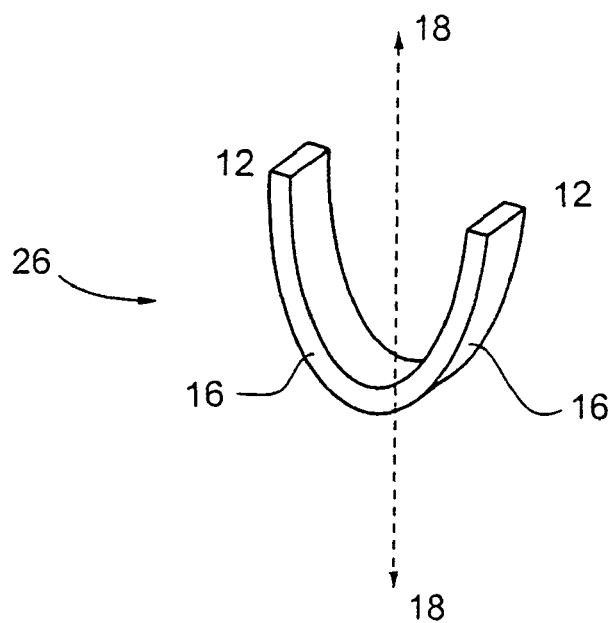
FIG. 3A is a schematic diagram illustrating a perspective view of an exemplary 'U' shaped ventricular device, featuring two elastic arms or extensions, for implementing specific case (a) of the first principle preferred embodiment of the method, of positioning the at least one elastic component of the ventricular device adjacent to the inner wall surface of the left ventricle, in accordance with the present invention.

FIG. 3A is a schematic diagram illustrating a perspective view of an exemplary 'U' shaped ventricular device 26 for implementing specific case (a) of the first principle preferred embodiment of the method and device, of positioning the at least one elastic component of the ventricular device adjacent to the inner wall surface of the left ventricle. Ventricular device 26 is designed, configured, and constructed, as an integral single, continuous, elastic component, featuring a plurality of two elastic arms or extensions 12 which are essentially of the same geometry, shape, and dimensions, and, are either symmetric or asymmetric relative to central longitudinal axis 18. Lower end regions 16 of elastic arms or extensions 12 of ventricular device 26 are integral and continuous with each other without the presence of optional elastic lower basal section or ring formation (14 in FIGS. 2A and 2B).

Figure 3B:
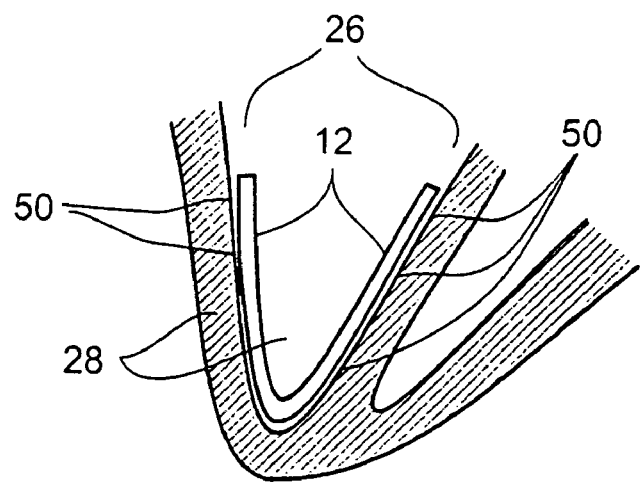
FIG. 3B is a schematic diagram illustrating a cross sectional view of an exemplary rest position of the exemplary 'U' shaped ventricular device of FIG. 3A, inside the left ventricle, for implementing specific case (a) of the first principle preferred embodiment of the method, of positioning the at least one elastic component of the ventricular device adjacent to the inner wall surface of the left ventricle, in accordance with the present invention.

FIG. 3B is a schematic diagram illustrating a cross sectional view of an exemplary rest position of exemplary 'U' shaped ventricular device 26 of FIG. 3A, featuring the plurality of two elastic arms or extensions 12 positioned adjacent to inner wall surface 50 of left ventricle 28. Many alternative specific embodiments of exemplary 'U' shaped ventricular device 26, consistent with the function/structure description of exemplary ventricular device 10 (FIGS. 2A and 2B), above, are clearly possible, for implementing specific case (a) of the first principle preferred embodiment of the method and device, of positioning the at least one elastic component of the ventricular device adjacent to the inner wall surface of the left ventricle.

Figure 4A:
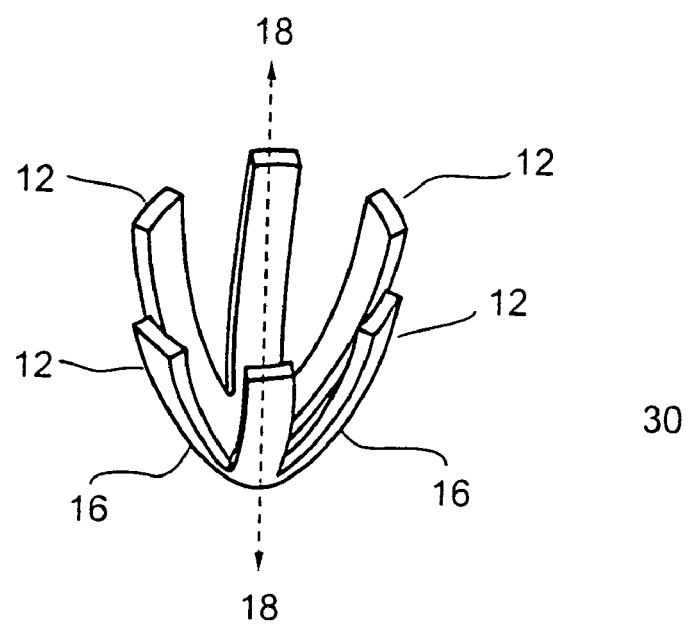
FIG. 4A is a schematic diagram illustrating a perspective view of another exemplary 'U' shaped ventricular device, featuring six elastic arms or extensions without an optional elastic lower basal section or ring formation, for implementing specific case (a) of the first principle preferred embodiment of the method, of positioning the at least one elastic component of the ventricular device adjacent to the inner wall surface of the left ventricle, in accordance with the present invention.

FIG. 4A is a schematic diagram illustrating a perspective view of another exemplary 'U' shaped ventricular device 30 for implementing specific case (a) of the first principle preferred embodiment of the method and device, of positioning the at least one elastic component of the ventricular device adjacent to the inner wall surface of the left ventricle. Ventricular device 30 is designed, configured, and constructed, as an integral single, continuous, elastic component, featuring a plurality of six elastic arms or extensions 12 which are essentially of the same geometry, shape, form, and, dimensions, and, are symmetric relative to central longitudinal axis 18. Lower end regions 16 of elastic arms or extensions 12 of ventricular device 30 are integral and continuous with each other without the presence of an optional elastic lower basal section or ring formation (14 in FIGS. 2A and 2B).

Figure 4B:
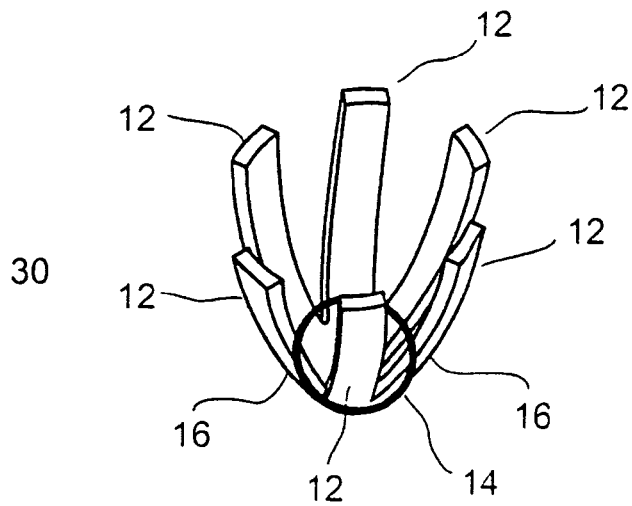
FIG. 4B is a schematic diagram illustrating a perspective view of exemplary 'U' shaped ventricular device of FIG. 4A, with a single optional elastic lower basal section or ring formation, for implementing specific case (a) of the first principle preferred embodiment of the method, of positioning the at least one elastic component of the ventricular device adjacent to the inner wall surface of the left ventricle, in accordance with the present invention.

FIG. 4B is a schematic diagram illustrating a perspective view of exemplary 'U' shaped ventricular device 30 of FIG. 4A, whereby lower end regions 16 of elastic arms or extensions 12 are integral and continuous with each other by way of a single optional elastic lower basal section or ring formation 14. Many alternative specific embodiments of exemplary 'U' shaped ventricular device 30, consistent with the function/structure description of exemplary ventricular device 10 (FIGS. 2A and 2B), above, are clearly possible, for implementing specific case (a) of the first principle preferred embodiment of the method and device, of positioning the at least one elastic component of the ventricular device adjacent to the inner wall surface of the left ventricle.

Figure 5A:
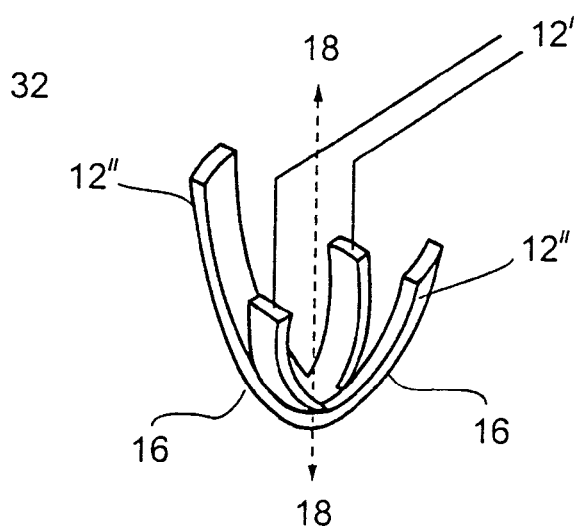
FIG. 5A is a schematic diagram illustrating a perspective view of another exemplary 'U' shaped ventricular device, featuring elastic arms or extensions of different longitudinal length without an optional elastic lower basal section or ring formation, for implementing specific case (a) of the first principle preferred embodiment of the method, of positioning the at least one elastic component of the ventricular device adjacent to the inner wall surface of the left ventricle, in accordance with the present invention.
Figure 5B:
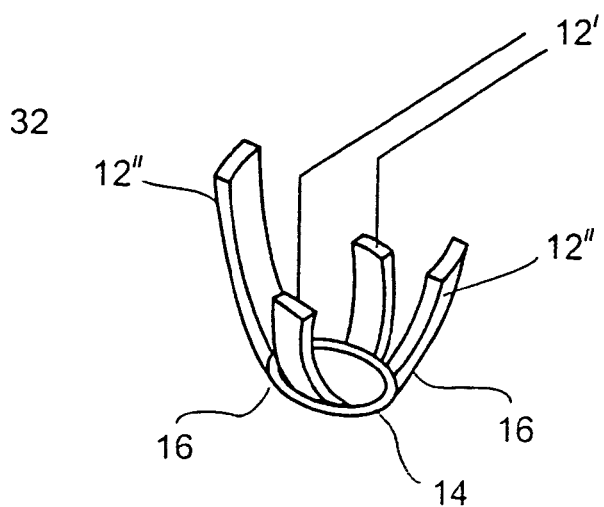
FIG. 5B is a schematic diagram illustrating a perspective view of exemplary 'U' shaped ventricular device of FIG. 5A, with a single optional elastic lower basal section or ring formation, for implementing specific case (a) of the first principle preferred embodiment of the method, of positioning the at least one elastic component of the ventricular device adjacent to the inner wall surface of the left ventricle, in accordance with the present invention.

FIG. 5A is a schematic diagram illustrating a perspective view of another exemplary 'U' shaped ventricular device 32 for implementing specific case (a) of the first principle preferred embodiment of the method and device, of positioning the at least one elastic component of the ventricular device adjacent to the inner wall surface of the left ventricle. Ventricular device 32 is designed, configured, and constructed, as an integral single, continuous, elastic component, featuring a plurality of four elastic arms or extensions 12' and 12", including two short elastic arms or extensions 12' and two long elastic arms or extensions 12", which are essentially of the same geometry, shape, form, and, dimensions (except for the difference in the longitudinal length), and are symmetric relative to central longitudinal axis 18. Lower end regions 16 of elastic arms or extensions 12' and 12" of ventricular device 32 are integral and continuous with each other without the presence of an optional elastic lower basal section or ring formation (14 in FIGS. 2A and 2B). FIG. 5B is a schematic diagram illustrating a perspective view of exemplary 'U' shaped ventricular device 32 of FIG. 5A, whereby lower end regions 16 of elastic arms or extensions 12' and 12" are integral and continuous with each other by way of a single optional elastic lower basal section or ring formation 14.

Consistent with the function/structure description of alternative embodiments of exemplary ventricular device 10 (FIGS. 2A and 2B), above, for exemplary 'U' shaped ventricular device 32, each of the two short elastic arms or extensions 12' has a longitudinal length of, for example, about 2 cm, and, each of the two long elastic arms or extensions 12" has a longitudinal length of, for example, about 4 cm. Such an exemplary configuration of ventricular device 10 is compactly configured and positioned inside the left ventricle for maximizing contact with the inner wall surface of the left ventricle, without contacting and/or interfering with the papillary muscles and the chordae tendinea. Specifically, short elastic arms or extensions 12' are configured and positioned below the papillary muscles whereas long elastic arms or extensions 12" are configured and positioned between the papillary muscles, without contacting the chordae tendinea. Many alternative specific embodiments of exemplary 'U' shaped ventricular device 32, consistent with the function/structure description of exemplary ventricular device 10 (FIGS. 2A and 2B), above, are clearly possible, for implementing specific case (a) of the first principle preferred embodiment of the method and device, of positioning the at least one elastic component of the ventricular device adjacent to the inner wall surface of the left ventricle.

As previously described above, in alternative embodiments, elastic arms or extensions 12 of exemplary device 10 (FIGS. 2A and 2B), for implementing specific case (a) of the first principle preferred embodiment of the method and device, of positioning the at least one elastic component of the ventricular device adjacent to the inner wall surface of the left ventricle, have variable geometry, shape, form, and, dimensions. Several of the many possible alternative embodiments of elastic arms or extensions 12 of the first general type of exemplary ventricular device, ventricular device 10, are illustrated in FIGS. 6A-6I, 7A-7E, 8A-8C, and 9. In some of these figures, elastic arms or extensions 12 are drawn as symmetric, in a non-limiting fashion, for illustrative and exemplary purposes. However, as previously indicated above, the variable geometry, shape, and, form, of the ventricular device of specific case (a), in general, and, the at least one elastic component such as elastic arms or extensions 12, in particular, are characterized by at least one physical aspect or descriptor selected from the group consisting of a variable extent or degree of symmetry, a variable extent or degree of asymmetry, and combinations thereof.

Figure 6A:
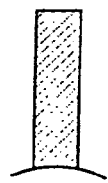
FIGS. 6A-6I are schematic diagrams illustrating an exemplary arm or extension of the ventricular device having variable geometry, shape, form, and, dimensions, for implementing specific case (a) of the first principle preferred embodiment of the method, of positioning the at least one elastic component of the ventricular device adjacent to the inner wall surface of the left ventricle, in accordance with the present invention.

FIG. 6A is a schematic diagram illustrating an exemplary elastic arm or extension 12 having geometry, shape, and, form, primarily characterized as rectangular, symmetrical, with a surface completely solid featuring no cut-out or hollow pattern.

Figure 6B:

FIG. 6B is a schematic diagram illustrating an exemplary elastic arm or extension 12 having geometry, shape, and, form, primarily characterized as circular or elliptical, symmetrical, with a surface incompletely solid featuring a cut-out or hollow pattern.

Figure 6C:
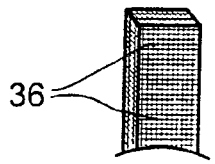

FIG. 6C is a schematic diagram illustrating an exemplary elastic arm or extension 12 having geometry, shape, and, form, primarily characterized as rectangular, symmetrical, with a surface incompletely solid featuring a cut-out or hollow pattern such as a cellular or net cut-out or hollow pattern, including a plurality of hollow cells 36. There are two important aspects associated with this configuration of elastic arm or extension 12. The first important aspect is that the plurality of adjacent hollow cells 36 increases effectiveness of the elastic functionality of ventricular device 10 (FIGS. 2A and 2B), in order to properly fulfill the main objective of sufficiently reducing intracardiac hydrostatic pressure during ventricular diastole of the heart, thereby, improving diastolic function of the left ventricle of the heart. The second important aspect is that the plurality of adjacent hollow cells 36 facilitates growth of endocardium onto the surface of ventricular device 10 (FIGS. 2A and 2B), thus reducing risk of thromboembolic complications.

Figure 6D:
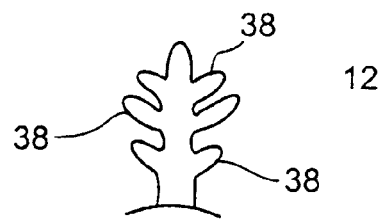

FIG. 6D is a schematic diagram illustrating an exemplary elastic arm or extension 12 having geometry, shape, and, form, primarily characterized as moderately branched with symmetric and asymmetric coarse branches 38.

Figure 6E:
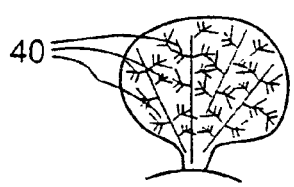

FIG. 6E is a schematic diagram illustrating an exemplary elastic arm or extension 12 having geometry, shape, and, form, primarily characterized as significantly branched with symmetric and asymmetric fine branches 40.

Figure 6F:

FIG. 6F is a schematic diagram illustrating an exemplary elastic arm or extension 12 having geometry, shape, and, form, primarily characterized as curved or bent.

Figure 6G:
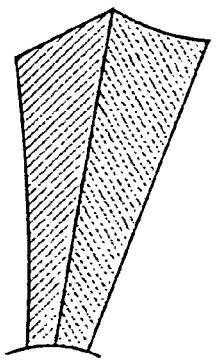

FIG. 6G is a schematic diagram illustrating a perspective view of an exemplary elastic arm or extension 12 having geometry, shape, and, form, primarily characterized as bent, symmetrical, with a surface completely solid featuring no cut-out or hollow pattern.

Figure 6H:
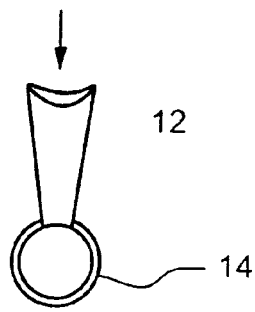

FIG. 6H is a schematic diagram illustrating a perspective view of an exemplary elastic arm or extension 12 having geometry, shape, and, form, primarily characterized as bent inwards at the end region (indicated by the arrow). In a non-limiting fashion, elastic arm or extension 12 is shown integral and continuous to a single optional elastic lower basal section or ring formation 14. In an alternative embodiment of exemplary elastic arm or extension 12 of FIG. 6H, elastic arm or extension 12 has geometry, shape, and, form, primarily characterized as bent inwards at the end region and throughout the length of elastic arm or extension 12 extending down to single optional elastic lower basal section or ring formation 14.

Figure 6I:
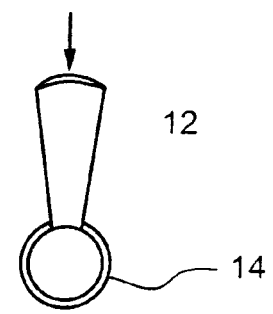

FIG. 6I is a schematic diagram illustrating a perspective view of an exemplary elastic arm or extension 12 having geometry, shape, and, form, primarily characterized as bent outwards at the end region (indicated by the arrow). In a non-limiting fashion, elastic arm or extension 12 is shown integral and continuous to a single optional elastic lower basal section or ring formation 14. In an alternative embodiment of exemplary elastic arm or extension 12 of FIG. 6I, elastic arm or extension 12 has geometry, shape, and, form, primarily characterized as bent outwards at the end region and throughout the length of elastic arm or extension 12 extending down to single optional elastic lower basal section or ring formation 14.

In alternative embodiments, the side view or profile of elastic arms or extensions 12 of exemplary ventricular device 10 (FIGS. 2A and 2B), for implementing specific case (a) of the first principle preferred embodiment of the method and device, has variable geometry, shape, form, and, dimensions, as illustrated in FIGS. 7A-7E. In a non-limiting fashion, each exemplary alternative embodiment shows elastic arm or extension 12 integral and continuous to a single optional elastic lower basal section or ring formation 14.

Figure 7A:
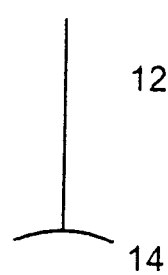
FIGS. 7A-7E are schematic diagrams illustrating side views or profiles of an exemplary elastic arm or extension having variable geometry, shape, form, and, dimensions, for implementing specific case (a) of the first principle preferred embodiment of the method, of positioning the at least one elastic component of the ventricular device adjacent to the inner wall surface of the left ventricle, in accordance with the present invention.

FIG. 7A is a schematic diagram illustrating a side view or profile of an exemplary elastic arm or extension 12 having geometry, shape, and, form, primarily characterized as straight.

Figure 7B:
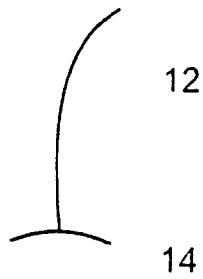

FIG. 7B is a schematic diagram illustrating a side view or profile of an exemplary elastic arm or extension 12 having geometry, shape, and, form, primarily characterized as outwardly curved or bent.

Figure 7C:
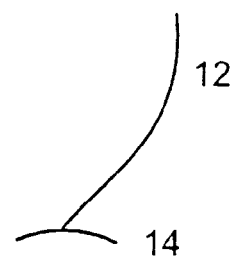

FIG. 7C is a schematic diagram illustrating a side view or profile of an exemplary elastic arm or extension 12 having geometry, shape, and, form, primarily characterized as inwardly curved or bent.

Figure 7D:
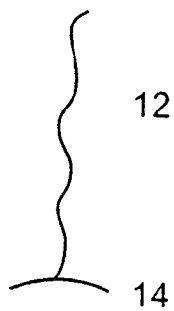

FIG. 7D is a schematic diagram illustrating a side view or profile of an exemplary elastic arm or extension 12 having geometry, shape, and, form, primarily characterized as wavy.

Figure 7E:
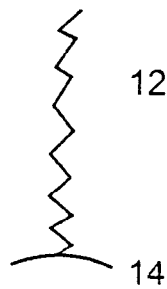

FIG. 7E is a schematic diagram illustrating a side view or profile of an exemplary elastic arm or extension 12 having geometry, shape, and, form, primarily characterized as sawtoothed.

Figure 8A:
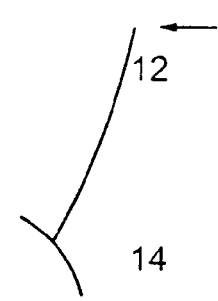
FIGS. 8A-8C are schematic diagrams illustrating side views of an exemplary elastic arm or extension, of the ventricular device, including a free end having variable geometry, shape, form, and, dimensions, for implementing specific case (a) of the first principle preferred embodiment of the method, of positioning the at least one elastic component of the ventricular device adjacent to the inner wall surface of the left ventricle, in accordance with the present invention.
Figure 8B:
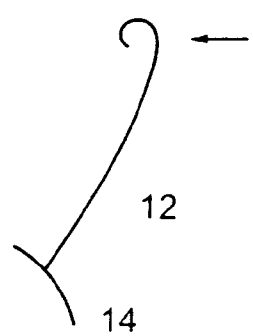
Figure 8C:
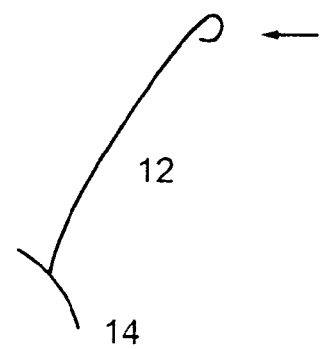

In alternative embodiments, the top or free ends of elastic arms or extensions 12 of exemplary ventricular device 10 (FIGS. 2A and 2B), for implementing specific case (a) of the first principle preferred embodiment of the method and device, have variable geometry, shape, form, and, dimensions, as illustrated in FIGS. 8A-8C. In a non-limiting fashion, each exemplary alternative embodiment shows elastic arm or extension 12 integral and continuous to a single optional elastic lower basal section or ring formation 14.

FIG. 8A is a schematic diagram illustrating a side view of an exemplary elastic arm or extension 12 including a free end (indicated by the arrow), having geometry, shape, and, form, primarily characterized as straight and in the same plane as elastic arm or extension 12.

FIG. 8B is a schematic diagram illustrating a side view of an exemplary elastic arm or extension 12 including a free end (indicated by the arrow), having geometry, shape, and, form, primarily characterized as inwardly curved relative to elastic arm or extension 12. An important aspect associated with this configuration of elastic arm or extension 12 is that during systole of the cardiac cycle, while there is contraction of the myocard, the inwardly curved free end is less likely to injure cardiac muscle inside the left ventricle.

FIG. 8C is a schematic diagram illustrating a side view of an exemplary elastic arm or extension 12 including a free end (indicated by the arrow), having geometry, shape, and, form, primarily characterized as outwardly curved relative to elastic arm or extension 12. An important aspect associated with this configuration of elastic arm or extension 12 is that the outwardly curved free end serves as a means of contact with and/or attachment to the inner wall surface of the left ventricle, for properly and optimally performing the critical function of potentially exerting a radially outward, elastic, pushing type of the expansive force or pressure to the inner wall surface of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart.

Figure 9:
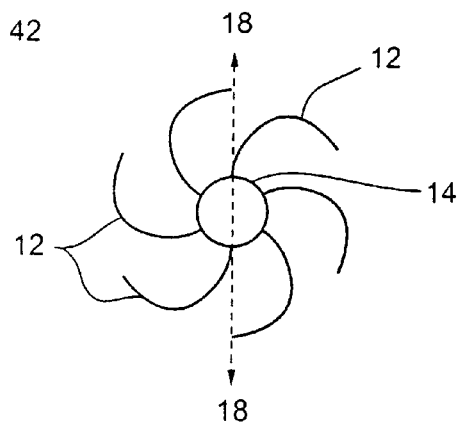
FIG. 9 is a schematic diagram illustrating a top view of an exemplary circular or helical shaped ventricular device, featuring six elastic arms or extensions which are circular or helical around the central longitudinal axis, with a single optional elastic lower basal section or ring formation, for implementing specific case (a) of the first principle preferred embodiment of the method, of positioning the at least one elastic component of the ventricular device adjacent to the inner wall surface of the left ventricle, in accordance with the present invention.

Referring again to FIGS. 2A and 2B, in alternative embodiments, elastic arms or extensions 12 of exemplary ventricular device 10, for implementing specific case (a) of the first principle preferred embodiment of the method and device, of positioning the at least one elastic component of the ventricular device adjacent to the inner wall surface of the left ventricle, longitudinally and radially extend from optional elastic lower basal section or ring formation 14 by a variable angle from horizontal axis 24, thus providing variability of the diameter across the widest end, that is, the distance extending along plane 22 spanning across the top or free ends of elastic arms or extensions 12, and, providing variability of the diameter across the narrowest end, that is, the distance extending along plane 24 spanning across optional elastic lower basal section or ring formation 14. Alternatively, or, additionally, elastic arms or extensions 12 of exemplary ventricular device 10 longitudinally and radially extend from optional elastic lower basal section or ring formation 14 by a variable angle from central longitudinal axis 18, whereby elastic arms or extensions 12 have geometry, shape, and, form primarily characterized as circular or helical around central longitudinal axis 18, as illustrated in FIG. 9, a schematic diagram illustrating a top view of an exemplary circular or helical shaped ventricular device 42, featuring six elastic arms or extensions which are essentially of the same geometry, shape, form, and, dimensions, circular or helical around central longitudinal axis 18, and integral and continuous with a single optional elastic lower basal section or ring formation 14.

As previously stated above, in the general description of the first principle preferred embodiment of the method and device, applicable to each specific case (a)-(d), in alternative embodiments, the ventricular device further includes at least one non-elastic component or mechanism, which operatively functions together with other elements or components of the ventricular device for optimally effecting the elastic functionality of the ventricular device, while minimally disturbing systolic function of the heart.

Accordingly, in alternative embodiments, for implementing specific case (a) of the first principle preferred embodiment of the method and device, ventricular device 10 (FIGS. 2A and 2B), in general, including elastic arms or extensions 12 and optional elastic lower basal section or ring formation 14, in particular, further includes at least one non-elastic component or mechanism for anchoring, adhering, and/or, attaching, at least one part or region of ventricular device 10, in general, such as elastic arms or extensions 12 and/or optional elastic lower basal section or ring formation 14, in particular, to at least one part of the inner wall surface of the left ventricle where ventricular device 10 is configured for in-vivo elastic operation.

Specific types, and materials of construction, geometry, shape, form, and, dimensions, of the at least one anchoring, adhering, and/or, attaching, component or mechanism are described in the general description, above, and are applicable to ventricular device 10 of specific case (a). Two exemplary types, non-transmural and transmural, of anchoring, adhering, and/or, attaching, mechanisms applicable to ventricular device 10 of specific case (a) are herein described and illustrated in FIGS. 10A and 10B, respectively, following.

Figure 10A:
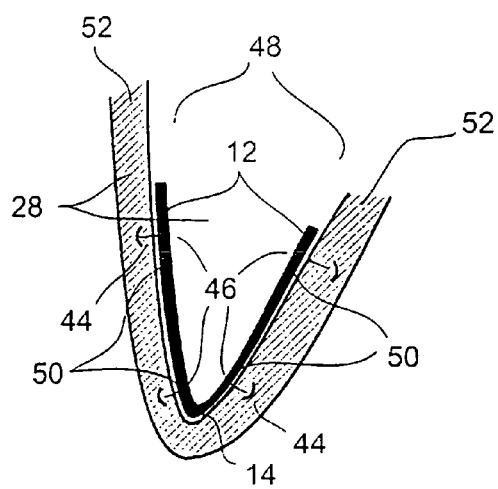
FIG. 10A is a schematic diagram illustrating a cross sectional view of a non-transmural, exemplary first type of anchoring, adhering, and/or, attaching, mechanism, for implementing specific case (a) of the first principle preferred embodiment of the method, of positioning the at least one elastic component of the ventricular device adjacent to the inner wall surface of the left ventricle, in accordance with the present invention.

FIG. 10A is a schematic diagram illustrating a cross sectional view of a non-transmural, exemplary first type of mechanism 44 for anchoring, adhering, and/or, attaching, at least one part or region 46 of an exemplary ventricular device 48, in general, such as elastic arms or extensions 12 and/or optional elastic lower basal section or ring formation 14, in particular, in a rest position, to at least one part of inner wall surface 50 of left ventricle 28 where exemplary ventricular device 48 is configured for in-vivo elastic operation. As shown, exemplary anchoring, adhering, and/or, attaching, mechanism 44 only partly enters into or penetrates intermediate wall region 52 of left ventricle 28, and is therefore a non-transmural type of anchoring, adhering, and/or, attaching, mechanism.

Figure 10B:
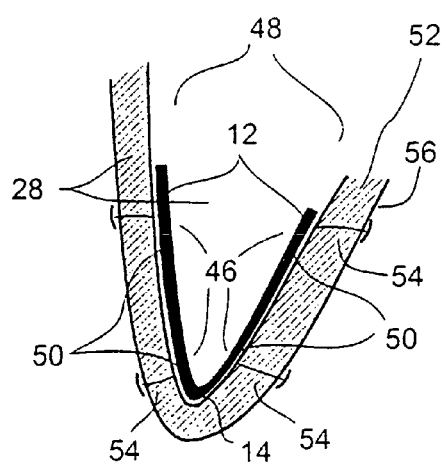
FIG. 10B is a schematic diagram illustrating a cross sectional view of a transmural, exemplary second type of anchoring, adhering, and/or, attaching, mechanism, for implementing specific case (a) of the first principle preferred embodiment of the method, of positioning the at least one elastic component of the ventricular device adjacent to the inner wall surface of the left ventricle, in accordance with the present invention.

FIG. 10B is a schematic diagram illustrating a cross sectional view of a transmural, exemplary second type of mechanism 54 for anchoring, adhering, and/or, attaching, at least one part or region 46 of an exemplary ventricular device 48, in general, such as elastic arms or extensions 12 and/or optional elastic lower basal section or ring formation 14, in particular, in a rest position, to at least one part of inner wall surface 50 of left ventricle 28 where exemplary ventricular device 48 is configured for in-vivo elastic operation. As shown, exemplary anchoring, adhering, and/or, attaching, mechanism 54 fully enters into or penetrates intermediate wall region 52 of left ventricle 28, and is therefore a transmural type of anchoring, adhering, and/or, attaching, mechanism. Moreover, according to appropriate design, materials of construction, geometry, shape, form, and, dimensions, exemplary anchoring, adhering, and/or, attaching, mechanism 54 expands onto and around the surface of the outer wall surface 56 of left ventricle 28, thereby increasing the effective surface area of exemplary anchoring, adhering, and/or, attaching, mechanism 54.

A second general type of an exemplary ventricular device, including the at least one elastic component, for implementing specific case (a) of the first principle preferred embodiment of the method and device of the present invention, is described and illustrated in FIG. 1, as follows.

Figure 11:
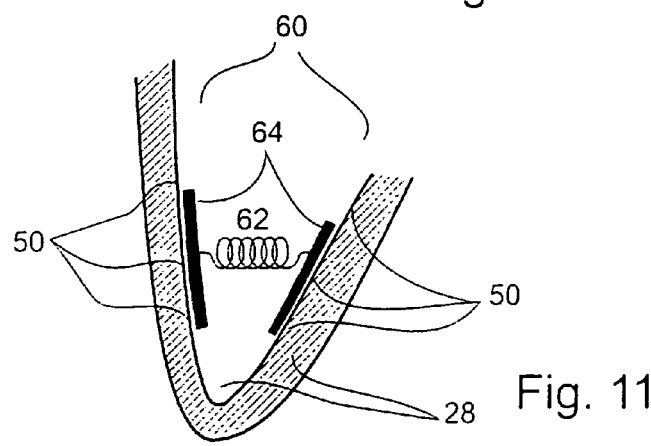
FIG. 11 is a schematic diagram illustrating a cross sectional view of a second general type of exemplary ventricular device for implementing specific case (a) of the first principle preferred embodiment of the method, of positioning the at least one elastic component of the ventricular device adjacent to the inner wall surface of the left ventricle, in accordance with the present invention.

FIG. 11 is a schematic diagram illustrating a cross sectional view of a second general type of exemplary ventricular device, generally referred to as ventricular device 60, for implementing specific case (a) of the first principle preferred embodiment of the method and device, of positioning the at least one elastic component of the ventricular device adjacent to the inner wall surface of the left ventricle. In FIG. 11, ventricular device 60 is illustrated in a 'rest' position, that is, in a position whereby ventricular device 60 potentially applies a radially outward, elastic, pushing type of the expansive force or pressure to inner wall surface 50 of left ventricle 28.

In this second general type of exemplary embodiment, ventricular device 60 is designed, configured, and, constructed, as an integral single complex elastic component, herein, also referred to as elastic component 60, featuring at least one elastic element or mechanism functioning and structured as a spring, for example, spring 62, connected or attached to a plurality of at least two ventricular wall contact elements 64 positioned adjacent to and along inner wall surface 50 of left ventricle 28. Ventricular device or elastic component 60 features the physicochemical property and behavior of elasticity, whereby, ventricular device or elastic component 60 is positioned adjacent to at least one part of inner wall surface 50 of left ventricle 28, and potentially exerts a radially outward, elastic, pushing type of the expansive force or pressure to inner wall surface 50 of left ventricle 28 for reducing intracardiac hydrostatic pressure during ventricular diastole of the heart, thereby, improving diastolic function of left ventricle 28 of the heart, while minimally disturbing systolic function of the heart.

Ventricular device or elastic component 60, in general, including elastic element or mechanism 62 connected or attached to ventricular wall contact elements 64, in particular, is designed, configured, and constructed, whereby ventricular device 60 is inserted into place by using a minimally invasive surgical procedure, such as catheterization, thoracoscopy, or, thoracotomy, with a relatively small diameter delivery system (not shown) for delivering and deploying ventricular device 60 into the body, in general, and to a left ventricular cardiac inner wall surface, in particular. Specific types, and materials of construction, geometry, shape, form, and, dimensions, of ventricular device or elastic component 60, in general, including elastic element or mechanism 62 connected or attached to intra-ventricular contact elements 64, in particular, are described in the general description, above, of the first principle preferred embodiment of the method and device, and are applicable to specific case (a).

In alternative embodiments, ventricular device or elastic component 60, shown in FIG. 11, in general, including elastic element or mechanism 62 connected or attached to ventricular wall contact elements 64, in particular, has variable geometry, shape, form, and, dimensions, and, elastic strength, which, as previously indicated above, are specifically determined, in part, according to actual or measured dynamical (variable) geometry, shape, form, and, dimensions of an actual heart, in general, and, of an actual left ventricle, in particular, and, are also specifically determined, in part, according to the desired or necessary extent or degree of elasticity, for properly and optimally performing the critical function of potentially exerting a radially outward, elastic, pushing type of the expansive force or pressure (in a range of about 5-20 mm Hg, preferably, about 10 mm Hg) to the inner wall surface of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

As previously stated above, in the general description of the first principle preferred embodiment of the method and device, applicable to each specific case (a)-(d), in alternative embodiments, the ventricular device further includes at least one non-elastic component or mechanism which operatively functions together with the ventricular device for optimally effecting the elastic functionality of the ventricular device, while minimally disturbing systolic function of the heart.

Accordingly, in alternative embodiments, ventricular device or elastic component 60 (FIG. 11), in general, including elastic element or mechanism 62 and ventricular wall contact elements 64, in particular, further includes at least one non-elastic component or mechanism for anchoring, adhering, and/or, attaching, at least one part or region of ventricular device or elastic component 60, in general, such as ventricular wall contact elements 64, in particular, to at least one part of the inner wall surface of the left ventricle where ventricular device or elastic component 60 is configured for in-vivo elastic operation.

Specific types, and materials of construction, geometry, shape, form, and, dimensions, of the at least one anchoring, adhering, and/or, attaching, component or mechanism are described in the general description, above, and are applicable to ventricular device 60 of specific case (a). In particular, the two exemplary types, non-transmural and transmural, of anchoring, adhering, and/or, attaching, mechanisms applicable to ventricular device 10 of specific case (a), previously described and illustrated in FIGS. 10A and 10B, respectively, are also applicable to ventricular device or elastic component 60.

As previously stated, above, in the general description of Step (a) of the first principle preferred embodiment of the method and device, applicable to the ventricular device of specific case (a), the at least one elastic component of the ventricular device is positioned adjacent to at least one part of inner wall surface of the left ventricle, whereby the at least one elastic component exerts the potential expansive, radially outward, elastic, pushing, type of force or pressure to the inner wall surface of the left ventricle during ventricular diastole, while minimally disturbing systolic function of the heart. This applies to all previously described and illustrated general types and exemplary alternative embodiments of the ventricular device of specific case (a) of the first principle preferred embodiment of the method and device.

Specifically, this applies to the first general type and exemplary alternative embodiments of ventricular device or elastic component 10, featuring at least one elastic arm or extension 12, optionally, longitudinally and radially extending from at least one optional elastic lower basal section or ring formation 14, as shown in FIGS. 2A-10B. Specifically, this also applies to the second general type and exemplary alternative embodiments of ventricular device or elastic component 60, featuring at least one elastic element or mechanism 62 functioning and structured as a spring connected or attached to at least two intra-ventricular contact elements 64, as shown in FIG. 11.

For specific case (a) of the method and device, where the ventricular device, for example, ventricular device or elastic component 10, or, ventricular device or elastic component 60, is connected to at least one part of the inner wall surface of the left ventricle, following inserting and maneuvering of the ventricular device inside the cardiac lumen of the heart, the ventricular device is connected to the inner wall surface of the left ventricle. Connecting, by way of anchoring, adhering, and/or, attaching, the ventricular device, including the at least one elastic component, is performed by using at least one anchoring, adhering, and/or, attaching, component or mechanism, included as part of the ventricular device, as previously described above, and/or, separate from the ventricular device.

For specific case (a) of the method and device, the ventricular device is inserted into place by using a minimally invasive surgical procedure, such as catheterization, thoracoscopy, or, thoracotomy, with a relatively small diameter delivery system (not shown) for delivering and deploying the ventricular device into the body, in general, and to a left ventricular cardiac inner wall surface, in particular. Alternatively, the ventricular device is inserted into place by using trans-apical deployment. Alternatively, the ventricular device may be inserted and positioned through the left atrium and the mitral valve of the heart under direct visualization, as part of an open-heart procedure. In this case, the technique for fixing the ventricular device after proper positioning in the left ventricle is similar to that used during trans-apical deployment.

Techniques and equipment of percutaneous transluminal catheterization deployment are well taught about in the prior art, however, for enabling implementation of the method and device of the present invention, some details are provided herein. In general, a catheterization delivery system consists of a tube, the inner caliber of which corresponds to the diameter of the ventricular device in its fully contracted configuration. The tube is inserted to a peripheral artery, most commonly the femoral artery, and is then led into the aorta, and through the aortic valve inserted into the left ventricle. The ventricular device is then positioned and configured by using the catheterization delivery system with echocardiographic guidance (trans-esophageal or transthoracic). Catheterization is usually done under direct radiographic visualization, using radiographic contrast material injected by the delivery system.

Techniques and equipment of trans-apical deployment are well taught about in the prior art, however, for enabling implementation of the method and device of the present invention, some details are provided herein. In general, a trans-apical delivery system consists of a tube, the inner caliber of which corresponds to the diameter of the ventricular device in its fully contracted configuration. In trans-apical deployment, a small incision is made in the lowest (apical or apex) area of the heart, where the left ventricle is narrowest. Through this incision, the ventricular device, in a contracted or closed position, within the trans-apical delivery system, is inserted into the left ventricular cavity. The ventricular device is then positioned and configured by using the trans-apical delivery system with echocardiographic guidance (trans-esophageal or epicardial). The ventricular device, connected to a leading handle of the trans-apical delivery system, is translationally and angularly (by rotation) movable within the tube. The leading handle has a water-tight piston having the same caliber of the tube in order to avoid bleeding during the insertion procedure. The trans-apical delivery system is inserted through the above indicated apical incision, and the ventricular device is guided and pushed into the ventricular cavity and rotated as necessary until proper positioning is accomplished, while the insertion tube is retracted in the opposite direction, out of the heart.

After configuring the ventricular device, the incision is closed by surgical suturing or by a closing mechanism already attached to the ventricular device. Trans-apical insertion requires a minimally invasive surgical procedure, or, may be done using a thoracoscopic delivery system. Both insertion methods may require the ventricular device to be inserted in a contracted or closed position, followed by expanding or opening the ventricular device, that is, the at least one elastic component, for in-vivo operation once configured and positioned adjacent to and/or along the inner wall surface of the left ventricle.

As previously stated above, in Step (a), in specific case (b) of the first principle preferred embodiment of the method and device, the ventricular elastic device includes at least one component featuring the physicochemical property and behavior of elasticity, whereby, the at least one elastic component of the device is positioned adjacent to at least one part of outer wall surface of the left ventricle, and potentially exerts a radially outward, elastic, pulling type of the expansive force or pressure to the outer wall surface of the left ventricle for reducing intracardiac hydrostatic pressure during ventricular diastole of the heart, thereby, improving diastolic function of the left ventricle of the heart, while minimally disturbing systolic function of the heart.

Figure 12:
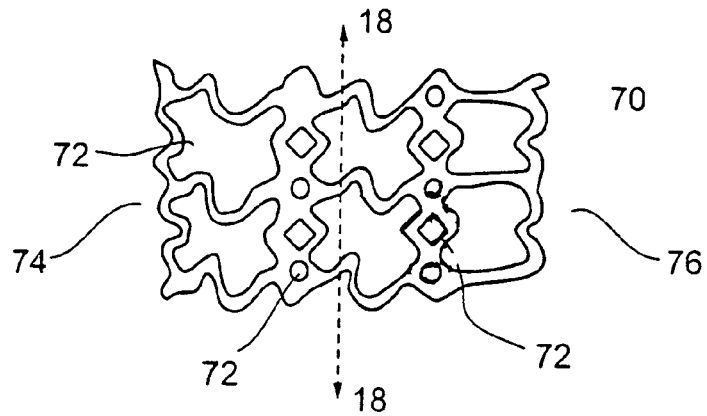
FIG. 12 is a schematic diagram illustrating a two-dimensional planar view of a general type of exemplary ventricular device for implementing specific case (b) of the first principle preferred embodiment of the method, of positioning the at least one elastic component of the ventricular device adjacent to the outer wall surface of the left ventricle, in accordance with the present invention.

Referring again to the drawings, FIG. 12 is a schematic diagram illustrating a two-dimensional planar view of a general type of exemplary device, generally referred to as ventricular device 70, for implementing specific case (b) of the first principle preferred embodiment of the method and device, of positioning the at least one elastic component of the ventricular device adjacent to the outer wall surface of the left ventricle. In FIG. 12, ventricular device 70 is illustrated in a 'rest' position, that is, in a position whereby ventricular device 70 potentially applies a radially outward, elastic, pulling type of the expansive force or pressure to the outer wall surface of the left ventricle.

In this general type of exemplary embodiment, ventricular device 70 is designed, configured, and, constructed, as an integral single elastic component, herein, also referred to as elastic component 70, having at least a partially cylindrical or annular geometry, shape, and, form, relative to central longitudinal axis 18, with a surface incompletely solid characterized by a cut-out or hollow pattern, such as a cellular or net cut-out or hollow pattern, including a plurality of hollow cells 72. The plurality of hollow cells features cells having dimensions selected from the group consisting of same dimensions, variable dimensions, and, a combination thereof. For example, as shown in FIG. 12, hollow cells 72 are of variable dimensions. In alternative embodiments, ventricular device 70 is designed, configured, and, constructed, as an integral single elastic component having a geometry, shape, and, form, selected from the group consisting of partially cylindrical, partially annular, partially conical, fully cylindrical, fully annular, and, fully conical, relative to central longitudinal axis 18.

Ventricular device or elastic component 70 has variable geometry, shape, form, and, dimensions, and, elastic strength, which, as previously indicated above, are specifically determined, in part, according to actual or measured dynamical (variable) geometry, shape, form, and, dimensions of an actual functioning heart, in general, and, of an actual functioning left ventricle, in particular, and, are also specifically determined, in part, according to the desired or necessary extent or degree of elasticity, for properly and optimally performing the critical function of potentially exerting a radially outward, elastic, pulling type of the expansive force or pressure (in a range of about 5-20 mm Hg, preferably, about 10 mm Hg) to the outer wall surface of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

Figure 13A:
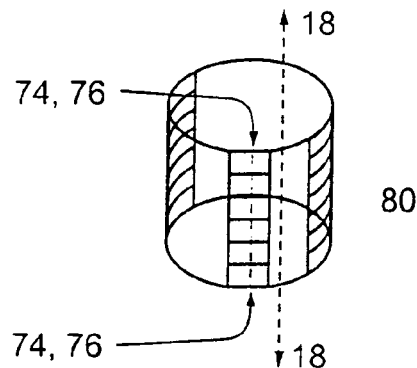
FIG. 13A is a schematic diagram illustrating a perspective view of an exemplary ventricular device having a fully cylindrical geometry, shape, and, form, for implementing specific case (b) of the first principle preferred embodiment of the method, of positioning the at least one elastic component of the ventricular device adjacent to the outer wall surface of the left ventricle, in accordance with the present invention.
Figure 13B:
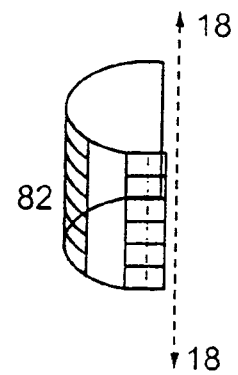
FIG. 13B is a schematic diagram illustrating a perspective view of an exemplary ventricular device having a partially cylindrical geometry, shape, and, form, for implementing specific case (b) of the first principle preferred embodiment of the method, of positioning the at least one elastic component of the ventricular device adjacent to the outer wall surface of the left ventricle, in accordance with the present invention.

Two particular examples of ventricular device or elastic component 70, for implementing specific case (b) of the first principle preferred embodiment of the method and device, are illustrated in FIGS. 13A and 13B. FIG. 13A is a schematic diagram illustrating a perspective view of an exemplary ventricular device 80, having a fully cylindrical geometry, shape, and, form, relative to central longitudinal axis 18. Ventricular device 80 in FIG. 13A illustrates left edge 74 and right edge 76 of ventricular device 70 (FIG. 12) joined to and integral with one another, whereby the surface of ventricular device 80 completely encircles the outer wall surface of both ventricles of the heart (not shown). FIG. 13B is a schematic diagram illustrating a perspective view of an exemplary ventricular device 82, having a partially cylindrical geometry, shape, and, form, relative to central longitudinal axis 18. The surface of ventricular device 82 only partially encircles the outer wall surface of the heart (not shown).

Figure 14:
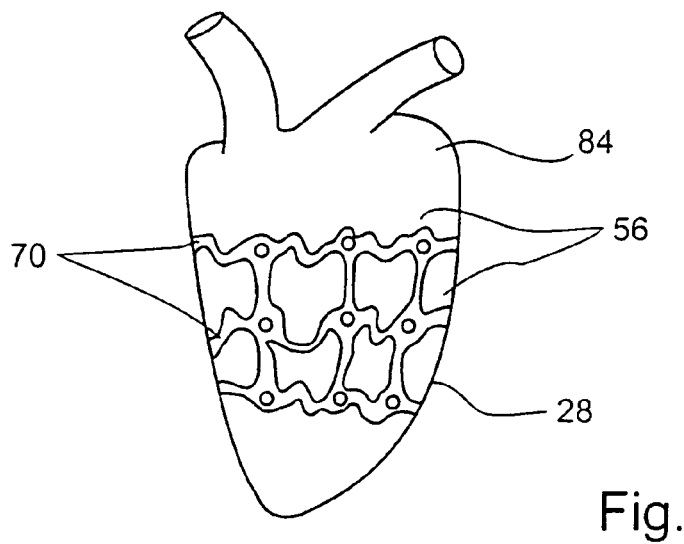
FIG. 14 is a schematic diagram illustrating a perspective view of an exemplary rest position of exemplary cylindrically shaped ventricular device or elastic component of FIG. 12, positioned around the outer wall surface of a heart, for implementing specific case (b) of the first principle preferred embodiment of the method, of positioning the at least one elastic component of the ventricular device adjacent to the outer wall surface of the left ventricle, in accordance with the present invention.

FIG. 14 is a schematic diagram illustrating a perspective view of an exemplary rest position of exemplary cylindrically shaped ventricular device or elastic component 70 (FIG. 12) positioned around the outer wall surface of a heart 84, including around outer wall surface 56 of left ventricle 28. Many alternative specific embodiments of exemplary ventricular device or elastic component 70, consistent with the function/structure description of exemplary ventricular device or elastic component 70, above, are clearly possible, for implementing specific case (b) of the first principle preferred embodiment of the method and device.

Included among the many abovementioned alternative specific embodiments of exemplary ventricular devices for use in implementing specific case (b) of the first principle preferred embodiment of the method and device is a group of said devices that are characterized by their capability for applying tangential forces to the ventricular wall, in addition to the outward, radial expansive forces described hereinabove. The devices contained within this group are also characterized by their high degree of anatomical and physiological compatibility. This aspect of the present invention, therefore, is primarily directed to an anatomically-compatible and physiologically-compatible in vivo device for improving diastolic function of either the left or right ventricle of the heart, comprising:

at least one elastic component that is capable of being operatively connected to the external ventricular surface of the heart by means of one or more connecting elements, wherein said at least one elastic component comprises a plurality of essentially longitudinal members which are arranged such that the lateral separation between adjacent longitudinal members may be increased or decreased in response to elastic deformation of said elastic component, and wherein said essentially longitudinal members are arranged relative to each other such that said elastic component is curved in both the vertical and horizontal planes, such that the inner surface of said elastic component may be adapted to the curvature of the external ventricular surface of the heart, or a portion thereof, such that said at least one elastic component is capable of exerting both a radially outward expansive force and a tangentially-directed force on the external ventricular surface of the heart to which said component may be connected by means of said one or more connecting elements.

The term "anatomically compatible" as used hereinbefore refers to the fact that the structure of the device of the invention is such that it may readily be adapted in situ to the precise shape and size of the heart to be treated.

The term "physiologically compatible" as used hereinbefore refers to the fact that the structure of the device of the invention is such that it may readily be adapted in situ to the precise movement vectors of the heart to be treated.

According to one preferred embodiment of this aspect of the invention, the device comprises only one elastic component.

In one particularly preferred embodiment of the device of the invention, the elastic component comprises a plurality of elongated members, each of said elongated members having one end connected to, and continuous with, a base element, said base element being of a size and shape such that it is capable of either fully or partially encircling the apical region of the heart, and wherein said elongated members are arranged such that they are capable of being disposed in an essentially longitudinal manner along the external ventricular surface of the heart, such that said free ends of said elongated members are directed towards the base of the heart. In a particularly preferred embodiment, the abovementioned base element is provided in an annular shape.

In another particularly preferred embodiment of this type of device, the elastic component comprises a wire spring, wherein said wire spring is bent such that it contains one or more angled portions, each angled portion comprising either an inferiorly-directed or a superiorly-directed apex that is formed at the junction of two essentially-longitudinally disposed lengths, and wherein said spring is capable of being connected to the external ventricular surface of the heart in an essentially horizontal orientation.

In the present context, the term "longitudinal" as used herein in relation to the in vivo device of the invention refers to a plane that is approximately parallel with an imaginary line connecting the apex of the heart with the center point of its base. Also, the term "horizontal" is to be understood as referring to an essentially equatorial plane, that is, a plane that is approximately parallel with that defined in a transverse section of the heart.

According to another preferred embodiment of this aspect of the invention, the in vivo device comprises two or more elastic components. In one particularly preferred embodiment, each of the two or more elastic components comprises a wire spring of the type defined hereinabove. In another particularly preferred embodiment, each of the two or more elastic components comprises a plurality of elongated members and a base element, as defined hereinabove.

Although the at least one elastic component of the in vivo device of the invention may be constructed of any suitable material possessing the desired spring-like properties, in a preferred embodiment, said at least one elastic component is constructed from a material selected from the group consisting of tungsten, platinum, titanium, nitinol alloy, stainless steel alloy, and, combinations thereof.

According to one preferred embodiment of the device of the invention, said device is constructed such that the aforementioned maximal value for the radially outward expansive pressure exerted on at least one part of the external ventricular wall is in a range of about 5 mm Hg to about 40 mm Hg.

The present invention is also directed to a connecting element suitable for connecting a medical or surgical device to an organ or tissue of the body, comprising a girdle in the form of a thin fabric patch, extending from the lateral borders of which is a plurality of tabs arranged in contralateral pairs, wherein each tab is capable of being joined to its contralateral partner, thereby forming a loop into which may be inserted a portion of the device which is to be connected to said organ or tissue.

In another aspect, the present invention is also directed to several different connecting elements for use in connecting the device of the invention to the external surface of the heart.

In one preferred embodiment, the invention provides a transmural or intramural anchor for use as a connecting element for connecting the in vivo device disclosed hereinabove to the external ventricular surface of the heart In another preferred embodiment, the connecting element is provided in the form of a girdle as described hereinabove.

In yet another preferred embodiment, the connecting element is provided in the form of a tube constructed of a biocompatible material. In one particularly preferred embodiment, this material is Dacron. In another particularly preferred embodiment, the material is polytetrafluorethylene (PTFE).

While many other different materials may be used as connecting elements for affixing the in vivo device of the invention to the external surface of the heart, according to one preferred embodiment, the connecting elements are selected from the group consisting of biocompatible pins (including intramural and other non-transmural pins), biocompatible needles, biocompatible spikes, biocompatible screws, biocompatible clamps, biocompatible glue, surgical sutures, and, combinations thereof.

Figure 24:
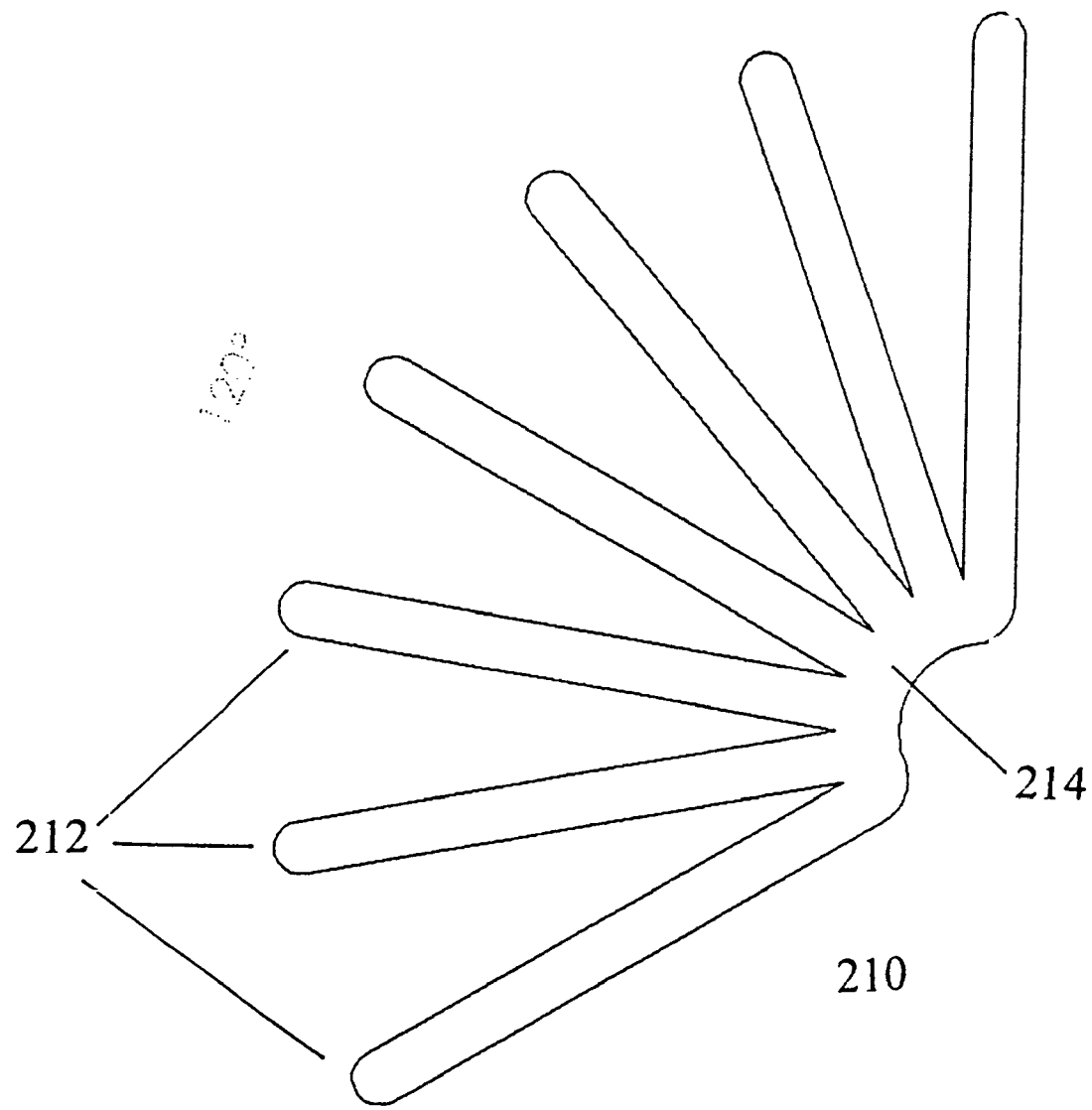
FIG. 24 is a schematic diagram illustrating a two-dimensional view of another type of exemplary ventricular device for implementing specific case (b) of the first principle preferred embodiment of the method, of positioning the at least one elastic component of the ventricular device adjacent to the outer wall surface of the left ventricle, in accordance with the present invention, wherein the ventricular device comprises a plurality of elongated members connected at one end by a base element.

Referring again to the drawings, FIG. 24 depicts one preferred embodiment of the device of the present invention, generally indicated by numeral 210, comprising a plurality of elongated members 212, each of which are connected at one of their extremities to curved base element 214. The device shown in this figure comprises seven elongated members 212, such that when said device is in the flat, unfolded state (as shown in the view given in FIG. 24), the angle formed between the imaginary longitudinal midlines of the first and last of such members is approximately 120°. This embodiment may be constructed in a variety of sizes in order to accommodate, the range of cardiac dimensions normally encountered. In the particular embodiment depicted in FIG. 24, each elongated member 212 is of length 70 mm, including the width of base member 214, with which said elongated member is continuous. Another example of this embodiment of the device of the invention is depicted in its unfolded condition, in plan view, in FIG. 25. In this case, the device comprises four elongated members 212, the angle formed between the imaginary longitudinal midlines of the first and last of such members being approximately 120°. In devices of the type depicted in FIGS. 24 and 25, the elongated members 212 may be constructed such that they have any suitable width. In the examples of such devices shown in FIGS. 24 and 25, said elongated members have a width of 6 mm. It is to be noted that the longitudinal elongated members may take many different forms, in addition to those depicted in FIGS. 24 and 25. For example, said members may be perforated by a series of small holes in order to allow attachment thereof to the ventricular wall. In addition, the members may (in plan view) be curved or otherwise formed into non-linear shapes. Furthermore, within one device, different members may be constructed in a plurality of shapes and sizes.

Figure 25:
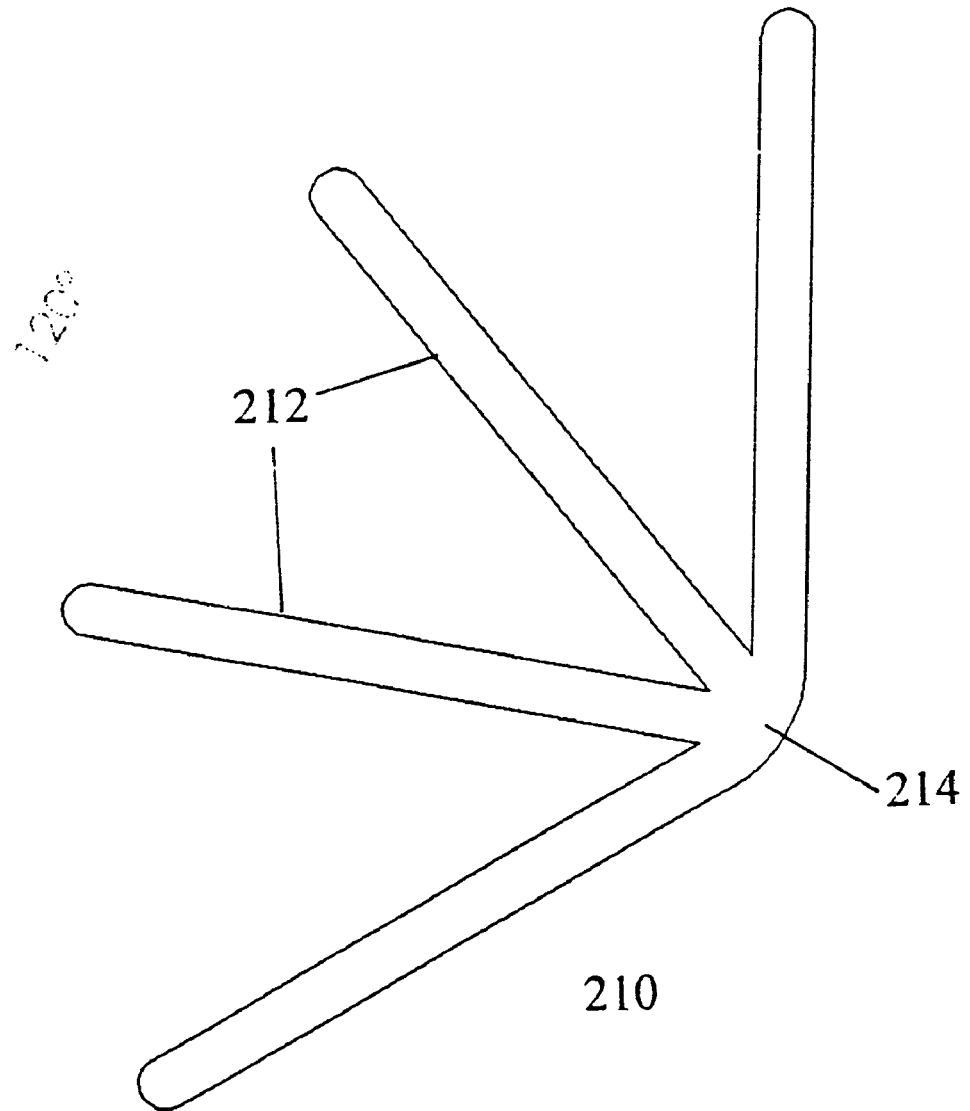
FIG. 25 is an illustration of a different version of the embodiment of the device of the invention depicted in FIG. 24.

The embodiments of the device depicted in FIGS. 24 and 25 may be constructed of any suitable elastic material. Preferably, said embodiments are constructed of metal wires or tubes. Examples of metals possessing the required physical properties include (but are not limited to) stainless steel 316 and NITINOL (Nickel Titanium), both of which are biocompatible metals that are commercially available in the form of wires or tubes. For examples, wires of both materials may be obtained from Allvac Inc., Monroe, N.C.

In the case of wires, industrial bending machinery may be used to bend the wire into the desired shape.

In the case of tubes a "cut out" method may be used. In this type of method, selected areas of the metal of the tube are removed, for example, by laser cutting, until only the desired geometry, shape, and dimensions, remain.

Exemplary dimensions of the embodiments of the device depicted in FIGS. 24 and 25 are as follows: Longitudinal length, (that is, the length extending along imaginary central longitudinal axis, from the top of elongated members 212 to the lower surface of the base element 214 of the device) is in the range of between about 0.5 cm to about 10.0 cm, preferably, about 6 cm. The diameter across the widest end, that is, the distance spanning across the top or free ends of the elastic arms or extensions, is in the range of between about 0.1 cm and about 6.0 cm, preferably, about 3 cm. The angle between any two of the longitudinal elastic arms or extensions can be in the range of 5-180 degrees, preferably about 30 degrees. The average depth or thickness of the metal is in the range of between about 0.01 mm (10 microns) to about 5.0 mm (5000 microns), preferably, about 0.3 mm (300 microns).

Figure 26:
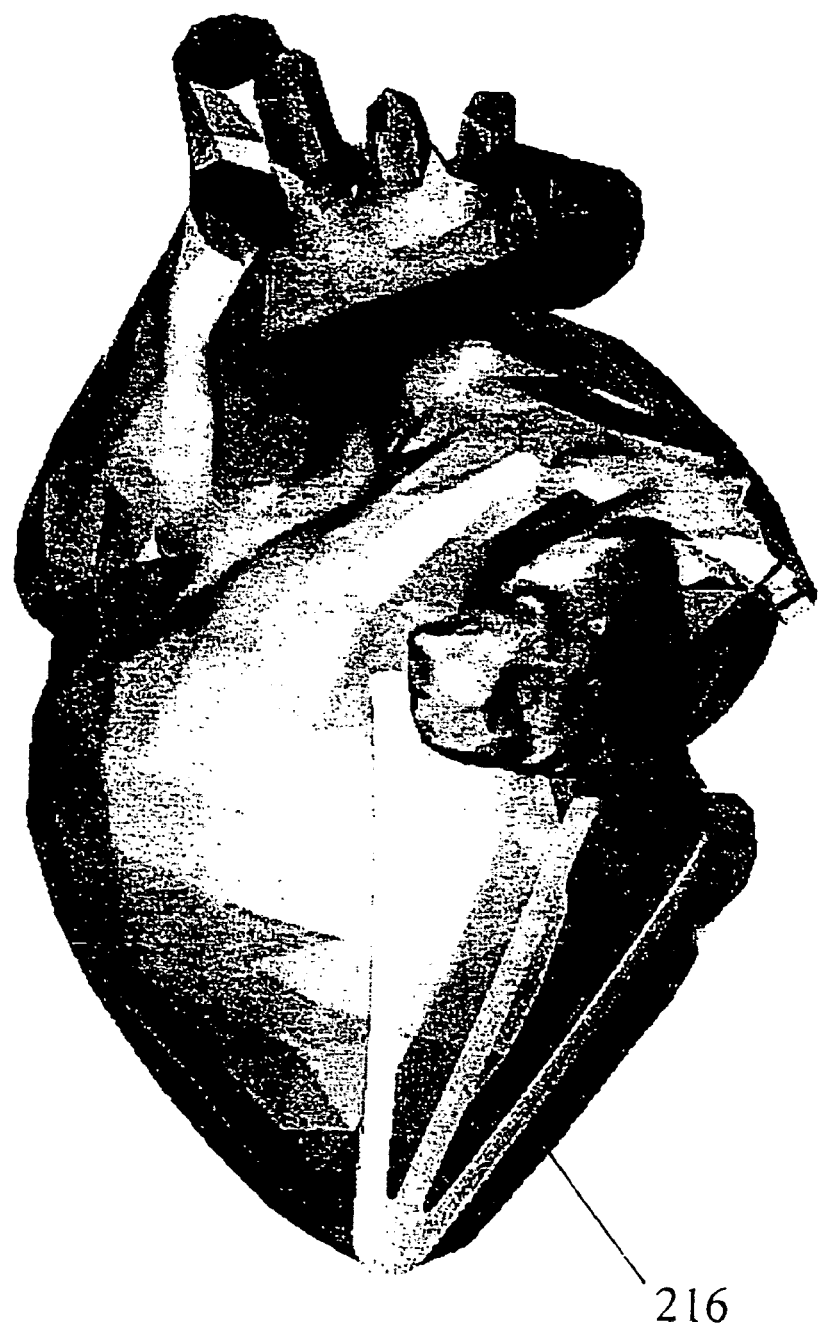
FIG. 26 depicts the device illustrated in FIG. 25 in its in situ position on the external surface of the left ventricle.

FIG. 26 depicts an embodiment of the device described hereinabove (and shown in FIG. 25) in its in situ position on the external surface of the left ventricle 216. The device may be connected or attached to the external surface of the heart by the use of any suitable conventional material or means, including (but not restricted to) biocompatible pins, biocompatible needles, biocompatible spikes, biocompatible screws, biocompatible clamps, biocompatible glue, biocompatible adhesion, surgical sutures, and, combinations thereof, having dimensions of length, height, and, width, depth, or thickness, each on the order of microns to centimeters, in the range of between about 10 microns to about 8 cm. In addition, the present invention also provides certain novel connecting elements that may be used to attach the above-described device to the external surface of the heart in a manner such that said device is held in close apposition to said external surface, thus resulting in maximal transduction of the potential energy of the elastic component into the expansive kinetic energy used to assist in diastolic filling of the left ventricle.

One preferable embodiment of such connecting means includes the use of a plurality of open-ended tubes constructed of a biocompatible material, said tubes being connected to the external surface of the heart by means of surgical sutures or suture clips or any other suitable conventional means, such that said tubes are disposed in an essentially longitudinal orientation. Tubes of any suitable biocompatible material may be used; preferred materials include Dacron and polytetrafluorethylene (PTFE). Preferably, the tubes have an internal diameter in the range of 0.2-1.4 cm and a length in the range of 1-5 cm. Suitable Dacron tubes originally intended for use as arterial grafts are highly suitable for this purpose, and may be commercially obtained from C. R. Bard, Inc., Murray Hill, N.J., USA.

Figure 27:
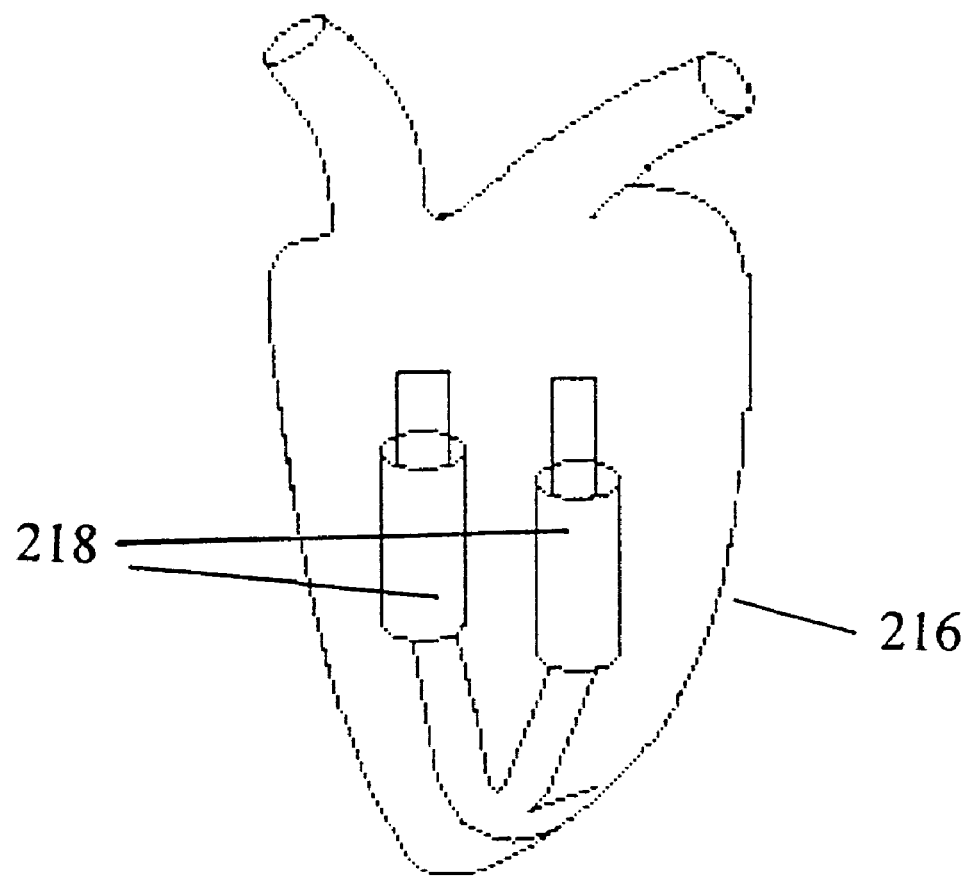
FIG. 27 illustrates the use of Dacron tubes as connecting elements for attaching a device of the invention to the external surface of the heart.

FIG. 27 illustrates an example of the above-described embodiment of the device of the invention that has been attached to the external surface of the left ventricle 216 by means of Dacron tubes 218. Supplementary connecting means (not shown), selected from the group of means and materials given hereinabove (e.g. sutures, glue, pins etc.) are additionally used at discrete points along the device in order to provide extra stabilization of said device in relation to the ventricular surface.

The embodiments of the device of the invention described hereinabove and depicted in FIGS. 24 and 25 may be inserted in place using a minimally invasive surgical procedure, such as a thoracoscopy, or, thoracotomy, with a relatively small diameter delivery system for delivering and deploying the ventricular device into the body, in general, and to a left ventricular cardiac outer wall surface, in particular.

Preferably, base element 214 is self-expanding, in order to facilitate the use of minimally invasive insertion procedures such as those described above.

Figure 28:
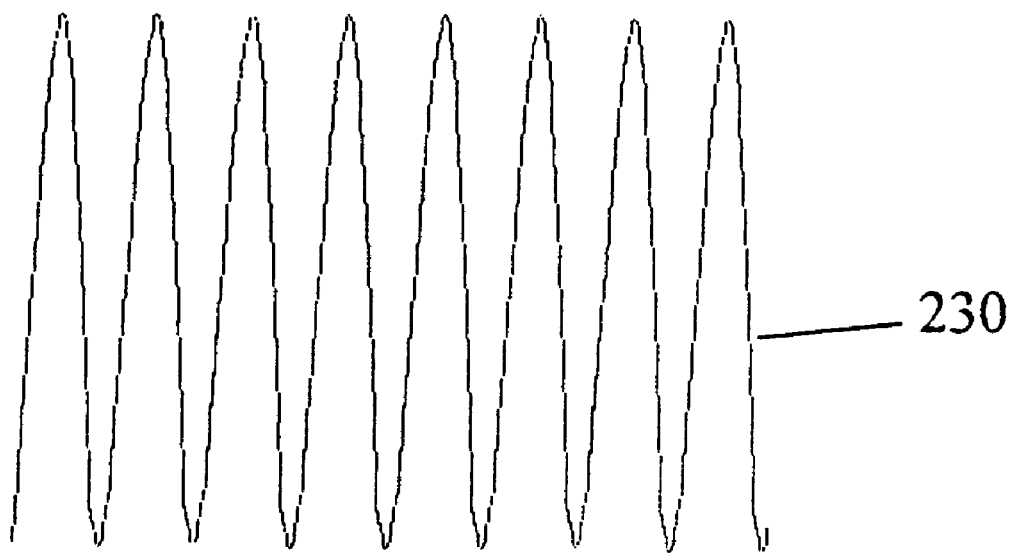
FIG. 28 is a schematic diagram illustrating a two-dimensional view of a further type of exemplary ventricular device for implementing specific case (b) of the first principle preferred embodiment of the method, of positioning the at least one elastic component of the ventricular device adjacent to the outer wall surface of the left ventricle, in accordance with the present invention, wherein the ventricular device comprises an elastic component in the form of a v-shaped wire spring.

In a further preferred embodiment of the device of the invention, the elastic component comprises a wire spring 230, wherein said spring is formed such that it contains along its length one or more angled portions, each of said angled portions being approximately v-shaped or u-shaped, as indicated in FIG. 28. One consequence of using this shape of wire spring as the elastic component is that said elastic component is able to exert tangential as well as radial forces on the external surface of the heart to which it is attached. Thus, the radial forces arise from the bending of the whole spring when it is connected to the surface of the heart, and its envelope shape adapted to the curvature thereof. The tangential forces, on the other hand, are a function of the v-shaped or u-shaped bends of the wire spring.

Figure 29:
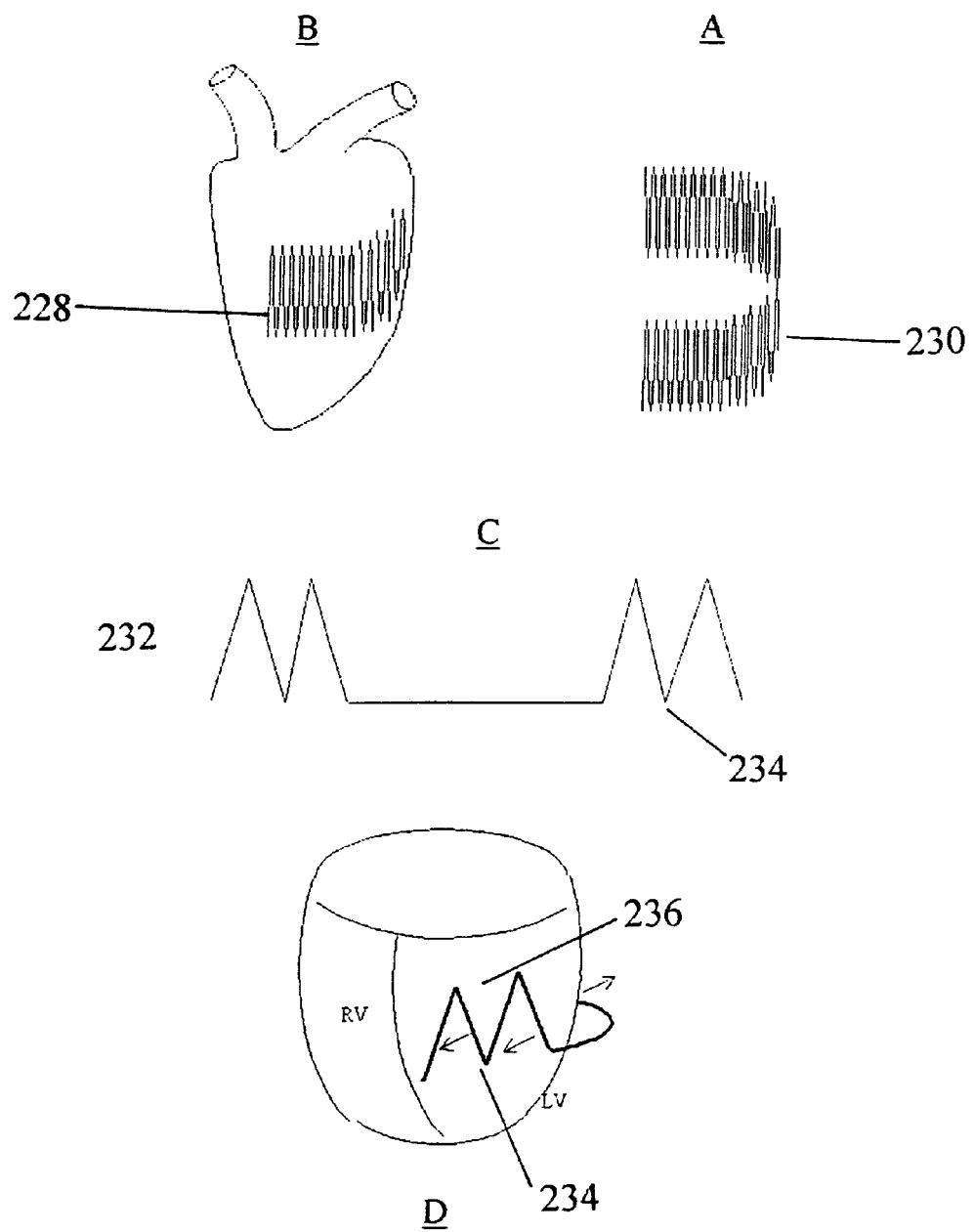
FIG. 29 depicts some examples of in vivo devices of the invention that incorporate a wire spring as their elastic element.

FIG. 29A depicts one example of this embodiment of the invention, wherein the wire spring 230 is formed into a series of v-shaped bends in an uninterrupted manner over its entire length.

FIG. 29B shows the same spring in situ extending over most of the width of the left ventricle of the heart 228.

FIG. 29C illustrates another preferred embodiment of the wire spring type of elastic element for use in accordance with the present invention. It will be noted that in this case, the spring 232 comprises two laterally-placed v-shaped angled sections 234 separated by a linear section.

As indicated in FIG. 29D, this particular embodiment is designed such that when attached to the heart, the angled sections 234 are situated over the lateral portions of the external surface of the left ventricular wall 236. The arrows in this figure indicate the position and direction of the tangentially-directed forces exerted by the angled v-shaped portions of the spring on the left ventricular wall 236.

Figure 30:
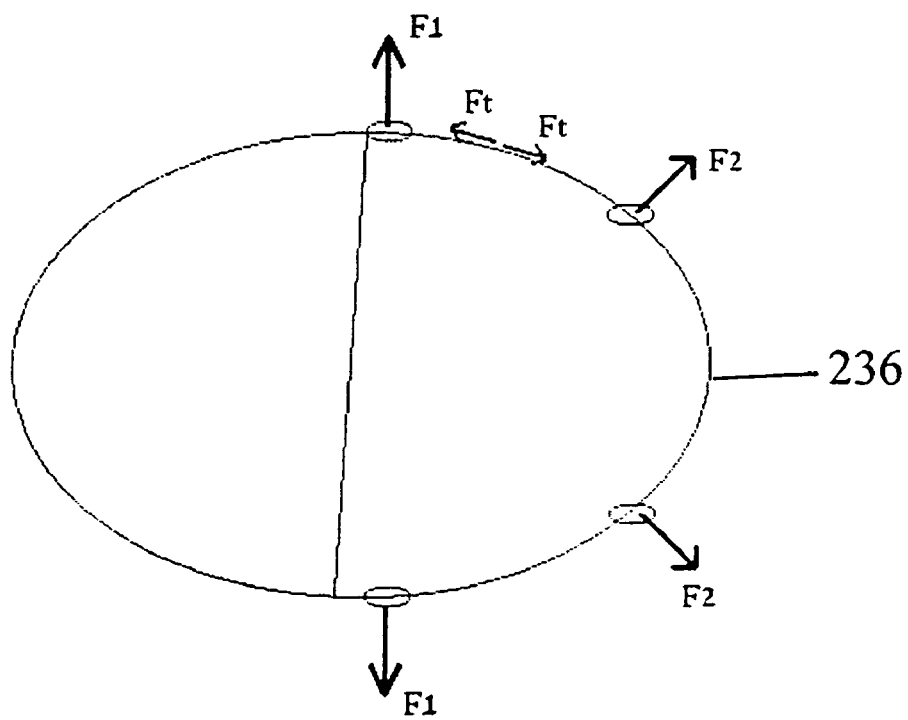
FIG. 30 schematically illustrates the direction of the forces exerted by a device of the invention on the ventricular wall.

FIG. 30 is an illustrative plan view of the heart 228 showing the direction of the forces exerted by the device illustrated in FIG. 29D on the external surface of the left ventricular wall 236. The arrows labeled as F1 indicate the direction of the radial forces acting on the attachment points of the device to the ventricular wall 236 (shown as flattened ellipses). The arrows labeled as F1 indicate the tangentially-directed forces, while the arrows F2 indicate the direction of the vector sum of the various forces acting on the attachment points. It will be seen from this figure that said vector sum direction is in a direction that will lead to an outward expansive (i.e. inflating) movement of the left ventricular wall.

As mentioned hereinabove, the presently-discussed embodiment of the device of the present invention may be connected or attached to the external surface of the heart by the use of any suitable conventional material or means, including (but not restricted to) biocompatible pins, biocompatible needles, biocompatible spikes, biocompatible screws, biocompatible clamps, biocompatible glue, biocompatible adhesion, surgical sutures, and, combinations thereof, having dimensions of length, height, and, width, depth, or thickness, each on the order of microns to centimeters, in the range of between about 10 microns to about 8 cm. In addition, the present invention also provides certain novel connecting elements that may be used to attach the above-described device to the external surface of the heart in a manner such that said device is held in close apposition to said external surface, thus resulting in maximal transduction of the potential energy of the elastic component into the expansive kinetic energy used to assist in diastolic filling of the left ventricle.

Figure 31:
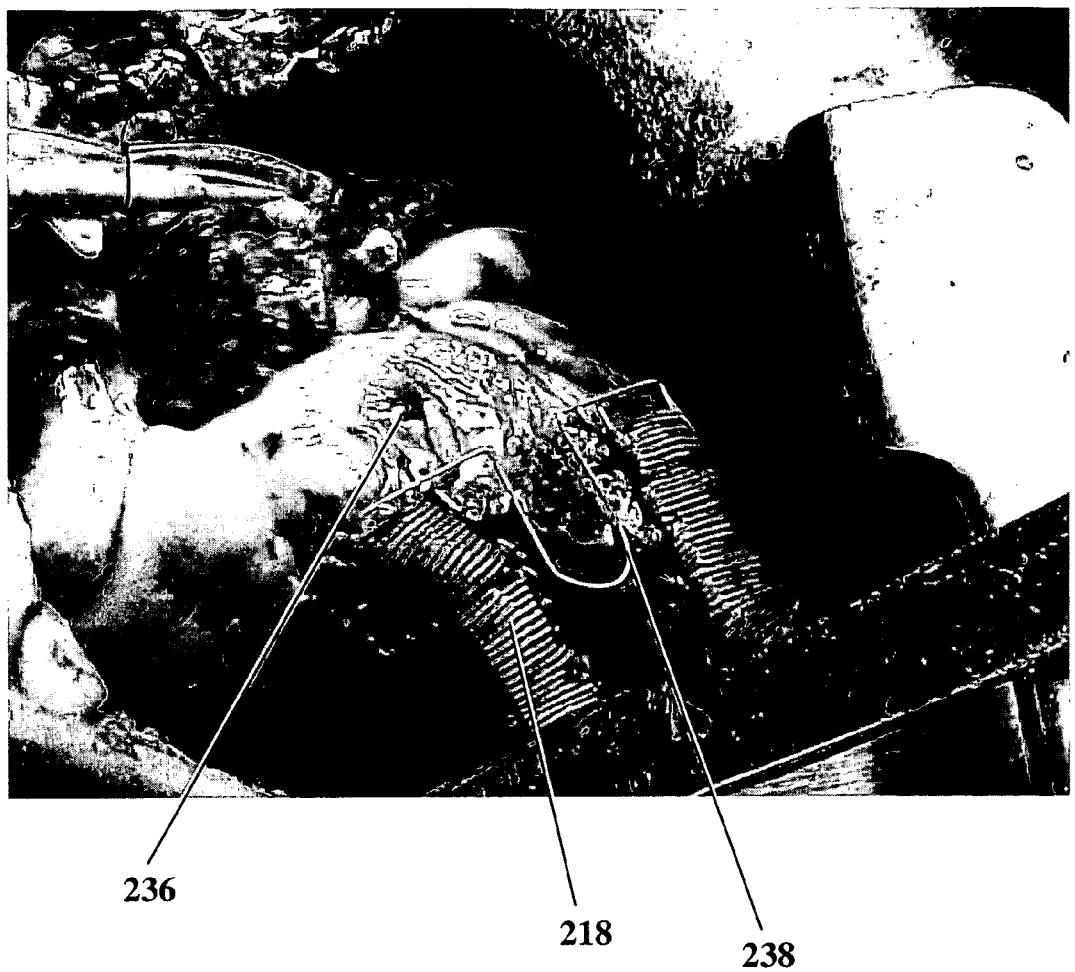
FIG. 31 is a photographic representation of a single wire spring device that has been attached to the left ventricle by means of a pair of Dacron tubes.

One preferable type of connecting means for use with the wire spring embodiment of the presently-described device involves the use of one or more open-ended Dacron or polytetrafluorethylene (PTFE) tubes (as described hereinabove), said tubes being connected to the external surface of the heart by any suitable means including, but not limited to, surgical sutures and suture clips. The tubes are disposed in an essentially longitudinal orientation, such that vertically-orientated end sections of the wire spring can be inserted therein. Preferably, the tubes have an internal diameter in the range of 0.2-1.4 cm and a length in the range of 1-5 cm. FIG. 31 is a photographic representation of a single wire spring device containing a single, medially placed u-shaped angled section, 238 inserted into two Dacron tubes 218 that have been sutured to the external surface of the left ventricular wall 236.

Metal wires used for constructing this embodiment of the device of the invention include (but are not limited to) stainless steel 316 and NITINOL (Nickel Titanium) wires, both of which are biocompatible and are readily available from commercial suppliers (e.g. Allvac Inc., Monroe, N.C.). Preferably, wires having diameters in the range of 0.1 mm to 2 mm are used in the construction of the wire spring device.

The presently-discussed embodiment may be manufactured by taking a 10-40 cm length of metal wire and bending it into the desired shape (e.g. as depicted in FIGS. 29A-29D) by means of a wire bending jig, a hand bending with pliers and vice or industrial wire bending equipment. For example, in the case of hand bending, the exact desired configuration may be first marked on millimetric paper, after which the wire may be manually bended using pliers at one end of the wire and an instrument to stabilize the second end of the wire. For large scale production, industrial wire bending equipment may be used.

In addition to the connecting means described hereinabove, the present invention also encompasses the use of several other types of connecting elements which may be used for connecting the various embodiments of the presently-claimed in vivo device to the external ventricular wall.

Figure 32:
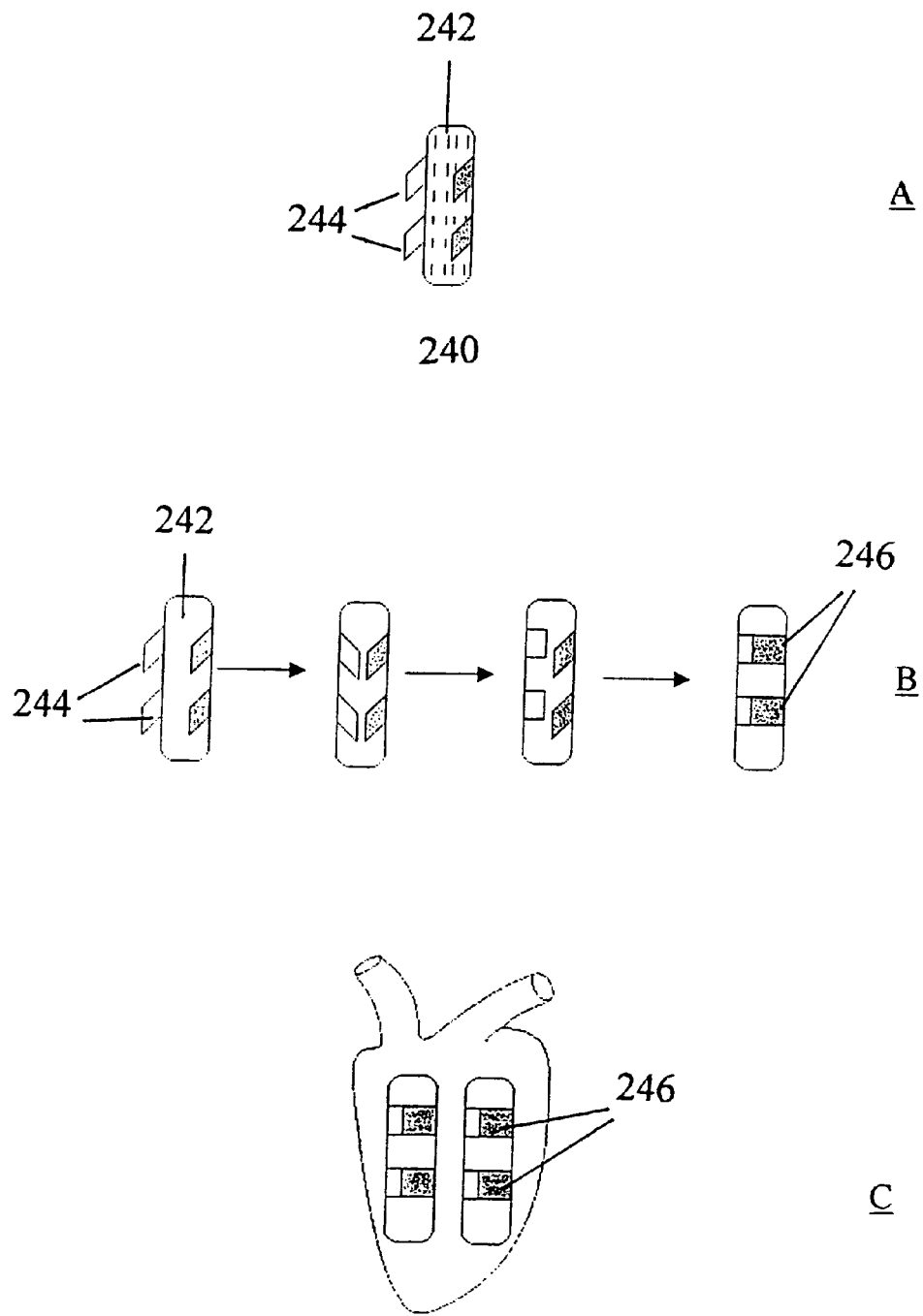
FIG. 32 schematically illustrates a cardiac girdle type of connecting element. The basic structure of the girdle is depicted in FIG. 32A. The loops formed by the union of pairs of contralateral tabs are shown in FIG. 32B.

One such type of connecting element is the cardiac girdle depicted in FIG. 32. As shown in FIG. 32A, the cardiac girdle 240 comprises a thin patch 242 which may be attached to the external surface of the ventricular wall. Extending laterally from said patch is a plurality of tabs or straps 244, arranged in contralateral pairs. In a preferred embodiment, the cardiac girdle comprises two such contralateral pairs of tabs. The length of each tab is such that it can overlap with its contralateral partner, thus forming a loop 246, as shown in FIG. 32B. The thin patch element of the cardiac girdle is adhered to the external LV wall by means of suturing, gluing or pinning, and the loops formed by each contralateral pair of tabs are used to grip portions of the in vivo device. The patch may be orientated on the external ventricular wall such that said loops, once formed, are arranged in either an essentially horizontal or an essentially vertical orientation. The cardiac girdle may thus be used to grip either horizontally-disposed or vertically-disposed members of the in vivo device. FIG. 32C illustrates the use of two cardiac girdles that have been attached to the external surface of the left ventricular wall such that the loops 246 are orientated horizontally, thus allowing each of said girdles to grip a vertically-disposed longitudinal member of a device of the invention.

The cardiac girdle may be made from any suitable biocompatible material. Examples of such materials include Dacron and polytetrafluorethylene (PTFE), both of which possess the required mechanical strength in order to function as connecting means, and which may be woven into meshes.

A cardiac girdle, as described above, may be inserted into the thoracic cavity and used to connect an in vivo device of the invention to the external ventricular wall in the following manner:

The heart is surgically exposed following midline sternotomy and pericardiotomy. The heart is then measured in various dimensions (apex to base, circumference at base and midway between base and apex) in order to assist with selection of an in vivo device and cardiac girdle of an appropriate size. The girdle may then be attached to the external ventricular wall by means of pinning, gluing or suturing. In the latter case, the cardiac girdle is sutured to the myocardium using multiple partial-thickness (deep) interrupted stitches, taking care not to compromise any of the epicardial coronary arteries. When pinning is used, the fabric may be attached to the myocardium using multiple star-like, splitting non-retractable tacking pins, avoiding the epicardial coronary arteries. The in vivo device, constricted temporarily to the heart size by means of a constriction mechanism, is now positioned on the external surface of the heart and locked within the girdle by means of closure of the aforementioned tabs or straps, to form retaining loops. The constriction mechanism is removed from the device to allow the device to exert expansive and tangential forces on the external ventricular wall. Following attachment of the girdle and device, the heart is observed in order to ascertain that detachment of the fabric patch of the girdle from the myocardium has not occurred at any point. Final fixation of the device within the girdle is now performed using interrupted stitches.

Figure 33:
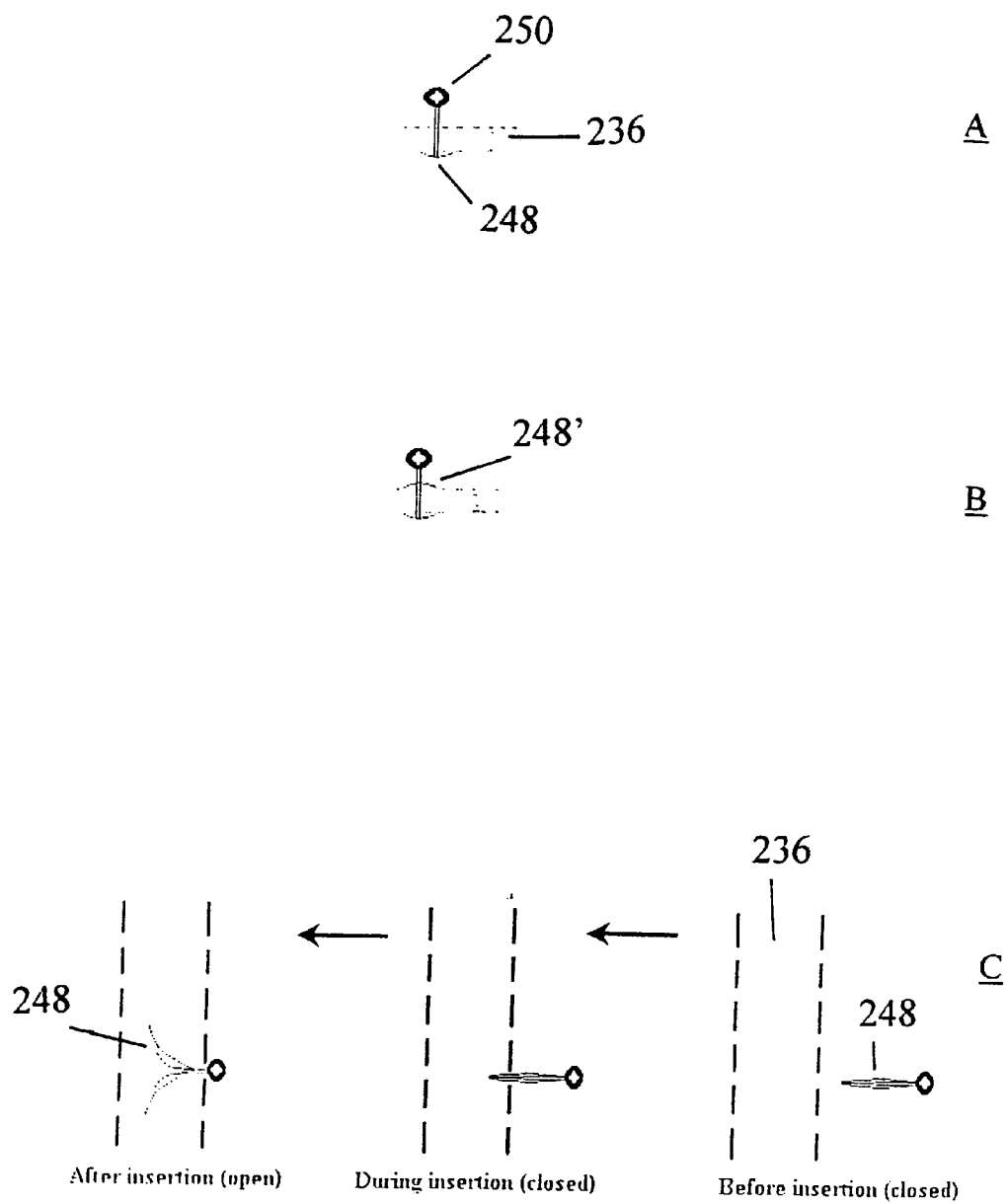
FIG. 33 illustrates a connecting element of the type known as a cardiac anchor. In the embodiment shown in FIG. 33A, the anchor is provided with transmural attachment.

Another type of connecting element is the cardiac anchor, three preferred embodiments of which are illustrated in FIG. 33. Each anchor is composed of the following two main elements:

1. A wall-connecting element 248 for attachment of the anchor to the left ventricular wall. This element may be connected to said ventricular wall by a transmural or an intramural attachment mechanism. In addition, the wall-connecting element may also be attached to the ventricular wall by means of biocompatible glue, pins, hooks, sutures or any other convenient means.

2. A device-connecting element 250 for attachment of an in vivo device of the present invention to the anchor. This element may take one of several different forms including, for example, a ring, into which the device is attached or sutured. It may also incorporate a locking mechanism. In addition, biocompatible glue, pins, hooks or sutures etc. may also be used for attaching the anchor to the in vivo device.

Figure 34:
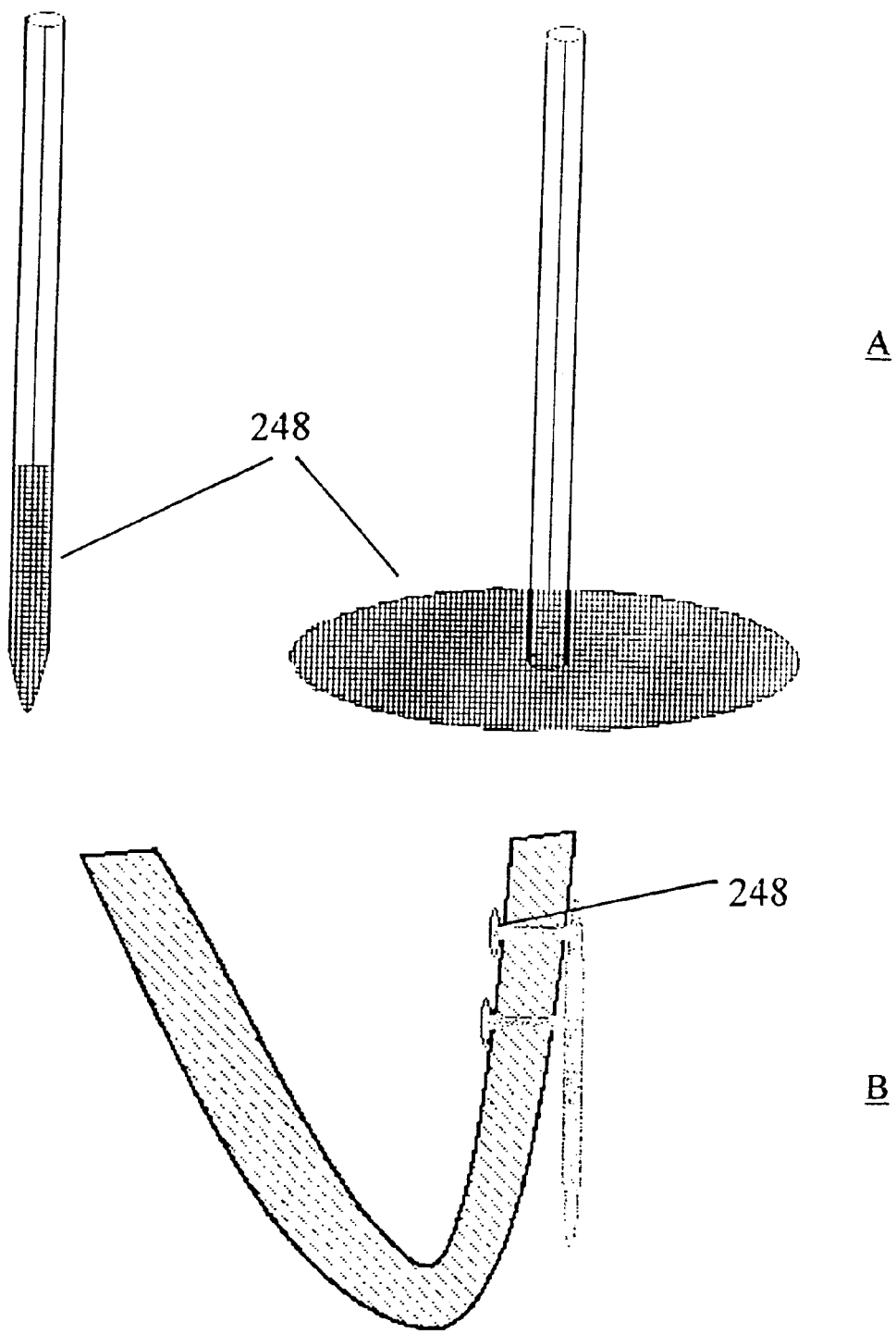
FIG. 34 depicts an expandable transmural anchor.

In one preferred embodiment, as illustrated in FIG. 33A, the anchor is provided with transmural attachment, wherein the wall-connecting element 248 is located on the inner side of the left ventricular wall 236 (i.e. within the ventricular cavity), while the device-connecting element 250 is situated external to said ventricular wall. Preferably, this embodiment of the anchor is provided in the form of an expandable transmural anchor, as shown in FIG. 34A. In this case, the anchor is inserted into the left ventricular wall while in its closed, or retracted, condition. Once the wall-connecting element 248 of said anchor has passed through the ventricular wall and becomes located within the ventricular cavity, said wall-connecting element is opened, by means of, for example small spring elements, thus fixing the anchor to the ventricular wall 236, as shown in FIG. 34B.

In another preferred embodiment (FIG. 33B), the transmural anchor is further provided with a second wall-connecting element 248' which, after insertion of said anchor into the ventricular wall 236, becomes situated on the external surface of said wall. In this way, the anchor is stabilized by virtue of the fact that the ventricular wall becomes "sandwiched" between the two wall-connecting elements.

FIG. 33C illustrates a third, intramural, embodiment of the cardiac anchor. In this case, the anchor is inserted into the ventricular wall 236, from the external side, in a closed state. Once the anchor has reached the required depth within the ventricular wall, the wall-connecting element 248 is opened, by means of, for example, spring elements (not shown), thus embedding said wall-connecting element within the ventricular myocardium.

A particular advantage of the cardiac anchor connecting element is the fact that a series of such elements may be used to connect a plurality of in vivo devices (for example wire spring devices as described hereinabove) to the external ventricular wall. In this case, each of such spring devices is attached by its lateral ends to the heart by means of a pair of cardiac anchors. Each individual device will then be able to exert forces on its anchor pair, in such a way as to increase the linear separation distance between each member of said pair. Consequently, when the anchors are brought closer to each other during systolic movement of the ventricle, the spring will be compressed, thus storing potential energy. During diastole, this potential energy will be released as kinetic energy, thereby exerting radial expansive and tangential forces on the external wall of the filling ventricle. For example, the spring may be connected to its anchor pair during end diastole (when the left ventricle is filled to its greatest extent). During systolic contraction of the heart muscle, such a spring will be placed in a compressed state, absorbing potential energy, which in turn will be transformed into kinetic energy during the diastolic phase, thereby assisting in the filling of the left ventricle.

A further advantage of the cardiac anchor element, as described hereinabove, is the fact that it permits the presently disclosed and claimed in vivo devices to be used with a range of different sized hearts, and/or in hearts with aberrant morphology. For example, if a coronary artery is found to be located in an unusual position which might otherwise interfere with the placement of an in vivo device of the invention, said device can be conveniently positioned away from said artery.

In addition to the anatomical flexibility which is acquired by the use of cardiac anchors as connecting elements, said anchors further permit the use of standard in vivo devices for treating ventricles that require either relatively small or relatively large diastolic-assisting forces to be exerted thereon. This is achieved by varying the number of cardiac anchors attached to the ventricular wall, thereby permitting flexibility in the number of spring devices that may be anchored therein. Due to the ease with which the anchors and spring devices may be added, it is possible to continuously monitor the effect of the device on ventricular pressure changes, and to alter the number of springs used in response to said monitoring.

Another advantage of the cardiac anchors described herein is the fact that, due to their small size and elongated shape, they may be easily inserted into an endoscopic delivery mechanism, thus enabling the insertion of the in vivo device of the invention by use of minimally-invasive methods.

A further, significant, advantage of the use of cardiac anchors as the connecting means for the in vivo devices of the present invention is related to the fact that said anchors may be attached to the ventricular wall in various different geometries. Typically, a line of such cardiac anchors may be arranged in a horizontally-disposed line, thus exerting tangential forces on the ventricular wall in a horizontal direction. However, if so required, the anchors may be so attached such that the device is orientated in other directions, thus permitting said device to exert tangential forces in said other directions, in accordance with individual clinical requirements.

As previously stated above, in the general description of the first principle preferred embodiment of the method and device, applicable to each specific case (a)-(d), in alternative embodiments, the ventricular device further includes at least one non-elastic component or mechanism, which operatively functions together with other elements or components of the ventricular device for optimally effecting the elastic functionality of the ventricular device, while minimally disturbing systolic function of the heart.

Accordingly, in alternative embodiments, for implementing specific case (b) of the first principle preferred embodiment of the method and device, ventricular device or elastic component 70 (e.g. FIG. 12), in general, further includes at least one non-elastic component or mechanism for anchoring, adhering, and/or, attaching, at least one part or region of ventricular device 70 to at least one part of the outer wall surface of the left ventricle where ventricular device 70 is configured for in-vivo elastic operation.

Specific types, and materials of construction, geometry, shape, form, and, dimensions, of the at least one anchoring, adhering, and/or, attaching, component or mechanism are described in the general description, above, and are applicable to ventricular device 70 of specific case (b). In particular, the two exemplary types, non-transmural and transmural, of anchoring, adhering, and/or, attaching, mechanisms applicable to ventricular device 10 of specific case (a), previously described and illustrated in FIGS. 10A and 10B, respectively, are also applicable to ventricular device or elastic component 70 of specific case (b).

For specific case (b) of the method and device, where the ventricular device, for example, ventricular device or elastic component 70, 80, or, 82, is connected to at least one part of the outer wall surface of the left ventricle, following inserting and maneuvering of the ventricular device inside the thoracic cavity, the ventricular device is connected to the outer wall surface of the left ventricle. Connecting, by way of anchoring, adhering, and/or, attaching, the ventricular device, including the at least one elastic component, is performed by using at least one anchoring, adhering, and/or, attaching, mechanism, included as part of the ventricular device, as previously described above, and/or, separate from the ventricular device.

For specific case (b) of the method and device, the ventricular device is inserted into place by using a minimally invasive surgical procedure, such as thoracoscopy, or, thoracotomy, with a relatively small diameter delivery system for delivering and deploying the ventricular device into the body, in general, and to a left ventricular cardiac outer wall surface, in particular.

Techniques and equipment of thoracoscopy deployment are well taught about in the prior art, however, for enabling implementation of the method and device of the present invention, an example is provided herein. FIG. 15 is a schematic diagram illustrating an example of a thoracoscopic delivery system 90 for implementing specific case (b) of the method and device. Delivery system 90 is basically structured as a three layered sleeve. Ventricular device 70 is supported between an inner support sleeve 92, an outer support sleeve 94, and, an axial support sleeve 96, which prevents ventricular device 70 from slipping backwards. Delivery system 90 is maneuvered and placed in the body so that it envelops the heart 84, and, after maneuvering and positioning ventricular device 70 in place, inner support sleeve 92 is gradually retracted out, while outer support sleeve 94 is used to compress ventricular device 70 towards the ventricular outer wall surface. At this stage, ventricular device 70 is connected to the outer wall surface of the left ventricle, followed by withdrawing outer support sleeve 94 and axial support sleeve 96.

As previously stated above, in Step (a), in specific case (c) of the first principle preferred embodiment of the method and device, the ventricular elastic device includes at least one component featuring the physicochemical property and behavior of elasticity, whereby, the at least one elastic component of the device is positioned adjacent to at least one part of intermediate wall region of the left ventricle, and potentially exerts a radially outward, elastic, pulling and pushing type of the expansive force or pressure to the intermediate wall region of the left ventricle for reducing intracardiac hydrostatic pressure during ventricular diastole of the heart, thereby, improving diastolic function of the left ventricle of the heart, while minimally disturbing systolic function of the heart.

FIG. 16 is a schematic diagram illustrating a cross sectional view of the exemplary 'U' shaped ventricular device 26 of FIGS. 3A and 3B, for implementing specific case (c) of the first principle preferred embodiment of the method and device, of positioning the at least one elastic component of the ventricular device adjacent to the intermediate wall region of the left ventricle. As previously described above, with reference to FIGS. 3A and 3B, ventricular device 26 is designed, configured, and constructed, as an integral single, continuous, elastic component, featuring a plurality of two elastic arms or extensions 12 which are essentially of the same geometry, shape, and dimensions, and, are either symmetric or asymmetric relative to central longitudinal axis 18 (FIG. 3A). Lower end regions 16 of elastic arms or extensions 12 of ventricular device 26 are integral and continuous with each other without the presence of optional elastic lower basal section or ring formation (14 in FIGS. 2A and 2B). Accordingly, in this specific case (c), ventricular device or elastic component 26, including elastic arms or extensions 12, is positioned adjacent to intermediate wall region 52 of left ventricle 28. In FIG. 16, intermediate wall region 52 refers to ventricular wall region intermediate to, or in between, inner wall surface 50 of left ventricle 28 and outer wall surface 56 of left ventricle 28. In FIG. 16, ventricular device 26 is illustrated in a 'rest' position, that is, in a position whereby ventricular device 26 potentially applies a radially outward, elastic, pulling and pushing type of the expansive force or pressure to intermediate wall region 52 of left ventricle 28.

As previously stated above, in Step (a), in specific case (d) of the first principle preferred embodiment of the method and device, the ventricular elastic device includes at least one component featuring the physicochemical property and behavior of elasticity, whereby, the at least one elastic component of the ventricular device is positioned adjacent to at least one part of intermediate wall region of the left ventricle, and potentially exerts a radially outward, elastic, pulling and pushing type of the expansive force or pressure to the intermediate wall region of the left ventricle, and, is positioned adjacent to at least one part of inner wall surface of the left ventricle, and potentially exerts a radially outward, elastic, pushing type of the expansive force or pressure to the inner wall surface of the left ventricle, for reducing intracardiac hydrostatic pressure during ventricular diastole of the heart, thereby, improving diastolic function of the left ventricle of the heart, while minimally disturbing systolic function of the heart.

FIG. 17 is a schematic diagram illustrating a cross sectional view of the exemplary 'U' shaped ventricular device 26 of FIG. 3A, for implementing specific case (d) of the first principle preferred embodiment of the method and device, of positioning ventricular device or elastic component 26 adjacent to intermediate wall region 52 of left ventricle 28, and, adjacent to inner wall surface 50 of left ventricle 28. In FIG. 17, ventricular device 26 is illustrated in a 'rest' position, that is, in a position whereby ventricular device 26 potentially applies a radially outward, elastic, pulling and pushing type of the expansive force or pressure to intermediate wall region 52 of left ventricle 28, and, potentially applies a radially outward, elastic, pushing type of the expansive force or pressure to inner wall region 50 of left ventricle 28.

Many alternative specific embodiments of exemplary 'U' shaped ventricular device 26, consistent with the function/structure description of exemplary ventricular device 10 (FIGS. 2A and 2B), above, are clearly possible, for implementing above described and illustrated specific case (c), or, specific case (d), of the first principle preferred embodiment of the method and device.

Additionally, for specific case (c), or, specific case (d), ventricular device or elastic component 26 has variable geometry, shape, form, and, dimensions, and, elastic strength, which, as previously indicated above, are specifically determined, in part, according to actual or measured dynamical (variable) geometry, shape, form, and, dimensions of an actual functioning heart, in general, and, of an actual functioning left ventricle, in particular, and, are also specifically determined, in part, according to the desired or necessary extent or degree of elasticity, for properly and optimally performing the critical function of potentially exerting a radially outward, elastic, pulling and pushing type of the expansive force or pressure (in a range of about 5-20 mm Hg, preferably, about 10 mm Hg) to the intermediate wall region of the left ventricle (specific case (c)), or, potentially exerting a radially outward, elastic, pulling and pushing type of the expansive force or pressure (in a range of about 5-20 mm Hg, preferably, about 5 mm Hg) to the intermediate wall region of the left ventricle, and, a radially outward, elastic, pushing type of the expansive force or pressure (in a range of about 5-20 mm Hg, preferably, about 5 mm Hg) to the inner wall surface of the left ventricle (specific case (d)), in order to properly fulfill the main objective of sufficiently reducing intracardiac hydrostatic pressure during ventricular diastole of the heart, thereby, improving, diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

As previously stated above, in the general description of the first principle preferred embodiment of the method and device, applicable to each specific case (a)-(d), in alternative embodiments, the ventricular device further includes at least one non-elastic component or mechanism, which operatively functions together with other elements or components of the ventricular device for optimally effecting the elastic functionality of the ventricular device, while minimally disturbing systolic function of the heart.

Accordingly, in alternative embodiments, for implementing specific case (c), or, specific case (d), of the first principle preferred embodiment of the method and device, ventricular device or elastic component 26 (FIG. 16, or, FIG. 17, respectively), in general, further includes at least one non-elastic component or mechanism for anchoring, adhering, and/or, attaching, at least one part or region of ventricular device 26 to at least one part of the intermediate wall region of the left ventricle (specific case (c)), or, to at least one part of the intermediate wall region of the left ventricle and to at least one part of the inner wall surface of the left ventricle (specific case (d)), where ventricular device 26 is configured for in-vivo elastic operation.

Specific types, and materials of construction, geometry, shape, form, and, dimensions, of the at least one anchoring, adhering, and/or, attaching, component or mechanism are described in the general description, above, and are applicable to ventricular device 26 of specific case (c), or, specific case (d). In particular, the two exemplary types, non-transmural and transmural, of anchoring, adhering, and/or, attaching, mechanisms applicable to ventricular device 10 of specific case (a), previously described and illustrated in FIGS. 10A and 10B, respectively, are also applicable to ventricular device or elastic component 26 of specific case (c), or, specific case (d). Connecting, by way of anchoring, adhering, and/or, attaching, the ventricular device, including the at least one elastic component, is performed by using at least one anchoring, adhering, and/or, attaching, mechanism, included as part of the ventricular device, as previously described above, and/or, separate from the ventricular device.

For specific case (c), or, specific case (d), of the first principle preferred embodiment of the method and device, the ventricular device is inserted into place by using a minimally invasive surgical procedure, such as catheterization, thoracoscopy, or, thoracotomy, with a relatively small diameter delivery system for delivering and deploying the ventricular device into the body, in general, and, to a left ventricular cardiac intermediate wall region (specific case (c)), or, to a left ventricular cardiac intermediate wall region and to a left ventricular cardiac inner wall surface (specific case (d)), in particular.

In the second principle preferred embodiment of the method and device, in general, the ventricular device includes at least one component featuring the physicochemical property and behavior of magnetic repulsion, whereby, the at least one magnetic component of the ventricular device is positioned adjacent to at least one part of wall region of the left ventricle, and potentially exerts a radially outward, magnetic repulsion, pushing, pulling, or, pulling and pushing, type of the expansive force or pressure to the wall region of the left ventricle, for reducing intracardiac hydrostatic pressure during ventricular diastole of the heart, thereby, improving diastolic function of the left ventricle of the heart, while minimally disturbing systolic function of the heart.

For this embodiment, the wall region of the left ventricle is selected from the group consisting of inner wall surface of the left ventricle, outer wall surface of the left ventricle, intermediate wall region of the left ventricle, and, combinations of wall regions of the left ventricle thereof. Inner wall surface of the left ventricle refers to ventricular wall surface facing inside the cavity of the left ventricle. Outer wall surface of the left ventricle refers to ventricular wall surface facing outside of the left ventricle. Intermediate wall region refers to ventricular wall region intermediate to, or in between, the inner wall surface of the left ventricle and the outer wall surface of the left ventricle. Alternatively stated, but of equal meaning, intermediate wall region refers to ventricular wall region 'inside' the wall of the left ventricle. For the wall region of the left ventricle, used for the adjacent positioning of the at least one magnetic component, being a combination of wall regions, a first exemplary combination is the intermediate wall region of the left ventricle and the inner wall surface of the left ventricle, and, a second exemplary combination is the outer wall surface of the left ventricle and the intermediate wall region of the left ventricle. It is clear to one skilled in the art that there are several additional combinations of the wall region of the left ventricle, which can be used for the adjacent positioning of the at least one magnetic component of the ventricular device.

In a first specific case, herein, referred to as specific case (a), of the second principle preferred embodiment of the method and device, the ventricular device includes at least one component featuring the physicochemical property and behavior of magnetic repulsion, whereby, the at least one magnetic component of the ventricular device is positioned adjacent to at least one part of inner wall surface of the left ventricle, and potentially exerts a radially outward, magnetic repulsion, pushing type of the expansive force or pressure to the inner wall surface of the left ventricle, for reducing intracardiac hydrostatic pressure during ventricular diastole of the heart, thereby, improving diastolic function of the left ventricle of the heart, while minimally disturbing systolic function of the heart.

In a second specific case, herein, referred to as case (b), of the second principle preferred embodiment of the method and device, the ventricular device includes at least one component featuring the physicochemical property and behavior of magnetic repulsion, whereby, the at least one magnetic component of the ventricular device is positioned adjacent to at least one part of outer wall surface of the left ventricle, and potentially exerts a radially outward, magnetic repulsion, pulling type of the expansive force or pressure to the outer wall surface of the left ventricle, for reducing intracardiac hydrostatic pressure during ventricular diastole of the heart, thereby, improving diastolic function of the left ventricle of the heart, while minimally disturbing systolic function of the heart.

In a third specific case, herein, referred to as case (c), of the second principle preferred embodiment of the method and device, the ventricular device includes at least one component featuring the physicochemical property and behavior of magnetic repulsion, whereby, the at least one magnetic component of the ventricular device is positioned adjacent to at least one part of intermediate wall region of the left ventricle, and potentially exerts a radially outward, magnetic repulsion, pulling and pushing type of the expansive force or pressure to the intermediate wall region of the left ventricle, for reducing intracardiac hydrostatic pressure during ventricular diastole of the heart, thereby, improving diastolic function of the left ventricle of the heart, while minimally disturbing systolic function of the heart.

In the second principle preferred embodiment of the method and device, generally applicable to each specific case (a)-(c), the ventricular device is preferably designed, configured, and constructed, in a manner whereby the at least one magnetic component of the ventricular device features at least two separated bipolar magnetic elements, or magnets, each having two opposite magnetic poles of a north pole and a south pole, and same poles of the at least two magnetic elements, or, magnets, are positioned facing each other for generating the radially outward, magnetic repulsion, pushing, pulling, or, pulling and pushing, type of the expansive force or pressure to the wall region of the left ventricle, for reducing intracardiac hydrostatic pressure during ventricular diastole of the heart, thereby, improving diastolic function of the left ventricle of the heart, while minimally disturbing systolic function of the heart.

The ventricular device of each specific case (a)-(c), in general, and, the at least one magnetic component as a single entity, or, each of the at least two separated magnetic elements or magnets as a plurality of each magnetic component, in particular, are constructed from a single type of material, or, from a plurality of different types of materials. More specifically, the ventricular device, in general, and, the at least one magnetic component, in particular, are constructed from a single type of material, or, from a plurality of different types of materials, exhibiting the physicochemical property and behavior of magnetic repulsion. For example, such material is selected from the group consisting of a pure magnetic metal, a magnetic metal alloy, and, combinations thereof. Exemplary pure magnetic metals are iron, nickel, and, cobalt. Exemplary magnetic metal alloys are rare earth alloys featuring magnetic properties and behavior, such as neodymium iron boron (NdFeB), and, samarium cobalt (SmCo).

The ventricular device of each specific case (a)-(c), in general, and, the at least one magnetic component as a single entity, or, each of the at least two separated magnetic elements or magnets as a plurality of each magnetic component, in particular, are wrapped or enclosed inside a single type of material, or, inside a plurality of different types of materials. More specifically, the ventricular device, in general, and, the at least one magnetic component, in particular, are wrapped or enclosed inside a single type of material, or, inside a plurality of different types of materials, having variable geometry, shape, form, and, dimensions, exhibiting physicochemical properties and behavior which are (1) non-interfering, additive, or, synergistic, with the magnetic repulsion functionality of the ventricular device during in-vivo operation in the heart, (2) minimally disturbing to the overall functionality of the heart during the cardiac cycle, and, (3) biocompatible.

The ventricular device of each specific case (a)-(c), in general, and, the at least one magnetic component as a single entity, or, each of the at least two separated magnetic elements or magnets as a plurality of each magnetic component, in particular, have variable geometry, shape, form, and, dimensions, which are specifically determined, in part, according to actual or measured dynamical (variable) geometry, shape, form, and, dimensions of an actual functioning heart, in general, and, of an actual functioning left ventricle, in particular.

The variable geometry, shape, and, form, of the ventricular device of each specific case (a)-(c), in general, and, the at least one magnetic component as a single entity, or, each of the at least two separated magnetic elements or magnets as a plurality of each magnetic component, in particular, are characterized by at least one physical aspect or descriptor selected from the group consisting of linear, straight, non-linear, curved, curvilinear, angular, planar, non-planar, branched, thick, coarse, thin, fine, long, short, and, combinations thereof.

The variable geometry, shape, and, form, of the ventricular device of each specific case (a)-(c), in general, and, the at least one magnetic component as a single entity, or, each of the at least two separated magnetic elements or magnets as a plurality of each magnetic component, in particular, are characterized by at least one physical aspect or descriptor selected from the group consisting of circular, disc, conical, spherical, spheroidal, elliptical, ellipsoidal, parabolic, parabaloidal, hyperbolic, hyperpoloidal, spiral, helical, polygonal such as triangular, square, and, rectangular, and, combinations thereof.

The variable geometry, shape, and, form, of the ventricular device of each specific case (a)-(c), in general, and, the at least one magnetic component as a single entity, or, each of the at least two separated magnetic elements or magnets as a plurality of each magnetic component, in particular, are characterized by at least one physical aspect or descriptor selected from the group consisting of integral, non-integral, continuous, discontinuous or non-continuous, contiguous, discontiguous or non-contiguous, and, combinations thereof.

The variable geometry, shape, and, form, of the ventricular device of each specific case (a)-(c), in general, and, the at least one magnetic component as a single entity, or, each of the at least two separated magnetic elements or magnets as a plurality of each magnetic component, in particular, are characterized by at least one physical aspect or descriptor selected from the group consisting of a variable extent or degree of symmetry, a variable extent or degree of asymmetry, and combinations thereof.

Surfaces and volumes of the variable geometry, shape, and, form, of the ventricular device of each specific case (a)-(c), in general, and, the at least one magnetic component as a single entity, or, each of the at least two separated magnetic elements or magnets as a plurality of each magnetic component, in particular, are characterized by at least one physical aspect or descriptor selected from the group consisting of smooth, flat, rough, ridged or bumpy, jagged, wavy, saw-toothed, bent, planar, non-planar, closed, open, completely solid featuring no cut-out or hollow pattern, incompletely solid featuring a cut-out or hollow pattern such as a cellular, net, or beehive, type of cut-out or hollow pattern, and, combinations thereof.

Furthermore, the ventricular device of each specific case (a)-(c), in general, and, the at least one magnetic component as a single entity, or, each of the at least two separated magnetic elements or magnets as a plurality of each magnetic component, in particular, have dimensions of length, height, and, width, depth, or thickness, each on the order of microns to centimeters, in the range of between about 10 microns to about 8 cm.

Additionally, in the second principle preferred embodiment of the method and device, generally applicable to each specific case (a)-(c), the variable geometry, shape, form, and, dimensions, and, magnetic strength, of the ventricular device, in general, and, the at least one magnetic component as a single entity, or, each of the at least two separated magnetic elements or magnets as a plurality of each magnetic component, in particular, are also specifically determined, in part, according to the desired or necessary extent or degree of magnetic repulsion, for properly and optimally performing the critical function of potentially exerting a radially outward, magnetic repulsion, pushing, pulling, or, pulling and pushing, type of the expansive force or pressure (in a range of about 5-20 mm Hg, preferably, about 10 mm Hg) to the inner wall surface, to the outer wall surface, to the intermediate wall region, or, to a combination of wall regions thereof, of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

In alternative embodiments of the second principle preferred embodiment of the method and device, generally applicable to each specific case (a)-(c), the ventricular device, further includes at least one non-magnetic component or mechanism, which operatively functions together with other elements or components of the ventricular device for optimally effecting the magnetic repulsion functionality of the ventricular device, while minimally disturbing systolic function of the heart.

For example, for implementing Step (a) of operatively connecting the ventricular device in a rest condition to the left ventricle of the heart, the ventricular device, in general, including the at least one magnetic component, in particular, further includes at least one non-magnetic component or mechanism for anchoring, adhering, and/or, attaching, at least one part or region of the ventricular device, in general, and, the at least one magnetic component, in particular, to at least one part of wall region of the left ventricle where the ventricular device is configured for in-vivo magnetic repulsion operation.

The anchoring, adhering, and/or, attaching, component or mechanism is constructed from a single type of material, or, from a plurality of different types of materials, having variable geometry, shape, form, and, dimensions. More specifically, the anchoring, adhering, and/or, attaching, component or mechanism is constructed from a single type of material, or, from a plurality of different types of materials, having variable geometry, shape, form, and, dimensions, exhibiting (i) physicochemical properties and behavior selected from the group consisting of anchoring, adhering, attaching, and, combinations thereof, and, exhibiting (ii) physicochemical properties and behavior which are (1) non-interfering, additive, or, synergistic, with the magnetic repulsion functionality of the ventricular device during in-vivo operation in the heart, (2) minimally disturbing to the overall functionality of the heart during the cardiac cycle, and, (3) biocompatible.

An exemplary anchoring, adhering, and/or, attaching, component or mechanism is selected from the group consisting of biocompatible pins, biocompatible needles, biocompatible spikes, biocompatible screws, biocompatible clamps, biocompatible glue, biocompatible adhesion, surgical sutures, and, combinations thereof, having dimensions of length, height, and, width, depth, or thickness, each on the order of microns to centimeters, in the range of between about 10 microns to about 8 cm.

In alternative embodiments of the second principle preferred embodiment of the method and device, generally applicable to each specific case (a)-(c), the ventricular device further includes at least one additional separate magnetic mechanism, surrounding or encasing the left ventricle and/or the heart, and/or, located outside of the body, which operatively functions together with the ventricular device, in general, and, together with the at least one magnetic component as a single entity, or, each of the at least two separated magnetic elements or magnets as a plurality of each magnetic component, in particular, for providing a radially outward, magnetic attractive, pulling type of the expansive force or pressure to the wall region of the left ventricle, for reducing intracardiac hydrostatic pressure during ventricular diastole of the heart, thereby, improving diastolic function of the left ventricle of the heart, while minimally disturbing systolic function of the heart.

Figure 18:
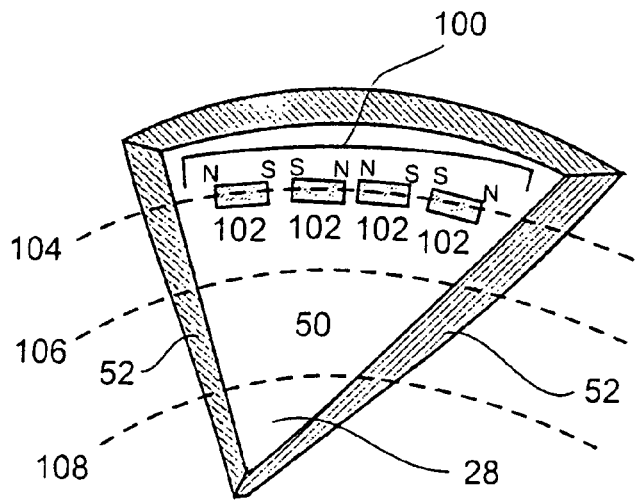
FIG. 18 is a schematic diagram illustrating a perspective view of a first general type of exemplary ventricular device for implementing specific case (a) of the second principle preferred embodiment of the method, of positioning the at least one magnetic component of the ventricular device adjacent to the inner wall surface of the left ventricle, in accordance with the present invention.
Figure 19:
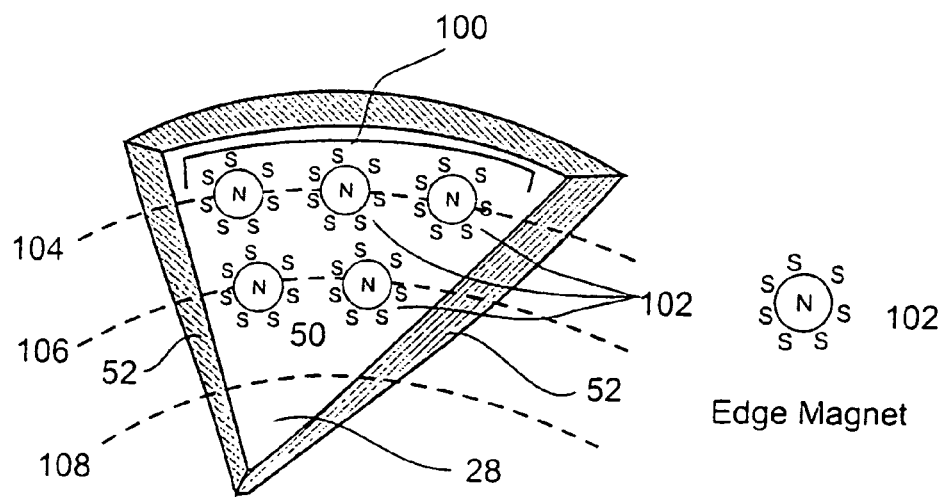
FIG. 19 is a schematic diagram illustrating a perspective view of a second general type of exemplary ventricular device for implementing specific case (a), of the second principle preferred embodiment of the method, of positioning the at least one magnetic component of the ventricular device adjacent to the inner wall surface of the left ventricle, in accordance with the present invention.
Figure 20:
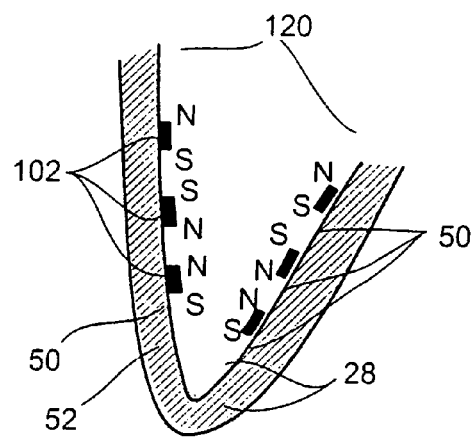
FIG. 20 is a schematic diagram illustrating a cross sectional view of an exemplary ventricular device for implementing specific case (a) of the second principle preferred embodiment of the method, of positioning the at least one magnetic component of the ventricular device adjacent to the inner wall surface of the left ventricle, in accordance with the present invention.
Figure 21:
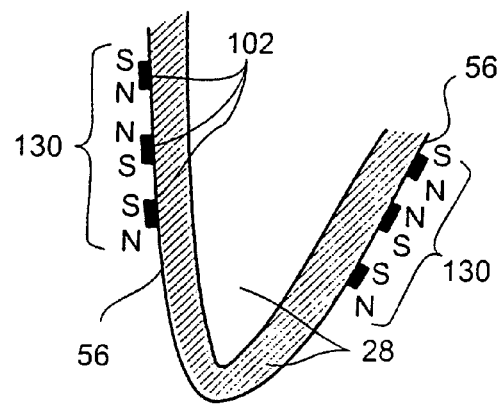
FIG. 21 is a schematic diagram illustrating a cross sectional view of a first general type of exemplary ventricular device for implementing specific case (b) of the second principle preferred embodiment of the method, of positioning the at least one magnetic component of the ventricular device adjacent to the outer wall surface of the left ventricle, in accordance with the present invention.
Figure 22:
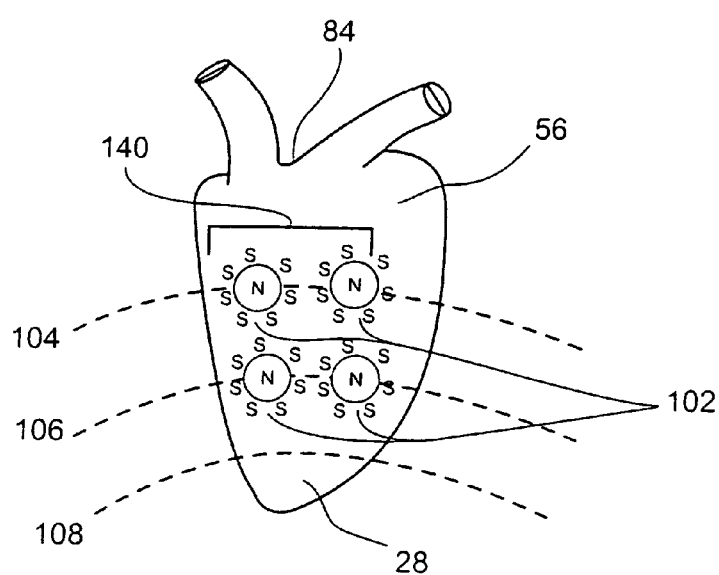
FIG. 22 is a schematic diagram illustrating a perspective view of a second general type of exemplary ventricular device for implementing specific case (b) of the second principle preferred embodiment of the method, of positioning the at least one magnetic component of the ventricular device adjacent to the outer wall surface of the left ventricle, in accordance with the present invention.
Figure 23:
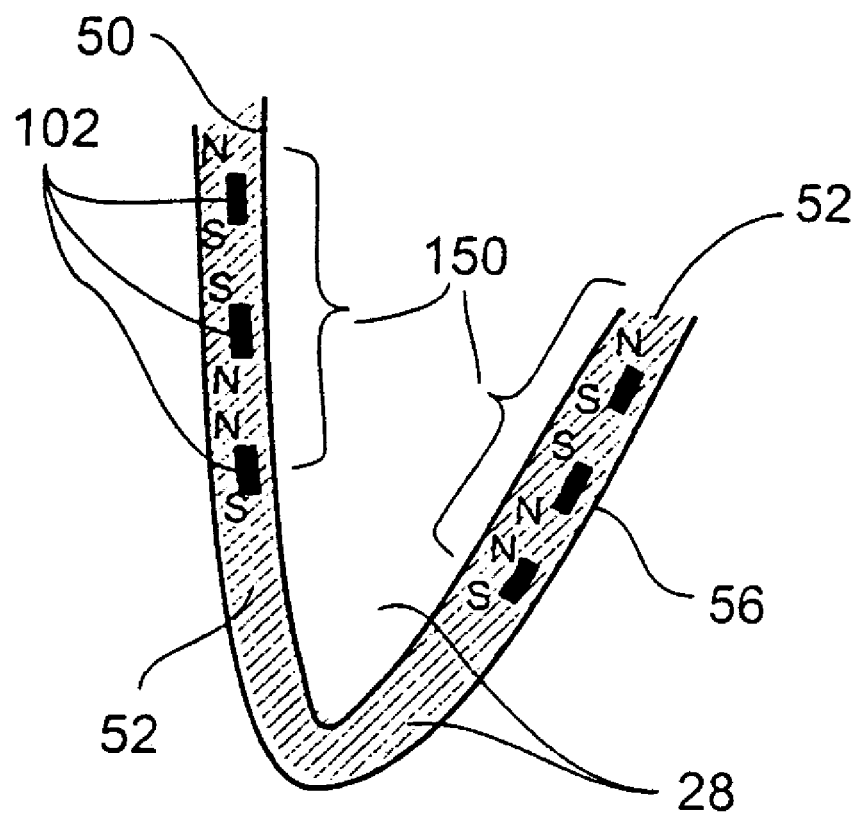
FIG. 23 is a schematic diagram illustrating a cross sectional view of a general type of exemplary ventricular device for implementing specific case (c) of the second principle preferred embodiment of the method, of positioning the at least one magnetic component of the ventricular device adjacent to the intermediate wall region of the left ventricle, in accordance with the present invention.

Following are description and accompanying drawings for describing and illustrating, respectively, various examples of alternative embodiments of the previously indicated three specific cases (a)-(c), of the second principle preferred embodiment of the method and device. FIGS. 18-20 are used for illustrating specific case (a), relating to positioning the at least one magnetic component of the ventricular device adjacent to the inner wall surface of the left ventricle. FIGS. 21-22 are used for illustrating specific case (b), relating to positioning the at least one magnetic component of the ventricular device adjacent to the outer wall surface of the left ventricle. FIG. 23 is used for illustrating specific case (c), relating to positioning the at least one magnetic component of the ventricular device adjacent to the intermediate wall region of the left ventricle. In these figures, the ventricular device, in general, including the at least one magnetic component as a single entity, or, each of the at least two separated magnetic elements or magnets as a plurality of each magnetic component, in particular, is drawn as substantially symmetric, in a non-limiting fashion, for illustrative and exemplary purposes. However, as previously indicated above, the variable geometry, shape, and, form, of the ventricular device of each specific case (a)-(c), in general, including the at least one magnetic component as a single entity, or, each of the at least two separated magnetic elements or magnets as a plurality of each magnetic component, in particular, are characterized by at least one physical aspect or descriptor selected from the group consisting of a variable extent or degree of symmetry, a variable extent or degree of asymmetry, and combinations thereof.

FIG. 18 is a schematic diagram illustrating a perspective view of a first general type of exemplary ventricular device, generally referred to as ventricular device 100, for implementing specific case (a) of the second principle preferred embodiment of the method and device, of positioning the at least one magnetic component of the ventricular device adjacent to the inner wall surface of the left ventricle. In FIG. 18, ventricular device 100 is illustrated in a 'rest' position, that is, in a position whereby ventricular device 100 potentially applies a radially outward, magnetic repulsion, pushing type of the expansive force or pressure to inner wall surface 50 of left ventricle 28.

In this first general type of exemplary embodiment, ventricular device 100 is designed, configured, and constructed, as a single multi-element magnetic component, herein, also referred to as magnetic component 100, featuring four separated rectangular or 'bar' type bipolar magnetic elements or magnets 102, each having two opposite magnetic poles of a north pole and a south pole (indicated in FIG. 18 by the letters 'N' and 'S', respectively), and same poles, that is, north poles and south poles, of magnetic elements or magnets 102 are positioned facing each other for generating the radially outward, magnetic repulsion, pushing type of the expansive force or pressure to inner wall surface 50 of left ventricle 28. Rectangular or bar magnetic elements or magnets 102 of ventricular device or magnetic component 100 are disposed in a same horizontal plane or row 104 along the curvature of inner wall surface 50 of left ventricle 28.

In alternative embodiments, ventricular device or magnetic component 100, shown in FIG. 18, features another number, such as two, three, or, more than four, of separated rectangular or bar type magnetic elements or magnets 102, disposed in a same horizontal plane or row 104, or, disposed in a combination of different horizontal planes or rows, such as different horizontal planes or rows 104, 106, and 108, and/or, disposed in a combination of different vertical planes or columns (not referenced in FIG. 18), along the curvature of inner wall surface 50 of left ventricle 28, whereby, same poles of magnetic elements or magnets 102 are positioned facing each other for generating the radially outward, magnetic repulsion, pushing type of the expansive force or pressure to inner wall surface 50 of left ventricle 28.

A second general type of an exemplary ventricular device, including the at least one magnetic component, for implementing specific case (a) of the second principle preferred embodiment of the method and device of the present invention, is described and illustrated in FIG. 19, as follows.

FIG. 19 is a schematic diagram illustrating a perspective view of a second general type of exemplary ventricular device, generally referred to as ventricular device 110, for implementing specific case (a) of the second principle preferred embodiment of the method and device, of positioning the at least one magnetic component of the ventricular device adjacent to the inner wall surface of the left ventricle. In FIG. 19, ventricular device 110 is illustrated in a 'rest' position, that is, in a position whereby ventricular device 110 potentially applies a radially outward, magnetic repulsion, pushing type of the expansive force or pressure to inner wall surface 50 of left ventricle 28.

In this second general type of exemplary embodiment, ventricular device 110 is designed, configured, and constructed, as a single multi-element magnetic component, herein, also referred to as magnetic component 110, featuring six separated disc or 'edge' type bipolar magnetic elements or magnets 102, each having two opposite magnetic poles of a north pole and a south pole (indicated in FIG. 19 by the letters 'N' and 'S', respectively), and same poles, that is, north poles and south poles, of magnetic elements or magnets 102 are positioned facing each other for generating the radially outward, magnetic repulsion, pushing type of the expansive force or pressure to inner wall surface 50 of left ventricle 28. Disc or edge magnetic elements or magnets 102 of ventricular device or magnetic component 110 are disposed in two different horizontal planes or rows 104 and 106 along the curvature of inner wall surface 50 of left ventricle 28.

In alternative embodiments, ventricular device or magnetic component 110, shown in FIG. 19, features another number, such as two, three, four, five, or, more than six, of separated disc or edge type magnetic elements or magnets 102, disposed in a same horizontal plane or row 104, or, disposed in a combination of different horizontal planes or rows 106 and 108, and/or disposed in a combination of different vertical planes or columns (not referenced in FIG. 19), along the curvature of inner wall surface 50 of left ventricle 28, whereby, same poles of magnetic elements or magnets 102 are positioned facing each other for generating the radially outward, magnetic repulsion, pushing type of the expansive force or pressure to inner wall surface 50 of left ventricle 28.

In alternative embodiments for implementing specific case (a) of the second principle preferred embodiment of the method and device, magnetic elements or magnets 102 of ventricular device or magnetic component 100 (FIG. 18), or, of ventricular device or magnetic component 110 (FIG. 19), have variable geometry, shape, form, and, dimensions, and, magnetic strengths, which, as previously indicated above, are specifically determined, in part, according to actual or measured dynamical (variable) geometry, shape, form, and, dimensions of an actual heart, in general, and, of an actual left ventricle, in particular, and, are also specifically determined, in part, according to the desired or necessary extent or degree of magnetic repulsion, for properly and optimally performing the critical function of potentially exerting a radially outward, magnetic repulsion, pushing type of the expansive force or pressure (in a range of about 5-20 mm Hg, preferably, about 10 mm Hg) to the inner wall surface of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

As previously stated above, in the general description of the second principle preferred embodiment of the method and device, applicable to each specific case (a)-(c), in alternative embodiments, the ventricular device further includes at least one non-magnetic component or mechanism which operatively functions together with the ventricular device for optimally effecting the magnetic functionality of the ventricular device, while minimally disturbing systolic function of the heart.

Accordingly, in alternative embodiments, ventricular device or magnetic component 100 (FIG. 18), or, ventricular device or magnetic component 110 (FIG. 19), in general, including magnetic elements or magnets 102, in particular, further includes at least one non-magnetic component or mechanism for anchoring, adhering, and/or, attaching, at least one part or region of ventricular device or magnetic component 100 (FIG. 18), or, at least one part or region of ventricular device or magnetic component 110 (FIG. 19), respectively, in general, such as magnetic elements or magnets 102, in particular, to at least one part of inner wall surface 50 of left ventricle 28 where ventricular device or magnetic component 100 (FIG. 18), or, where ventricular device or magnetic component 110 (FIG. 19), respectively, is configured for in-vivo magnetic operation.

Specific types, and materials of construction, geometry, shape, form, and, dimensions, of the at least one anchoring, adhering, and/or, attaching, component or mechanism are described in the general description, above, and are applicable to ventricular device or magnetic component 100 (FIG. 18), or, to ventricular device or magnetic component 110 (FIG. 19), of specific case (a). In particular, the two exemplary types, non-transmural and transmural, of anchoring, adhering, and/or, attaching, mechanisms applicable to ventricular device or elastic component 10 of specific case (a) of the first principle preferred embodiment of the method and device, previously described and illustrated in FIGS. 10A and 10B, respectively, are also applicable to ventricular device or magnetic component 100 (FIG. 18), or, to ventricular device or magnetic component 110 (FIG. 19), of the second principle preferred embodiment of the method and device.

Each magnetic element or magnet 102 of ventricular device or magnetic component 100 (FIG. 18) has a rectangular or bar type of geometry, shape, and, form, and is configured to compactly fit into left ventricle 28. Similarly, each magnetic element or magnet 102 of ventricular device or magnetic component 110 (FIG. 19) has a disc or edge type of geometry, shape, and, form, and is configured to compactly fit into left ventricle 28. For specific case (a) of the method and device, where the ventricular device, for example, ventricular device or magnetic component 100 (FIG. 18), or, ventricular device or magnetic component 110, is connected to at least one part of the inner wall surface of the left ventricle, following inserting and maneuvering of the ventricular device inside the cardiac lumen of the heart, the ventricular device is connected to the inner wall surface of the left ventricle. Connecting, by way of anchoring, adhering, and/or, attaching, the ventricular device, including the at least one magnetic component as a single entity, or, each of the at least two separated magnetic elements or magnets as a plurality of each magnetic component, is performed by using at least one anchoring, adhering, and/or, attaching, component or mechanism, included as part of the ventricular device, as previously described above, and/or, separate from the ventricular device.

Ventricular device 100, or, ventricular device 110, is inserted into place by using a minimally invasive surgical procedure, such as catheterization, thoracoscopy, or, thoracotomy, with a relatively small diameter delivery system (not shown) for delivering and deploying ventricular device 100, or, ventricular device 110, respectively, into the body, in general, and to left ventricular cardiac inner wall surface 50, in particular. Alternatively, ventricular device 100, or, ventricular device 110, is inserted into place by using trans-apical deployment, or, by using percutaneous transluminal catheterization deployment, according to the procedures previously described above with respect to insertion and deployment of ventricular device or elastic component 10 of specific case (a) of the first principle preferred embodiment of the method and device. Alternatively, ventricular device 100, or, ventricular device 110, may be inserted and positioned through the left atrium and the mitral valve of the heart under direct visualization, as part of an open-heart procedure. In this case, the technique for fixing ventricular device 100, or, ventricular device 110, after proper positioning in left ventricle 28 is similar to that used during trans-apical deployment.

Another of the many possible alternative embodiments of the first general type of exemplary ventricular device 100 (FIG. 18) is illustrated in FIG. 20, a schematic diagram illustrating a cross sectional view of an exemplary ventricular device 120 for implementing specific case (a) of the second principle preferred embodiment of the method and device, of positioning the at least one magnetic component of the ventricular device adjacent to the inner wall surface of the left ventricle. In FIG. 20, ventricular device 120 is illustrated in a 'rest' position, that is, in a position whereby ventricular device 120 potentially applies a radially outward, magnetic repulsion, pushing type of the expansive force or pressure to inner wall surface 50 of left ventricle 28. In this exemplary embodiment, ventricular device 120 is designed, configured, and constructed, as a multi-element magnetic component, herein, also referred to as magnetic component 120, featuring a plurality of at least six separated rectangular or bar type magnetic elements or magnets 102, each having two opposite magnetic poles of a north pole and a south pole (indicated in FIG. 20 by the letters 'N' and 'S', respectively), and same poles, that is, north poles and south poles, of magnetic elements or magnets 102 are positioned facing each other for generating the radially outward, magnetic repulsion, pushing type of the expansive force or pressure to inner wall surface 50 of left ventricle 28.

FIG. 21 is a schematic diagram illustrating a cross sectional view of a first general type of exemplary ventricular device, generally referred to as ventricular device 130, for implementing specific case (b) of the second principle preferred embodiment of the method and device, of positioning the at least one magnetic component of the ventricular device adjacent to the outer wall surface of the left ventricle. In FIG. 21, ventricular device 130 is illustrated in a 'rest' position, that is, in a position whereby ventricular device 130 potentially applies a radially outward, magnetic repulsion, pulling type of the expansive force or pressure to outer wall surface 56 of left ventricle 28. In this exemplary embodiment, ventricular device 130 is designed, configured, and constructed, as a multi-element magnetic component, herein, also referred to as magnetic component 130, featuring a plurality of at least six separated rectangular or bar type magnetic elements or magnets 102, each having two opposite magnetic poles of a north pole and a south pole (indicated in FIG. 21 by the letters 'N' and 'S', respectively), and same poles, that is, north poles and south poles, of magnetic elements or magnets 102 are positioned facing each other for generating the radially outward, magnetic repulsion, pulling type of the expansive force or pressure to outer wall surface 56 of left ventricle 28.

A second general type of an exemplary ventricular device, including the at least one magnetic component, for implementing specific case (b) of the second principle preferred embodiment of the method and device of the present invention, is described and illustrated in FIG. 22, as follows.

FIG. 22 is a schematic diagram illustrating a perspective view of a second general type of exemplary ventricular device, generally referred to as ventricular device 140, for implementing specific case (b) of the second principle preferred embodiment of the method and device, of positioning the at least one magnetic component of the ventricular device adjacent to the outer wall surface of the left ventricle. In FIG. 22, ventricular device 140 is illustrated in a 'rest' position, that is, in a position whereby ventricular device 140 potentially applies a radially outward, magnetic repulsion, pulling type of the expansive force or pressure to outer wall surface 56 of left ventricle 28.

In this second general type of exemplary embodiment, ventricular device 140 is designed, configured, and constructed, as a single multi-element magnetic component, herein, also referred to as magnetic component 140, featuring four separated disc or edge type magnetic elements or magnets 102, each having two opposite magnetic poles of a north pole and a south pole (indicated in FIG. 22 by the letters 'N' and 'S', respectively), and same poles, that is, north poles and south poles, of magnetic elements or magnets 102 are positioned facing each other for generating the radially outward, magnetic repulsion, pulling type of the expansive force or pressure to outer wall surface 56 of left ventricle 28. Disc or edge magnetic elements or magnets 102 of ventricular device or magnetic component 140 are disposed in two different horizontal planes or rows 104 and 106 along the curvature of outer wall surface 56 of left ventricle 28.

In alternative embodiments, ventricular device or magnetic component 140, shown in FIG. 22, features another number, such as two, three, or, more than four, of separated disc or edge type magnetic elements or magnets 102, disposed in a same horizontal plane or row 104, or, disposed in a combination of different horizontal planes or rows 106 and 108, and/or disposed in a combination of different vertical planes or columns (not referenced in FIG. 22), along the curvature of outer wall surface 56 of left ventricle 28, whereby, same poles of magnetic elements or magnets 102 are positioned facing each other for generating the radially outward, magnetic repulsion, pulling type of the expansive force or pressure to outer wall surface 56 of left ventricle 28.

In alternative embodiments for implementing specific case (b) of the second principle preferred embodiment of the method and device, magnetic elements or magnets 102 of ventricular device or magnetic component 130 (FIG. 21), or, of ventricular device or magnetic component 140 (FIG. 22), have variable geometry, shape, form, and, dimensions, and, magnetic strengths, which, as previously indicated above, are specifically determined, in part, according to actual or measured dynamical (variable) geometry, shape, form, and, dimensions of an actual heart, in general, and, of an actual left ventricle, in particular, and, are also specifically determined, in part, according to the desired or necessary extent or degree of magnetic repulsion, for properly and optimally performing the critical function of potentially exerting a radially outward, magnetic repulsion, pulling type of the expansive force or pressure (in a range of about 5-20 mm Hg, preferably, about 10 mm Hg) to the outer wall surface of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

As previously stated above, in the general description of the second principle preferred embodiment of the method and device, applicable to each specific case (a)-(c), in alternative embodiments, the ventricular device further includes at least one non-magnetic component or mechanism which operatively functions together with the ventricular device for optimally effecting the magnetic functionality of the ventricular device, while minimally disturbing systolic function of the heart.

Accordingly, in alternative embodiments, ventricular device or magnetic component 130 (FIG. 21), or, ventricular device or magnetic component 140 (FIG. 22), in general, including magnetic elements or magnets 102, in particular, further includes at least one non-magnetic component or mechanism for anchoring, adhering, and/or, attaching, at least one part or region of ventricular device or magnetic component 130 (FIG. 21), or, at least one part or region of ventricular device or magnetic component 140 (FIG. 22), respectively, in general, such as magnetic elements or magnets 102, in particular, to at least one part of outer wall surface 56 of left ventricle 28 where ventricular device or magnetic component 130 (FIG. 21), or, where ventricular device or magnetic component 140 (FIG. 22), respectively, is configured for in-vivo magnetic operation.

Specific types, and materials of construction, geometry, shape, form, and, dimensions, of the at least one anchoring, adhering, and/or, attaching, component or mechanism are described in the general description, above, and are applicable to ventricular device or magnetic component 130 (FIG. 21), or, to ventricular device or magnetic component 140 (FIG. 22), of specific case (b). In particular, the two exemplary types, non-transmural and transmural, of anchoring, adhering, and/or, attaching, mechanisms applicable to ventricular device or elastic component 10 of specific case (a) of the first principle preferred embodiment of the method and device, previously described and illustrated in FIGS. 10A and 10B, respectively, are also applicable to ventricular device or magnetic component 130 (FIG. 21), or, to ventricular device or magnetic component 140 (FIG. 22), of the second principle preferred embodiment of the method and device.

For specific case (b) of the method and device, where the ventricular device, for example, ventricular device or magnetic component 130, or, 140, is connected to at least one part of the outer wall surface of the left ventricle, following inserting and maneuvering of the ventricular device inside the thoracic cavity, the ventricular device is connected to the outer wall surface of the left ventricle. Connecting, by way of anchoring, adhering, and/or, attaching, the ventricular device, including the at least one magnetic component as a single entity, or, each of the at least two separated magnetic elements or magnets as a plurality of each magnetic component, is performed by using at least one anchoring, adhering, and/or, attaching, component or mechanism, included as part of the ventricular device, as previously described above, and/or, separate from the ventricular device.

For specific case (b) of the method and device, ventricular device 130, or, 140, is inserted into place by using a minimally invasive surgical procedure, such as thoracoscopy, according to the procedure previously described and illustrated in FIG. 15, above, with respect to insertion and deployment of ventricular device or elastic component 70, 80, or, 82, of specific case (b) of the first principle preferred embodiment of the method and device, or, thoracotomy, with a relatively small diameter delivery system for delivering and deploying the ventricular device into the body, in general, and to a left ventricular cardiac outer wall surface, in particular.

FIG. 23 is a schematic diagram illustrating a cross sectional view of a general type of exemplary ventricular device, generally referred to as ventricular device 150, for implementing specific case (c) of the second principle preferred embodiment of the method and device, of positioning the at least one magnetic component of the ventricular device adjacent to the intermediate wall region of the left ventricle. In FIG. 23, ventricular device 150 is illustrated in a 'rest' position, that is, in a position whereby ventricular device 150 potentially applies a radially outward, magnetic repulsion, pulling and pushing type of the expansive force or pressure to intermediate wall region 52 of left ventricle 28. In this exemplary embodiment, ventricular device 150 is designed, configured, and constructed, as a multi-element magnetic component, herein, also referred to as magnetic component 150, featuring a plurality of at least six separated rectangular or bar type magnetic elements or magnets 102, each having two opposite magnetic poles of a north pole and a south pole (indicated in FIG. 23 by the letters 'N' and 'S', respectively), and same poles, that is, north poles and south poles, of magnetic elements or magnets 102 are positioned facing each other for generating the radially outward, magnetic repulsion, pulling and pushing type of the expansive force or pressure to intermediate wall region 52 of left ventricle 28. Many alternative specific embodiments of exemplary ventricular device or magnetic component 150 are clearly possible for implementing specific case (c) of the second principle preferred embodiment of the method and device.

In alternative embodiments for implementing specific case (c) of the second principle preferred embodiment of the method and device, magnetic elements or magnets 102 of ventricular device or magnetic component 150 (FIG. 23) have variable geometry, shape, form, and dimensions, and, magnetic strengths, which, as previously indicated above, are specifically determined, in part, according to actual or measured dynamical (variable) geometry, shape, form, and, dimensions of an actual heart, in general, and, of an actual left ventricle, in particular, and, are also specifically determined, in part, according to the desired or necessary extent or degree of magnetic repulsion, for properly and optimally performing the critical function of potentially exerting a radially outward, magnetic repulsion, pulling and pushing type of the expansive force or pressure (in a range of about 5-20 mm Hg, preferably, about 10 mm Hg) to the intermediate wall region of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

As previously stated above, in the general description of the second principle preferred embodiment of the method and device, applicable to each specific case (a)-(c), in alternative embodiments, the ventricular device further includes at least one non-magnetic component or mechanism which operatively functions together with the ventricular device for optimally effecting the magnetic functionality of the ventricular device, while minimally disturbing systolic function of the heart.

Accordingly, in alternative embodiments, ventricular device or magnetic component 150 (FIG. 23), in general, including magnetic elements or magnets 102, in particular, further includes at least one non-magnetic component or mechanism for anchoring, adhering, and/or, attaching, at least one part or region of ventricular device or magnetic component 150, in general, such as magnetic elements or magnets 102, in particular, to at least one part of intermediate wall region 52 of left ventricle 28 where ventricular device or magnetic component 150 is configured for in-vivo magnetic operation.

Specific types, and materials of construction, geometry, shape, form, and, dimensions, of the at least one anchoring, adhering, and/or, attaching, component or mechanism are described in the general description, above, and are applicable to ventricular device or magnetic component 150 of specific case (c). In particular, the two exemplary types, non-transmural and transmural, of anchoring, adhering, and/or, attaching, mechanisms applicable to ventricular device or elastic component 10 of specific case (a) of the first principle preferred embodiment of the method and device, previously described and illustrated in FIGS. 10A and 10B, respectively, are also applicable to ventricular device or magnetic component 150 of the second principle preferred embodiment of the method and device. Connecting, by way of anchoring, adhering, and/or, attaching, the ventricular device, including the at least one magnetic component as a single entity, or, each of the at least two separated magnetic elements or magnets as a plurality of each magnetic component, is performed by using at least one anchoring, adhering, and/or, attaching, component or mechanism, included as part of the ventricular device, as previously described above, and/or, separate from the ventricular device.

For specific case (c), of the second principle preferred embodiment of the method and device, the ventricular device is inserted into place by using a minimally invasive surgical procedure, such as catheterization, thoracoscopy, or, thoracotomy, with a relatively small diameter delivery system for delivering and deploying the ventricular device into the body, in general, and, to a left ventricular cardiac intermediate wall region, in particular.

As previously stated above, in the general description of the second principle preferred embodiment of the method and device, applicable to each specific case (a)-(c), in alternative embodiments, the ventricular device further includes at least one additional separate magnetic mechanism, surrounding or encasing the left ventricle and/or the heart, and/or, located outside of the body, which operatively functions together with the ventricular device, in general, and, together with the at least one magnetic component as a single entity, or, each of the at least two separated magnetic elements or magnets as a plurality of each magnetic component, in particular, for providing a radially outward, magnetic attractive, pulling type of the expansive force or pressure to the wall region of the left ventricle, for reducing intracardiac hydrostatic pressure during ventricular diastole of the heart, thereby, improving diastolic function of the left ventricle of the heart, while minimally disturbing systolic function of the heart.

Accordingly, in alternative embodiments, ventricular device or magnetic component 100 (FIG. 18), 102 (FIG. 19), or, 120 (FIG. 20), of specific case (a); ventricular device or magnetic component 130 (FIG. 21), or, 140 (FIG. 22), of specific case (b); or, ventricular device or magnetic component 150 (FIG. 23) of specific case (c), further includes at least one additional separate magnetic mechanism (not shown), surrounding or encasing left ventricle 28 and/or the heart, and/or, located outside of the body, which operatively functions together with the respective ventricular device, in general, and, together with the at least one magnetic component as a single entity, or, each of the at least two separated magnetic elements or magnets 102 as a plurality of each magnetic component, in particular, for providing a radially outward, magnetic attractive, pulling type of the expansive force or pressure to the wall region of the left ventricle, for reducing intracardiac hydrostatic pressure during ventricular diastole of the heart, thereby, improving diastolic function of the left ventricle of the heart, while minimally disturbing systolic function of the heart.

The third principle preferred embodiment of the method and device of the present invention is either an 'additive' combination, or, an 'integrated' combination, of the first and second principle preferred embodiments of the method and device of the present invention, previously described and illustrated, in detail, above. Herein, the additive combination, and, the integrated combination, are referred to as specific case (a), and, specific case (b), respectively, of the third principle preferred embodiment of the method, and device of the present invention.

Above general and particular descriptions and illustrations of the four specific cases (a)-(d) of the first principle preferred embodiment of the method and device, and alternative embodiments thereof, based on utilizing the physicochemical property and behavior of elasticity or resiliency, and, of the three specific cases (a)-(c) of the second principle preferred embodiment of the method and device, and alternative embodiments thereof, based on utilizing the physicochemical property and behavior of magnetic repulsion, are therefore, fully applicable herein for implementing specific case (a) and specific case (b) of the third principle preferred embodiment of the method and device of the present invention.

Accordingly, for implementing specific case (a) of the third preferred principle embodiment of the method and device, in Step (a), there is (i) operatively connecting the ventricular device, in general, including the at least one elastic component, in particular, of any of the specific cases (a)-(d) of the first principle preferred embodiment of the method and device, previously described above and illustrated in FIGS. 2A-17, herein, referred to as the elastic ventricular device, in a rest condition to the left ventricle of the heart, whereby, the at least one elastic component of the elastic ventricular device is positioned adjacent to at least one part of wall region of the left ventricle, and potentially exerts a radially outward, elastic, pushing, pulling, or, pulling and pushing, type of the expansive force or pressure to the wall region of the left ventricle, and, (ii) operatively connecting the ventricular device, in general, including the at least one magnetic component, in particular, of any of the specific cases (a)-(c) of the second principle preferred embodiment of the method and device, previously described above and illustrated in FIGS. 18-23, herein, referred to as the magnetic ventricular device, in a rest condition to the left ventricle of the heart, whereby, the at least one magnetic component of the magnetic ventricular device is positioned adjacent to at least one part of wall region of the left ventricle, and potentially exerts a radially outward, magnetic repulsion, pushing, pulling, or, pulling and pushing, type of the expansive force or pressure to the wall region of the left ventricle, for reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

Thus, in effect, implementing specific case (a) of the third preferred principle embodiment of the method and device, in Step (a), corresponds to 'additively' combining the elastic ventricular device of the first principle preferred embodiment of the method and device, with the magnetic ventricular device of the second principle preferred embodiment of the method and device, for effectively connecting an elastic ventricular device in a rest condition, and, connecting a magnetic ventricular device in a rest condition, to the left ventricle of the heart. For specific case (a), the at least one elastic component of the elastic ventricular device is structurally separate from the at least one magnetic component of the magnetic ventricular device, whereby the 'additive' device functions as an additive combination of the at least one elastic component and of the at least one magnetic component for exerting the radially outward expansive force or pressure to the at least one part of wall region of the left ventricle during ventricular diastole.

Accordingly, for implementing specific case (b) of the third preferred principle embodiment of the method and device, in Step (a), there is operatively connecting the ventricular device, in general, including (i) the at least one elastic component, in particular, of any of the specific cases (a)-(d) of the first principle preferred embodiment of the method and device, previously described above and illustrated in FIGS. 2A-17, and, including (ii) the at least one magnetic component, in particular, of any of the specific cases (a)-(c) of the second principle preferred embodiment of the method and device, previously described above and illustrated in FIGS. 18-23, herein, referred to as the elasto-magnetic ventricular device, in a rest condition to the left ventricle of the heart, whereby, (i) the at least one elastic component of the elasto-magnetic ventricular device is positioned adjacent to at least one part of wall region of the left ventricle, and potentially exerts a radially outward, elastic, pushing, pulling, or, pulling and pushing, type of the expansive force or pressure to the wall region of the left ventricle, and, whereby (ii) the at least one magnetic component of the elasto-magnetic ventricular device is positioned adjacent to at least one part of wall region of the left ventricle, and potentially exerts a radially outward, magnetic repulsion, pushing, pulling, or, pulling and pushing, type of the expansive force or pressure to the wall region of the left ventricle, for reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

Thus, in effect, implementing specific case (b) of the third preferred principle embodiment of the method and device, in Step (a), corresponds to 'integratively' combining the elastic ventricular device of the first principle preferred embodiment of the method and device, with the magnetic ventricular device of the second principle preferred embodiment of the method and device, for effectively connecting a single integrated elasto-magnetic ventricular device in a rest condition to the left ventricle of the heart. For specific case (b), the at least one elastic component of the elastic ventricular device is structurally integrated with the at least one magnetic component of the magnetic ventricular device, whereby the 'integrated' device functions as an integrative combination of the at least one elastic component and of the at least one magnetic component for exerting the radially outward expansive force or pressure to the at least one part of wall region of the left ventricle during ventricular diastole.

In Step (b) of the method of the present invention, there is allowing the heart to undergo ventricular systole, during which the potential radially outward expansive force or pressure of the device dynamically increases to a pre-determined magnitude.

Step (b) is generally applicable to each of the above general and particular descriptions and illustrations of (1) the four specific cases (a)-(d) of the first principle preferred embodiment of the method and device, and alternative embodiments thereof, based on utilizing the physicochemical property and behavior of elasticity or resiliency, (2) the three specific cases (a)-(c) of the second principle preferred embodiment of the method and device, and alternative embodiments thereof, based on utilizing the physicochemical property and behavior of magnetic repulsion, and, (3) the two specific cases (a)-(b) of the third principle preferred embodiment of the method and device, and alternative embodiments thereof, based on utilizing the physicochemical properties and behaviors of both elasticity or resiliency and magnetic repulsion.

Accordingly, with respective reference to each of the above described and illustrated first, second, or, third, principle preferred embodiment of the method and device, in Step (b), during the ventricular systolic (contraction) stage of the cardiac cycle, the potential radially outward respective elastic, magnetic repulsion, or, elastic and magnetic repulsion, type of the expansive force or pressure to the wall region of the left ventricle, associated with the at least one respective elastic, magnetic, or, elastic and magnetic, component of the respective elastic, magnetic, or, elasto-magnetic, ventricular device, dynamically increases to a pre-determined magnitude.

The pre-determined magnitude of the potential radially outward respective elastic, magnetic repulsion, or, elastic and magnetic repulsion, type of the expansive force or pressure is primarily determined according to (i) the particular type, and, respective elastic, magnetic, or, elastic and magnetic repulsion, properties and behavior, of the material used for constructing the at least one respective elastic, magnetic, or, elastic and magnetic, component of the respective elastic, magnetic, or, elasto-magnetic, ventricular device, (ii) the particular configuration and positioning of the at least one respective elastic, magnetic, or, elastic and magnetic, component of the respective elastic, magnetic, or, elasto-magnetic, ventricular device, adjacent to the wall region of the left ventricle, and, (iii) the desired or necessary extent or degree of the respective elasticity, magnetic repulsion, or, elasticity and magnetic repulsion, for properly and optimally performing the critical function of potentially exerting the radially outward, respective elastic, magnetic repulsion, or, elastic and magnetic repulsion, pushing, pulling, or, pulling and pushing, type of the expansive force or pressure (in a range of about 5-20 mm Hg, preferably, about 10 mm Hg) to the inner wall surface, to the outer wall surface, to the intermediate wall region, or, to a combination of wall regions thereof, of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

In Step (c), of the method of the present invention, there is allowing the heart to undergo ventricular diastole, during which the pre-determined magnitude of the potential radially outward expansive force of the device is dynamically converted into a corresponding kinetic radially outward expansive force or pressure applied to the wall region of the left ventricle, for reducing intracardiac hydrostatic pressure during the ventricular diastole, thereby, improving the diastolic function of the left ventricle of the heart.

Step (c) is generally applicable to each of the above general and particular descriptions and illustrations of (1) the four specific cases (a)-(d) of the first principle preferred embodiment of the method and device, and alternative embodiments thereof, based on utilizing the physicochemical property and behavior of elasticity or resiliency, (2) the three specific cases (a)-(c) of the second principle preferred embodiment of the method and device, and alternative embodiments thereof, based on utilizing the physicochemical property and behavior of magnetic repulsion, and, (3) the two specific cases (a)-(b) of the third principle preferred embodiment of the method and device, and alternative embodiments thereof, based on utilizing the physicochemical properties and behaviors of both elasticity or resiliency and magnetic repulsion.

Accordingly, with respective reference to each of the above described and illustrated first, second, or, third, principle preferred embodiment of the method and device, in Step (c), during the ventricular diastolic (expansion, distention) stage of the cardiac cycle, the pre-determined magnitude of the potential radially outward respective elastic, magnetic repulsion, or, elastic and magnetic repulsion, type of the expansive force or pressure (in a range of about 5-20 mm Hg, preferably, about 10 mm Hg) to the wall region of the left ventricle, associated with the at least one respective elastic, magnetic, or, elastic and magnetic, component of the respective elastic, magnetic, or, elasto-magnetic, ventricular device, is dynamically converted into a corresponding kinetic radially outward respective elastic, magnetic repulsion, or, elastic and magnetic repulsion, type of the expansive force or pressure (in a range of about 5-20 mm Hg, preferably, about 10 mm Hg) applied to the wall region of the left ventricle, for reducing intracardiac hydrostatic pressure during the ventricular diastole, thereby, improving the diastolic function of the left ventricle of the heart. This includes sufficiently reducing left ventricular end diastolic pressure (LVEDP), preferably, down to the normal range of about 6-12 mm Hg, during ventricular diastole of the heart.

A first 'illustrative' example of implementing Steps (a)-(c) of the present invention, is provided herein with reference to specific case (a) of the first principle preferred embodiment of the method and device, as previously described above and illustrated in FIG. 3B. Following completion of Step (a) of operatively connecting exemplary 'U' shaped elastic ventricular device 26 in a rest condition to left ventricle 28, where elastic ventricular device 26 features a plurality of two elastic arms or extensions 12 positioned adjacent to inner wall surface 50 of left ventricle 28, and is configured for in-vivo elastic operation, there is Step (b) of allowing the heart, including left ventricle 28, to undergo ventricular systole, during which the potential radially outward, elastic pushing type of the expansive force or pressure to inner wall surface 50 of left ventricle 28 by elastic ventricular device 26 dynamically increases to a pre-determined magnitude. Then, in Step (c), there is allowing the heart, including left ventricle 28, to undergo ventricular diastole, during which the pre-determined magnitude of the potential radially outward, elastic pushing type of the expansive force or pressure to inner wall surface 50 of left ventricle 28, associated with elastic arms or extensions 12 of elastic ventricular device 26, is dynamically converted into a corresponding kinetic radially outward, elastic pushing type of expansive force or pressure applied to inner wall surface 50 of left ventricle 28, for reducing intracardiac hydrostatic pressure during the ventricular diastole, thereby, improving the diastolic function of left ventricle 28 of the heart.

A second 'illustrative' example of implementing Steps (a)-(c) of the present invention, is provided herein with reference to specific case (a) of the first principle preferred embodiment of the method and device, as previously described above and illustrated in FIG. 10A. Following completion of Step (a) of operatively connecting at least one part or region 46 of exemplary elastic ventricular device 48, in general, such as elastic arms or extensions 12 and/or optional elastic lower basal section or ring formation 14, in particular, in a rest position, to at least one part of inner wall surface 50 of left ventricle 28 where exemplary ventricular device 48 is configured for in-vivo elastic operation, there is Step (b) of allowing the heart, including left ventricle 28, to undergo ventricular systole, during which the potential radially outward, elastic pushing type of the expansive force or pressure to inner wall surface 50 of left ventricle 28 by elastic ventricular device 48 dynamically increases to a pre-determined magnitude. Then, in Step (c), there is allowing the heart, including left ventricle 28, to undergo ventricular diastole, during which the pre-determined magnitude of the potential radially outward, elastic pushing type of the expansive force or pressure to inner wall surface 50 of left ventricle 28, associated with elastic arms or extensions 12 of elastic ventricular device 48, is dynamically converted into a corresponding kinetic radially outward, elastic pushing type of expansive force or pressure applied to inner wall surface 50 of left ventricle 28, for reducing intracardiac hydrostatic pressure during the ventricular diastole, thereby, improving the diastolic function of left ventricle 28 of the heart.

A third 'illustrative' example of implementing Steps (a)-(c) of the present invention, is provided herein with reference to specific case (b) of the first principle preferred embodiment of the method and device, as previously described above and illustrated in FIG. 14. Following completion of Step (a) of operatively connecting cylindrically shaped elastic ventricular device 70 in a rest condition to left ventricle 28, where elastic ventricular device 70 is positioned adjacent to and along outer wall surface 56 of left ventricle 28, and is configured for in-vivo elastic operation, there is Step (b) of allowing heart 84, including left ventricle 28, to undergo ventricular systole, during which the potential radially outward, elastic pulling type of the expansive force or pressure to outer wall surface 56 of left ventricle 28 by elastic ventricular device 70 dynamically increases to a pre-determined magnitude. Then, in Step (c), there is allowing the heart 84, including left ventricle 28, to undergo ventricular diastole, during which the pre-determined magnitude of the potential radially outward, elastic pulling type of the expansive force or pressure to outer wall surface 56 of left ventricle 28, associated with elastic ventricular device 70, is dynamically converted into a corresponding kinetic radially outward, elastic pulling type of expansive force or pressure applied to outer wall surface 56 of left ventricle 28, for reducing intracardiac hydrostatic pressure during the ventricular diastole, thereby, improving the diastolic function of left ventricle 28 of heart 84.

A fourth 'illustrative' example of implementing Steps (a)-(c) of the present invention, is provided herein with reference to specific case (c) of the first principle preferred embodiment of the method and device, as previously described above and illustrated in FIG. 16. Following completion of Step (a) of operatively connecting exemplary 'U' shaped elastic ventricular device 26 in a rest condition to left ventricle 28, where elastic ventricular device 26 features a plurality of two elastic arms or extensions 12 positioned adjacent to intermediate wall region 52 of left ventricle 28, and is configured for in-vivo elastic operation, there is Step (b) of allowing the heart, including left ventricle 28, to undergo ventricular systole, during which the potential radially outward, elastic pulling and pushing type of the expansive force or pressure to intermediate wall region 52 of left ventricle 28 by elastic ventricular device 26 dynamically increases to a pre-determined magnitude. Then, in Step (c), there is allowing the heart, including left ventricle 28, to undergo ventricular diastole, during which the pre-determined magnitude of the potential radially outward, elastic pulling and pushing type of the expansive force or pressure to intermediate wall region 52 of left ventricle 28, associated with elastic arms or extensions 12 of elastic ventricular device 26, is dynamically converted into a corresponding kinetic radially outward, elastic pulling and pushing type of expansive force or pressure applied to intermediate wall region 52 of left ventricle 28, for reducing intracardiac hydrostatic pressure during the ventricular diastole, thereby, improving the diastolic function of left ventricle 28 of the heart.

A fifth 'illustrative' example of implementing Steps (a)-(c) of the present invention, is provided herein with reference to specific case (a) of the second principle preferred embodiment of the method and device, as previously described above and illustrated in FIG. 19. Following completion of Step (a) of operatively connecting exemplary magnetic ventricular device 110 in a rest condition to left ventricle 28, where magnetic ventricular device 110 features a plurality of six separated disc or edge type magnetic elements or magnets 102 positioned adjacent to inner wall surface 50 of left ventricle 28, and is configured for in-vivo magnetic operation, there is Step (b) of allowing the heart, including left ventricle 28, to undergo ventricular systole, during which the potential radially outward, magnetic repulsion pushing type of the expansive force or pressure to inner wall surface 50 of left ventricle 28 by magnetic ventricular device 110 dynamically increases to a pre-determined magnitude. Then, in Step (c), there is allowing the heart, including left ventricle 28, to undergo ventricular diastole, during which the pre-determined magnitude of the potential radially outward, magnetic repulsion pushing type of the expansive force or pressure to inner wall surface 50 of left ventricle 28, associated with disc or edge type magnetic elements or magnets 102 of magnetic ventricular device 110, is dynamically converted into a corresponding kinetic radially outward, magnetic pushing type of expansive force or pressure applied to inner wall surface 50 of left ventricle 28, for reducing intracardiac hydrostatic pressure during the ventricular diastole, thereby, improving the diastolic function of left ventricle 28 of the heart.

A sixth 'illustrative' example of implementing Steps (a)-(c) of the present invention, is provided herein with reference to specific case (b) of the second principle preferred embodiment of the method and device, as previously described above and illustrated in FIG. 22. Following completion of Step (a) of operatively connecting exemplary magnetic ventricular device 140 in a rest condition to left ventricle 28, where magnetic ventricular device 140 features a plurality of four separated disc or edge type magnetic elements or magnets 102 positioned adjacent to outer wall surface 56 of left ventricle 28, and is configured for in-vivo magnetic operation, there is Step (b) of allowing heart 84, including left ventricle 28, to undergo ventricular systole, during which the potential radially outward, magnetic repulsion pulling type of the expansive force or pressure to outer wall surface 56 of left ventricle 28 by magnetic ventricular device 140 dynamically increases to a predetermined magnitude. Then, in Step (c), there is allowing heart 84, including left ventricle 28, to undergo ventricular diastole, during which the pre-determined magnitude of the potential radially outward, magnetic repulsion pulling type of the expansive force or pressure to outer wall surface 56 of left ventricle 28, associated with disc or edge type magnetic elements or magnets 102 of magnetic ventricular device 140, is dynamically converted into a corresponding kinetic radially outward, magnetic pulling type of expansive force or pressure applied to outer wall surface 56 of left ventricle 28, for reducing intracardiac hydrostatic pressure during the ventricular diastole, thereby, improving the diastolic function of left ventricle 28 of the heart.

In alternative embodiments of the method and device of the present invention, there is including and appropriately integrating a procedure for controllably reducing or attenuating the radially outward expansive force or pressure to the wall region of the left ventricle by the magnetic ventricular device, during the systolic stage of the cardiac cycle. In particular, a selected number of the magnetic elements or magnets 102 of the magnetic ventricular device, of the second principle preferred embodiment of the method and device, and alternative embodiments thereof, as previously described and illustrated above, may be surrounded by an insulating layer, above which is attached an electrical conducting wire. During ventricular systole, an electrical current is passed through the electrical conducting wire. The magnitude and direction of the electrical current are such that when activated, the generated electromagnetic field will cancel out the magnetic dipole produced by the magnetic elements or magnets 102 surrounded by the insulating layer. An example of this procedure is the magnetic ventricular device featuring an even number of magnetic elements or magnets 102, each of which is repulsed by its neighboring magnetic elements or magnets 102. An insulating layer and an electrical conductive wire surround each second magnetic element or magnet 102. At the beginning of ventricular systole, a current is delivered through the electrical conducting wires, canceling out the magnetic dipoles. Thus, during ventricular systole, each magnetic element or magnet 102 attracts the closest non-surrounded magnetic elements or magnets 102 and assists the systolic function of the left ventricle of the heart.

In alternative embodiments of the method and device of the present invention, in addition to the ventricular device applying a radially outward expansive force or pressure to the wall region of the left ventricle for reducing intraluminal hydrostatic pressure of the left ventricle during the ventricular diastolic stage of the cardiac cycle, thereby, improving diastolic function of the left ventricle of the heart, the ventricular device can be designed, configured, constructed, and implemented, for applying a radially inward contractive force or pressure to the wall region of the left ventricle for increasing intraluminal hydrostatic pressure of the left ventricle during the ventricular systolic stage of the cardiac cycle, thereby, improving systolic function of the left ventricle of the heart.

In addition to the present invention primarily applied for treating subjects having symptoms of diastolic heart failure, by reducing intraluminal hydrostatic pressure (LV filling pressure) of the left ventricle during the ventricular diastolic stage of the cardiac cycle, thereby, improving diastolic function of the left ventricle of the heart, while minimally disturbing systolic function of the heart, the present invention can be used in a variety of other cardiac related and/or non-related monitoring applications, such as pressure measurement applications, and, therapeutic applications, such as in drug delivery applications. For example, the method and device of the present invention can be implemented with inclusion and appropriate integration of a procedure and apparatus for time controlled drug delivery or release to the body, in general, and, to the cardiac region, in particular.

The following non-limiting working example illustrates the insertion and use in a healthy mammalian subject of exemplary ventricular devices for use in implementing specific case (b) of the first principle preferred embodiment of the method and device of the present invention.

Example

In Vivo Demonstration of the Implantation and use of Various Devices of the Present Invention in a Mammalian Subject Method
Anesthesia and Instrumentation:

A healthy sheep, (12 month, 31 Kg) was anesthetized (induction with xylazine+ketamine+valium; intubation and maintenance of anesthesia with enflurane; monitoring with ECG and saturation). A left thoracotomy incision was made and the chest was entered through the $5^{th}$ intercostal space. The pericardium was opened widely to allow access to the left ventricle. A fluid filled catheter was inserted into the left ventricle via the left atrial appendage and mitral valve, to allow continuous left ventricular pressure measurement and data acquisition to a PC. The distance from the base to the apex was 5-6 cm.

Preparation for Device Attachment:

After recording stable LV pressures, three segments of 8 mm diameter Dacron tube-grafts (3 cm-long each) were sutured to the LV free wall, using multiple interrupted stitches of 5/0 prolene. One segment was placed just left and parallel to the LAD coronary artery, avoiding a large diagonal branch; another segment was placed parallel to the PDA coronary artery (on its LV aspect) and the third segment was sutured midway between the two previous segments, ensuring that no damage was done to a large marginal branch of the CX coronary artery. The basal end of each graft was set approximately 1.5 cm from the AV groove, whereas the apical end was set approximately 1 cm from the apex. The heart was allowed to recover from the surgical manipulations and stable hemodynamics were achieved, with normal LV pressures.

Device Attachment and Testing:

Before the insertion of each device into the three Dacron tubes, stable LV pressures were recorded. Pressure data was recorded again after the placement of the device within its tubes (after stabilization), and repeated after device removal. Eight different wire spring devices were tested in separate experiments.

Figure 35:
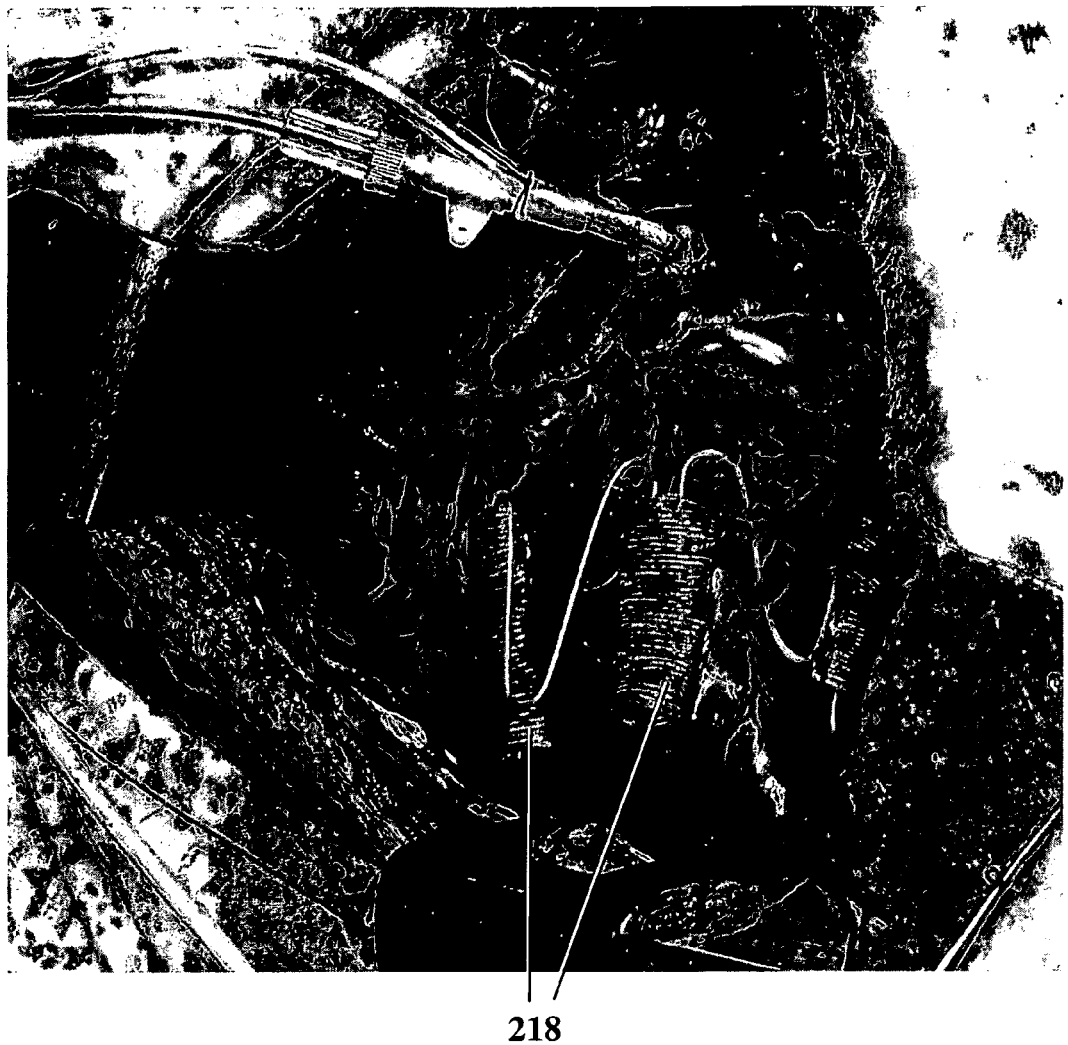
FIG. 35 is a photographic representation of one embodiment of a wire spring in vivo device that has been attached to the external ventricular wall by means of Dacron tubes.
Figure 36:
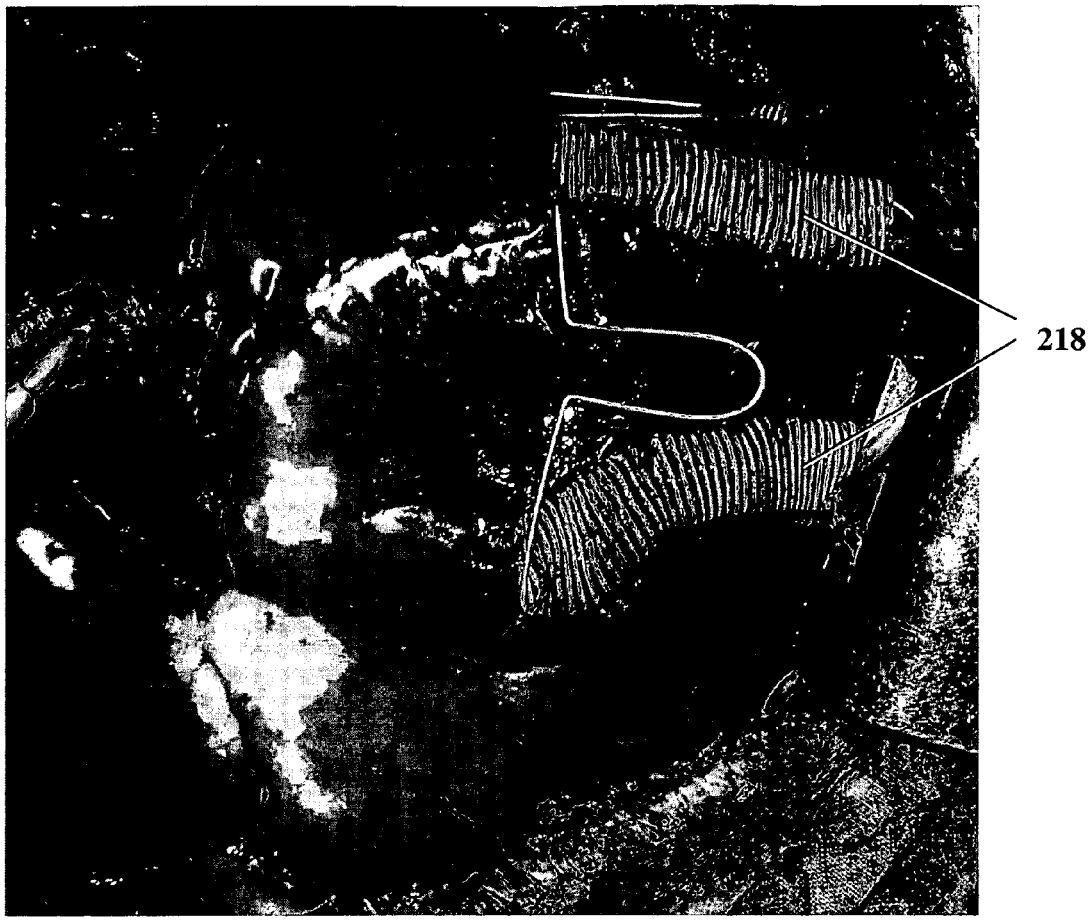
FIG. 36 is a photographic representation of another embodiment of a wire spring in vivo device that has been attached to the external ventricular wall by means of Dacron tubes.

FIGS. 35 and 36 demonstrate two different devices attached to the left ventricular wall. In each case, the in vivo device is shown attached to the external wall of the LV by means of the Dacron tubes 218.

Results:

There was some patchy discoloration of the LV free wall after suturing of the Dacron tubes. However, this was transient and did not interfere with systolic blood pressure and parameters of cardiac output such as peripheral perfusion and urinary output.

Nine applications of 8 different devices according to the present invention, of various designs and elastic forces, were tested (device # 1 was tested twice). The cumulative time in which different devices were attached to the LV surface was approximately 90 minutes, and the changing of devices required multiple manipulations on the Dacron tubes. Despite these interventions the tubes remained attached firmly throughout the experiment. It should be noted that systolic LV pressure was not impaired by any of the devices tested (data not shown). Clinical parameters of perfusion were also satisfactory throughout the experiment.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An in-vivo method for improving diastolic function of the left ventricle of the heart, comprising the steps of:
   (a) operatively connecting a device in a rest condition to the left ventricle of the heart, wherein said device includes at least one component featuring physicochemical property and behavior for potentially exerting a radially outward expansive force or pressure to at least one part of wall region of the left ventricle during ventricular diastole, wherein said at least one component is operatively connected adjacent to a wall region of the left ventricle by means of at least one component or mechanism selected from the group consisting of: biocompatible pins, biocompatible needles, biocompatible spikes, biocompatible screws, biocompatible clamps, and combinations thereof;
   (b) allowing the heart to undergo ventricular systole, during which energy is taken from the total energy of the systolic movement of the heart such that said potential radially outward expansive force or pressure of said at least one component dynamically increases to a pre-determined magnitude; and
   (c) allowing the heart to undergo ventricular diastole, during which said pre-determined magnitude of said potential radially outward expansive force or pressure of said at least one component is dynamically converted into a corresponding kinetic radially outward expansive force or pressure applied to said wall region of the left ventricle, for reducing intracardiac hydrostatic pressure during said ventricular diastole, thereby, improving the diastolic function of the left ventricle of the heart,
   wherein said method comprises transferring energy only from the systolic stage to the diastolic stage of an overall cardiac cycle such that potential energy stored in the device during the systolic movement of the heart is released as kinetic energy during the diastolic movement of the heart.

2. The method of claim 1, wherein step (a), said device is inserted into place using a surgical procedure selected from the group consisting of catheterization, thoracoscopy, thoracotomy, trans-apical deployment, open-heart, and, combinations thereof, for delivering and deploying said device to the left ventricle.

3. The method of claim 1, whereby type of said radially outward expansive force or pressure exerted to said at least one part of wall region of the left ventricle by said at least one component is selected from the group consisting of pushing, pulling, and, pulling and pushing.

4. An in-vivo device for improving diastolic function of the left ventricle of the heart, comprising:
   at least one component featuring physicochemical property and behavior for potentially exerting a radially outward expansive force or pressure to at least one part of wall region of the left ventricle during ventricular diastole, whereby:
   (a) said at least one component is operatively connected in a rest condition adjacent to a wall region of the left ventricle of the heart,
   (b) said potential radially outward expansive force or pressure of said at least one component dynamically increases to a pre-determined magnitude by taking energy from the total energy of the systolic movement during ventricular systole of the heart, and
   (c) said pre-determined magnitude of said potential radially outward expansive force or pressure of said at least one component is dynamically converted into a corresponding kinetic radially outward expansive force or pressure applied to said wall region of the left ventricle during ventricular diastole of the heart, for reducing intracardiac hydrostatic pressure during said ventricular diastole, thereby, improving the diastolic function of the left ventricle of the heart,
   wherein said radially outward expansive force or pressure is responsive to energy taken from the systolic phase of the heart only, and wherein said devices transfers energy only from the systolic stage to the diastolic stage of an overall cardiac cycle such that potential energy stored in the device during the systolic movement of the heart is released as kinetic energy during the diastolic movement of the heart.

5. The device of claim 4, whereby said at least one component has variable geometry, shape, and, form, characterized by at least one physical aspect or descriptor selected from the group consisting of circular, disc, conical, spherical, spheroidal, elliptical, ellipsoidal, parabolic, parabaloidal, hyperbolic, hyperpoloidal, spiral, helical, polygonal such as triangular, square, and, rectangular, and, combinations thereof.

6. The device of claim 4, further including at least one component or mechanism for anchoring, adhering, and/or, attaching, at least one part or region of said at least one component to said at least one part of wall region of the left ventricle where said at least one component is configured.

7. The device of claim 4, whereby type of said radially outward expansive force or pressure exerted to said at least one part of wall region of the left ventricle by said at least one component is selected from the group consisting of pushing, pulling, and, pulling and pushing.

* * * * *